(12) United States Patent
Schneider et al.

(10) Patent No.: US 9,695,245 B2
(45) Date of Patent: Jul. 4, 2017

(54) ANTI-ECTODYSPLASIN ANTIBODIES

(71) Applicant: EDIMER PHARMACEUTICALS, INC., Cambridge, MA (US)

(72) Inventors: Pascal Schneider, Epalinges (CH); Neil Kirby, Andover, MA (US); Christine Kowalczyk-Quintas, Lausanne (CH); Anh Thu Dang, Renens (CH)

(73) Assignee: EDIMER PHARMACEUTICALS, INC, Andover, MA (US)

( * ) Notice: Subject to any disclaimer, the term of this patent is extended or adjusted under 35 U.S.C. 154(b) by 0 days.

(21) Appl. No.: 14/776,547

(22) PCT Filed: Mar. 14, 2014

(86) PCT No.: PCT/US2014/028048
§ 371 (c)(1),
(2) Date: Sep. 14, 2015

(87) PCT Pub. No.: WO2014/143886
PCT Pub. Date: Sep. 18, 2014

(65) Prior Publication Data
US 2016/0075789 A1    Mar. 17, 2016

Related U.S. Application Data

(60) Provisional application No. 61/787,166, filed on Mar. 15, 2013, provisional application No. 61/903,165, filed on Nov. 12, 2013.

(51) Int. Cl.
  *C07K 16/00* (2006.01)
  *C12P 21/08* (2006.01)
  *C07K 16/28* (2006.01)
  *G01N 33/68* (2006.01)
  *A61K 39/00* (2006.01)

(52) U.S. Cl.
  CPC ..... *C07K 16/2875* (2013.01); *G01N 33/6863* (2013.01); *A61K 2039/505* (2013.01); *C07K 2317/33* (2013.01); *C07K 2317/76* (2013.01); *C07K 2317/92* (2013.01); *G01N 2333/70575* (2013.01)

(58) Field of Classification Search
  None
  See application file for complete search history.

(56) References Cited

U.S. PATENT DOCUMENTS

2005/0261480 A1  11/2005  Foot
2016/0075789 A1*  3/2016  Schneider .......... C07K 16/2875
                                                800/13

FOREIGN PATENT DOCUMENTS

| CN | 1800373 A | 7/2006 |
| CN | 102827279 A | 12/2012 |
| WO | 2010037836 A2 | 4/2010 |
| WO | 2010138564 A1 | 12/2010 |
| WO | 2011063237 A2 | 5/2011 |
| WO | 2011140114 A2 | 11/2011 |
| WO | 2012019061 A2 | 2/2012 |

OTHER PUBLICATIONS

Creative Biomart. CABT-31104MH. Mouse monoclonal antibody to Human EDA. Dec. 6, 2012 [according to document properties for posted document]. [Retrieved from the Internet Jun. 7, 2014 :<http://img.creativebiomart.net/pdf/CABT-31104MG,EDS/pdf>]; p. 1, Product Overview.
International Search Report for corresponding application No. PCT/US2014/028048 dated Sep. 19, 2014.

* cited by examiner

*Primary Examiner* — Michael Burkhart
(74) *Attorney, Agent, or Firm* — DT Ward, P.C.; Donna T. Ward; Lingyun Jia

(57) ABSTRACT

The present invention relates to the preparation of substantially purified anti-EDA1 monoclonal antibodies or isolated monoclonal antibody fragments or antigen binding portions or fragments thereof as well as pharmaceutical compositions containing such antibodies. The antibodies may be used in the treatment of disorders relating to excessive action of EDA1 such as hirsutism, ectopic teeth, hyperhidrosis, breast cancer, dermal eccrine cylindroma or skin disorders such as sebaceous gland hyperplasia, comedones, milia, acne, seborrhea, rosacea, steatoma, and furuncles. The anti-EDA1 antibodies are also useful in immunoassays such as sandwich ELISA.

17 Claims, 38 Drawing Sheets

Treatment regimen with of anti-EDA EctoD1 (non-blocker, control), EctoD2 and EctoD3 (antagonists)

```
                           SEQUENCE LISTING

<160> NUMBER OF SEQ ID NOS: 76

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Gly Phe Thr Phe Ser Thr Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ser Asp Gly Gly Asp Asn Thr
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Gln Tyr Asn Asp Tyr Glu Ala Met Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ser Val Asp Ser Tyr Gly Ser Ser Phe
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser
1

<210> SEQ ID NO 6
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Ser Asn Glu Asp Pro Phe Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Tyr Leu Phe Ile Asp Tyr Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Asn Pro Asn Ser Gly Asp Ala
1               5

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Ser Gly His Tyr Tyr Gly Ser Ser Gly Val Met Asp Tyr
1               5                   10                  15

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Asp Tyr His Gly Lys Ser Tyr
1               5                   10

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Thr Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Thr Asn Glu Asp Leu Tyr Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Tyr Thr Phe Thr Ser Tyr Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Tyr Pro Arg Ser Gly Asp Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Arg Gly Asp Tyr Ala Asp Val
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ser Val Ser Thr Phe Gly Asn Ser Tyr
1               5                   10

<210> SEQ ID NO 17
<211> LENGTH: 3
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 17

Leu Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Asn Ser Arg Glu Leu Pro Tyr Thr
1               5

<210> SEQ ID NO 19
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Glu Glu Ser Gly Gly Gly Leu Val Lys Ser Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Gly Lys Arg Leu Glu Trp Val
        35                  40                  45

Ala Ala Ile Ser Asp Gly Gly Asp Asn Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Ser Ala Leu Tyr Tyr Cys
                85                  90                  95

Ala Arg Gln Tyr Asn Asp Tyr Glu Ala Met Asp Tyr Trp Gly Gln Gly
            100                 105                 110

Thr Ser Leu Thr Val Ser Ser Ala Lys Thr Thr Pro Pro Ser Val Tyr
        115                 120                 125

<210> SEQ ID NO 20
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 20

Asp Ile Val Xaa Thr Gln Ser Pro Thr Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Ser Ser Phe Met His Trp Tyr Gln Gln Lys Pro Gly Gln Pro Pro
```

```
                35                  40                  45
Lys Leu Leu Phe Tyr Arg Ala Ser Asn Leu Glu Ser Gly Ile Pro Ala
         50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Phe Thr Phe Gly Ser Gly Thr Lys Leu Glu Ile Lys Arg
            100                 105                 110

Ala Asp Ala Ala Pro
        115

<210> SEQ ID NO 21
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(6)
<223> OTHER INFORMATION: Lys, Glu or Gln

<400> SEQUENCE: 21

Glu Val Gln Leu Xaa Xaa Ser Gly Pro Glu Met Val Lys Pro Gly Ala
 1               5                  10                  15

Ser Val Lys Ile Ser Cys Lys Ala Ser Gly Tyr Leu Phe Ile Asp Tyr
             20                  25                  30

Phe Met Asn Trp Val Lys Gln Ser His Gly Lys Ser Leu Asp Trp Ile
         35                  40                  45

Gly Asp Ile Asn Pro Asn Ser Gly Asp Ala Ser His Asn Gln Lys Phe
     50                  55                  60

Lys Gly Lys Ala Thr Leu Thr Val Asp Lys Ser Ser Ser Thr Val Tyr
 65                  70                  75                  80

Met Glu Leu Arg Ser Leu Thr Ser Glu Asp Ser Ala Val Tyr Tyr Cys
                 85                  90                  95

Ala Arg Ser Gly His Tyr Tyr Gly Ser Ser Gly Val Met Asp Tyr Trp
            100                 105                 110

Gly Gln Gly Thr Ser Val Thr Val Ser Ser Ala Lys Thr Thr Pro Pro
        115                 120                 125

Ser Val Tyr
        130

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 22

Asp Ile Val Xaa Thr Gln Ser Pro Ala Ser Leu Ala Val Ser Leu Gly
 1               5                  10                  15

Gln Arg Ala Thr Ile Ser Cys Lys Ala Ser Gln Ser Leu Asp Tyr His
             20                  25                  30
```

```
Gly Lys Ser Tyr Met Asn Trp Tyr Gln Gln Lys Pro Gly Gln Pro
            35                  40                  45

Arg Leu Leu Ile Tyr Thr Ala Ser Asn Leu Glu Ser Gly Ile Pro Ala
 50                  55                  60

Arg Phe Ser Gly Ser Gly Ser Gly Thr Asp Phe Thr Leu Asn Ile Leu
 65                  70                  75                  80

Pro Val Asp Glu Glu Asp Val Ala Ser Tyr Phe Cys Gln Gln Thr Asn
                 85                  90                  95

Glu Asp Leu Tyr Thr Phe Gly Gly Thr Lys Leu Glu Ile Lys Arg
            100                 105                 110

Ala Asp Ala Ala Pro
        115

<210> SEQ ID NO 23
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Glu Leu Glu Glu Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Val Tyr Pro Arg Ser Gly Asp Thr Tyr Tyr His Asp Tyr Phe
 50                  55                  60

Glu Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg Gly Asp Tyr Ala Asp Val Trp Gly Thr Gly Thr Thr Val Thr
            100                 105                 110

Val Ser Ser Ala Lys Thr Thr Pro Pro Ser Val Tyr
        115                 120

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 24

Asp Ile Val Xaa Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Phe
            20                  25                  30

Gly Asn Ser Tyr Met Leu Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
```

```
            50                  55                  60
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Asn Ser Arg
                 85                  90                  95

Glu Leu Pro Tyr Thr Phe Gly Gly Gly Thr Lys Leu Glu Ile Lys Arg
            100                 105                 110

Ala Asp Ala Ala Pro
        115

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tctggattca ctttcagtac ctatgcc                                          27

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
attagtgatg gtggtgataa tacc                                             24

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcaaggcaat ataatgacta cgaggctatg gactac                                36

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gaaagtgttg atagttatgg cagtagtttt                                       30

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 cgtgcatcc                                                              9
```

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagcaaagta atgaggatcc attcacg                                      27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tctggatatt tgttcattga ctacttt                                      27

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
attaatccta acagtgggga tgct                                         24

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcaagatcgg gccattacta cggaagtagc ggggtaatgg actac                  45

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
caaagtcttg attatcatgg taaaagttat                                   30

<210> SEQ ID NO 35
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 actgcatcc                                                           9

```
<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cagcaaacta atgaagatct gtatacg                                           27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tctggctaca ctttcacaag ctatggt                                           27

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtttatccta gaagtggtga tact                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcaagagggg actatgccga tgtc                                              24

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaaagtgtca gtacatttgg caatagttat                                        30

<210> SEQ ID NO 41
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41 cttgcatcc                                                                9

<210> SEQ ID NO 42
```

<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
cagaacagta gggagcttcc gtacacg                                                    27

<210> SEQ ID NO 43
<211> LENGTH: 384
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(384)
<220> FEATURE:
<221> NAME/KEY: modified_base
<222> LOCATION: (6)..(6)
<223> OTHER INFORMATION: a, c, t or g
<220> FEATURE:
<221> NAME/KEY: misc_feature
<222> LOCATION: (6)..(6)
<223> OTHER INFORMATION: n is a, c, g, or t

<400> SEQUENCE: 43

| gag | gtn | cag | ctg | gag | gag | tct | ggg | gga | ggc | tta | gtg | aag | tct | gga | ggg | 48 |
| Glu | Val | Gln | Leu | Glu | Glu | Ser | Gly | Gly | Gly | Leu | Val | Lys | Ser | Gly | Gly | |
| 1 | | | | 5 | | | | | 10 | | | | | 15 | | |

| tcc | ctg | aaa | ctc | tcc | tgt | gca | gcc | tct | gga | ttc | act | ttc | agt | acc | tat | 96 |
| Ser | Leu | Lys | Leu | Ser | Cys | Ala | Ala | Ser | Gly | Phe | Thr | Phe | Ser | Thr | Tyr | |
| | | | 20 | | | | | 25 | | | | | 30 | | | |

| gcc | atg | tct | tgg | gtt | cgc | cag | act | ccg | ggg | aag | agg | ctg | gag | tgg | gtc | 144 |
| Ala | Met | Ser | Trp | Val | Arg | Gln | Thr | Pro | Gly | Lys | Arg | Leu | Glu | Trp | Val | |
| | | 35 | | | | | 40 | | | | | 45 | | | | |

| gca | gcc | att | agt | gat | ggt | ggt | gat | aat | acc | tac | tat | cta | gac | agt | gtg | 192 |
| Ala | Ala | Ile | Ser | Asp | Gly | Gly | Asp | Asn | Thr | Tyr | Tyr | Leu | Asp | Ser | Val | |
| | 50 | | | | | 55 | | | | | 60 | | | | | |

| aag | ggt | cga | ttc | acc | atc | tcc | aga | gac | aat | gcc | aag | aac | acc | ctg | tac | 240 |
| Lys | Gly | Arg | Phe | Thr | Ile | Ser | Arg | Asp | Asn | Ala | Lys | Asn | Thr | Leu | Tyr | |
| 65 | | | | | 70 | | | | | 75 | | | | | 80 | |

| ctg | caa | atg | agc | agt | ctg | agg | tct | gag | gac | tcg | gcc | ttg | tat | tac | tgt | 288 |
| Leu | Gln | Met | Ser | Ser | Leu | Arg | Ser | Glu | Asp | Ser | Ala | Leu | Tyr | Tyr | Cys | |
| | | | | 85 | | | | | 90 | | | | | 95 | | |

| gca | agg | caa | tat | aat | gac | tac | gag | gct | atg | gac | tac | tgg | ggt | caa | gga | 336 |
| Ala | Arg | Gln | Tyr | Asn | Asp | Tyr | Glu | Ala | Met | Asp | Tyr | Trp | Gly | Gln | Gly | |
| | | | 100 | | | | | 105 | | | | | 110 | | | |

| acc | tca | ctc | acc | gtc | tcc | tca | gcc | aaa | acg | aca | ccc | cca | tct | gtc | tat | 384 |
| Thr | Ser | Leu | Thr | Val | Ser | Ser | Ala | Lys | Thr | Thr | Pro | Pro | Ser | Val | Tyr | |
| | | 115 | | | | | 120 | | | | | 125 | | | | |

<210> SEQ ID NO 44
<211> LENGTH: 128
<212> TYPE: PRT
<213> ORGANISM: Artificial Sequence
<220> FEATURE:
<223> OTHER INFORMATION: Synthetic Construct

<400> SEQUENCE: 44

| Glu | Val | Gln | Leu | Glu | Glu | Ser | Gly | Gly | Gly | Leu | Val | Lys | Ser | Gly | Gly |
| 1 | | | | 5 | | | | | 10 | | | | | 15 | |

| Ser | Leu | Lys | Leu | Ser | Cys | Ala | Ala | Ser | Gly | Phe | Thr | Phe | Ser | Thr | Tyr |

```
                      20                  25                  30
Ala Met Ser Trp Val Arg Gln Thr Pro Gly Lys Arg Leu Glu Trp Val
             35                  40                  45

Ala Ala Ile Ser Asp Gly Gly Asp Asn Thr Tyr Tyr Leu Asp Ser Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Ser Ala Leu Tyr Tyr Cys
                 85                  90                  95

Ala Arg Gln Tyr Asn Asp Tyr Glu Ala Met Asp Tyr Trp Gly Gln Gly
             100                 105                 110

Thr Ser Leu Thr Val Ser Ser Ala Lys Thr Thr Pro Pro Ser Val Tyr
         115                 120                 125

<210> SEQ ID NO 45
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)
<220> FEATURE:
<221> NAME/KEY: modified_base
<222> LOCATION: (10)..(10)
<223> OTHER INFORMATION: a, c, t or g
<220> FEATURE:
<221> NAME/KEY: misc_feature
<222> LOCATION: (10)..(10)
<223> OTHER INFORMATION: n is a, c, g, or t

<400> SEQUENCE: 45 gat att gtg ntg acc cag tct cca act tct ttg gct gtg tct cta ggg      48
Asp Ile Val Xaa Thr Gln Ser Pro Thr Ser Leu Ala Val Ser Leu Gly
  1               5                  10                  15 cag agg gcc acc ata tcc tgc aga gcc agt gaa agt gtt gat agt tat      96
Gln Arg Ala Thr Ile Ser Cys Arg Ala Ser Glu Ser Val Asp Ser Tyr
             20                  25                  30 ggc agt agt ttt atg cac tgg tac cag cag aaa cca gga cag cca ccc     144
Gly Ser Ser Phe Met His Trp Tyr Gln Gln Lys Pro Gly Gln Pro Pro
         35                  40                  45 aaa ctc ctc ttc tat cgt gca tcc aac cta gaa tct ggg atc cct gcc     192
Lys Leu Leu Phe Tyr Arg Ala Ser Asn Leu Glu Ser Gly Ile Pro Ala
     50                  55                  60 agg ttc agt ggc agt ggg tct agg aca gac ttc acc ctc acc att aat     240
Arg Phe Ser Gly Ser Gly Ser Arg Thr Asp Phe Thr Leu Thr Ile Asn
 65                  70                  75                  80 cct gtg gag gct gat gat gtt gca acc tat tac tgt cag caa agt aat     288
Pro Val Glu Ala Asp Asp Val Ala Thr Tyr Tyr Cys Gln Gln Ser Asn
                 85                  90                  95 gag gat cca ttc acg ttc ggc tcg ggg aca aag ttg gaa ata aaa cgg     336
Glu Asp Pro Phe Thr Phe Gly Ser Gly Thr Lys Leu Glu Ile Lys Arg
             100                 105                 110 gct gat gct gca cca                                                 351
Ala Asp Ala Ala Pro
         115

<210> SEQ ID NO 46
<211> LENGTH: 117
<212> TYPE: PRT
<213> ORGANISM: Artificial Sequence
```

-continued

```
<220> FEATURE:
<221> NAME/KEY: misc_feature
<222> LOCATION: (4)..(4)
<223> OTHER INFORMATION: The 'Xaa' at location 4 stands for Met, Val,
      or Leu.
<220> FEATURE:
<223> OTHER INFORMATION: Synthetic Construct

<400> SEQUENCE: 46

Asp Ile Val Xaa Thr Gln Ser Pro Thr Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Ser Ser Phe Met His Trp Tyr Gln Gln Lys Pro Gly Gln Pro Pro
        35                  40                  45

Lys Leu Leu Phe Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Phe Thr Phe Gly Ser Gly Thr Lys Leu Glu Ile Lys Arg
            100                 105                 110

Ala Asp Ala Ala Pro
        115

<210> SEQ ID NO 47
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(393)
<220> FEATURE:
<221> NAME/KEY: modified_base
<222> LOCATION: (6)..(6)
<223> OTHER INFORMATION: a, c, t or g
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (13)..(13)
<223> OTHER INFORMATION: a, c or g
<220> FEATURE:
<221> NAME/KEY: misc_feature
<222> LOCATION: (13)..(18)
<223> OTHER INFORMATION: The codons encompassed in this region may not
      code for a "tag" stop codon
<220> FEATURE:
<221> NAME/KEY: modified_base
<222> LOCATION: (16)..(16)
<223> OTHER INFORMATION: a, c or g

<400> SEQUENCE: 47 gag gtn cag ctg nag nag tct gga cct gag atg gtg aag cct ggg gcc      48
Glu Val Gln Leu Xaa Xaa Ser Gly Pro Glu Met Val Lys Pro Gly Ala
1               5                   10                  15 tca gtg aag ata tcc tgt aag gct tct gga tat ttg ttc att gac tac      96
Ser Val Lys Ile Ser Cys Lys Ala Ser Gly Tyr Leu Phe Ile Asp Tyr
            20                  25                  30 ttt atg aac tgg gtg aaa cag agc cat gga aag agc ctt gac tgg att     144
Phe Met Asn Trp Val Lys Gln Ser His Gly Lys Ser Leu Asp Trp Ile
```

```
                   35                  40                  45
gga gat att aat cct aac agt ggg gat gct agc cac aac cag aag ttc      192
Gly Asp Ile Asn Pro Asn Ser Gly Asp Ala Ser His Asn Gln Lys Phe
 50                  55                  60 aag ggc aag gcc aca ttg act gta gac aag tcc tcc agc aca gtc tac      240
Lys Gly Lys Ala Thr Leu Thr Val Asp Lys Ser Ser Ser Thr Val Tyr
 65                  70                  75                  80 atg gaa ctc cgc agc ctg aca tct gag gac tct gca gtc tat tac tgt      288
Met Glu Leu Arg Ser Leu Thr Ser Glu Asp Ser Ala Val Tyr Tyr Cys
                 85                  90                  95 gca aga tcg ggc cat tac tac gga agc agc ggg gta atg gac tac tgg      336
Ala Arg Ser Gly His Tyr Tyr Gly Ser Ser Gly Val Met Asp Tyr Trp
            100                 105                 110 ggt caa gga acc tca gtc acc gtc tcc tca gcc aaa acg aca ccc cca      384
Gly Gln Gly Thr Ser Val Thr Val Ser Ser Ala Lys Thr Thr Pro Pro
        115                 120                 125 tct gtc tat                                                          393
Ser Val Tyr
    130

<210> SEQ ID NO 48
<211> LENGTH: 131
<212> TYPE: PRT
<213> ORGANISM: Artificial Sequence
<220> FEATURE:
<221> NAME/KEY: misc_feature
<222> LOCATION: (5)..(5)
<223> OTHER INFORMATION: The 'Xaa' at location 5 stands for Lys, Glu,
      or Gln.
<220> FEATURE:
<221> NAME/KEY: misc_feature
<222> LOCATION: (6)..(6)
<223> OTHER INFORMATION: The 'Xaa' at location 6 stands for Lys, Glu,
      or Gln.
<220> FEATURE:
<223> OTHER INFORMATION: Synthetic Construct

<400> SEQUENCE: 48

Glu Val Gln Leu Xaa Xaa Ser Gly Pro Glu Met Val Lys Pro Gly Ala
 1               5                  10                  15

Ser Val Lys Ile Ser Cys Lys Ala Ser Gly Tyr Leu Phe Ile Asp Tyr
            20                  25                  30

Phe Met Asn Trp Val Lys Gln Ser His Gly Lys Ser Leu Asp Trp Ile
         35                  40                  45

Gly Asp Ile Asn Pro Asn Ser Gly Asp Ala Ser His Asn Gln Lys Phe
 50                  55                  60

Lys Gly Lys Ala Thr Leu Thr Val Asp Lys Ser Ser Ser Thr Val Tyr
 65                  70                  75                  80

Met Glu Leu Arg Ser Leu Thr Ser Glu Asp Ser Ala Val Tyr Tyr Cys
                 85                  90                  95

Ala Arg Ser Gly His Tyr Tyr Gly Ser Ser Gly Val Met Asp Tyr Trp
            100                 105                 110

Gly Gln Gly Thr Ser Val Thr Val Ser Ser Ala Lys Thr Thr Pro Pro
        115                 120                 125

Ser Val Tyr
    130

<210> SEQ ID NO 49
<211> LENGTH: 351
<212> TYPE: DNA
<213> ORGANISM: Artificial Sequence
<220> FEATURE:
```

-continued

<223> OTHER INFORMATION: Description of Artificial Sequence: Synthetic
      polynucleotide
<220> FEATURE:
<221> NAME/KEY: CDS
<222> LOCATION: (1)..(351)
<220> FEATURE:
<221> NAME/KEY: modified_base
<222> LOCATION: (10)..(10)
<223> OTHER INFORMATION: a, c, t or g
<220> FEATURE:
<221> NAME/KEY: misc_feature
<222> LOCATION: (10)..(10)
<223> OTHER INFORMATION: n is a, c, g, or t

<400> SEQUENCE: 49

```
gat att gtg ntg acc cag tct cca gct tct ttg gct gtg tct cta ggg      48
Asp Ile Val Xaa Thr Gln Ser Pro Ala Ser Leu Ala Val Ser Leu Gly
1               5                  10                  15 cag agg gcc acc atc tcc tgc aag gcc agc caa agt ctt gat tat cat      96
Gln Arg Ala Thr Ile Ser Cys Lys Ala Ser Gln Ser Leu Asp Tyr His
            20                  25                  30 ggt aaa agt tat atg aac tgg tac caa cag aaa cca gga cag cca ccc     144
Gly Lys Ser Tyr Met Asn Trp Tyr Gln Gln Lys Pro Gly Gln Pro Pro
        35                  40                  45 agg ctc ctc atc tat act gca tcc aat cta gag tct ggg atc cca gcc     192
Arg Leu Leu Ile Tyr Thr Ala Ser Asn Leu Glu Ser Gly Ile Pro Ala
    50                  55                  60 agg ttt agt ggc agt ggg tct ggg aca gac ttc acc ctc aac att ctt     240
Arg Phe Ser Gly Ser Gly Ser Gly Thr Asp Phe Thr Leu Asn Ile Leu
65                  70                  75                  80 cct gtg gat gag gag gat gtt gca tcc tat ttc tgt cag caa act aat    288
Pro Val Asp Glu Glu Asp Val Ala Ser Tyr Phe Cys Gln Gln Thr Asn
                85                  90                  95 gaa gat ctg tat acg ttc ggc ggg ggg acc aag ctg gaa ata aaa cgg    336
Glu Asp Leu Tyr Thr Phe Gly Gly Gly Thr Lys Leu Glu Ile Lys Arg
            100                 105                 110 gct gat gct gca cca                                                 351
Ala Asp Ala Ala Pro
        115
```

<210> SEQ ID NO 50
<211> LENGTH: 117
<212> TYPE: PRT
<213> ORGANISM: Artificial Sequence
<220> FEATURE:
<221> NAME/KEY: misc_feature
<222> LOCATION: (4)..(4)
<223> OTHER INFORMATION: The 'Xaa' at location 4 stands for Met, Val,
      or Leu.
<220> FEATURE:
<223> OTHER INFORMATION: Synthetic Construct

<400> SEQUENCE: 50

```
Asp Ile Val Xaa Thr Gln Ser Pro Ala Ser Leu Ala Val Ser Leu Gly
1               5                  10                  15

Gln Arg Ala Thr Ile Ser Cys Lys Ala Ser Gln Ser Leu Asp Tyr His
            20                  25                  30

Gly Lys Ser Tyr Met Asn Trp Tyr Gln Gln Lys Pro Gly Gln Pro Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Asn Ile Leu
65                  70                  75                  80

Pro Val Asp Glu Glu Asp Val Ala Ser Tyr Phe Cys Gln Gln Thr Asn
```

85                  90                  95
Glu Asp Leu Tyr Thr Phe Gly Gly Gly Thr Lys Leu Glu Ile Lys Arg
                100                 105                 110

Ala Asp Ala Ala Pro
        115

<210> SEQ ID NO 51
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)

<400> SEQUENCE: 51 gag gtt gag ctg gag gag tct gga gct gag ctg gcg agg cct ggg gct      48
Glu Val Glu Leu Glu Glu Ser Gly Ala Glu Leu Ala Arg Pro Gly Ala
1               5                   10                  15 tca gtg aag ctg tcc tgc aag gct tct ggc tac act ttc aca agc tat     96
Ser Val Lys Leu Ser Cys Lys Ala Ser Gly Tyr Thr Phe Thr Ser Tyr
            20                  25                  30 ggt att agc tgg gtg aag cag aga act gga cag ggc ctt gag tgg att    144
Gly Ile Ser Trp Val Lys Gln Arg Thr Gly Gln Gly Leu Glu Trp Ile
        35                  40                  45 gga gaa gtt tat cct aga agt ggt gat act tac tac cat gac tac ttc    192
Gly Glu Val Tyr Pro Arg Ser Gly Asp Thr Tyr Tyr His Asp Tyr Phe
    50                  55                  60 gag ggc aag gcc aca ctg act gca gac aaa tcc tcc agc aca gcg tac    240
Glu Gly Lys Ala Thr Leu Thr Ala Asp Lys Ser Ser Ser Thr Ala Tyr
65                  70                  75                  80 atg gaa ctc cgc agc ctg aca tct gag gac tct gcg gtc tat ttc tgt    288
Met Glu Leu Arg Ser Leu Thr Ser Glu Asp Ser Ala Val Tyr Phe Cys
                85                  90                  95 gca aga ggg gac tat gcc gat gtc tgg ggc aca ggg acc acg gtc acc    336
Ala Arg Gly Asp Tyr Ala Asp Val Trp Gly Thr Gly Thr Thr Val Thr
            100                 105                 110 gtc tcc tca gcc aaa acg aca ccc cca tct gtc tat                    372
Val Ser Ser Ala Lys Thr Thr Pro Pro Ser Val Tyr
        115                 120

<210> SEQ ID NO 52
<211> LENGTH: 124
<212> TYPE: PRT
<213> ORGANISM: Artificial Sequence
<220> FEATURE:
<223> OTHER INFORMATION: Synthetic Construct

<400> SEQUENCE: 52

Glu Val Glu Leu Glu Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Val Tyr Pro Arg Ser Gly Asp Thr Tyr Tyr His Asp Tyr Phe
    50                  55                  60

Glu Gly Lys Ala Thr Leu Thr Ala Asp Lys Ser Ser Ser Thr Ala Tyr
65                  70                  75                  80

```
Met Glu Leu Arg Ser Leu Thr Ser Glu Asp Ser Ala Val Tyr Phe Cys
             85                  90                  95

Ala Arg Gly Asp Tyr Ala Asp Val Trp Gly Thr Gly Thr Thr Val Thr
            100                 105                 110

Val Ser Ser Ala Lys Thr Thr Pro Pro Ser Val Tyr
        115                 120

<210> SEQ ID NO 53
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)
<220> FEATURE:
<221> NAME/KEY: modified_base
<222> LOCATION: (10)..(10)
<223> OTHER INFORMATION: a, c, t or g
<220> FEATURE:
<221> NAME/KEY: misc_feature
<222> LOCATION: (10)..(10)
<223> OTHER INFORMATION: n is a, c, g, or t

<400> SEQUENCE: 53 gat att gtg ntg acc cag tct cca gct tcc tta gct gta tct ctg ggg     48
Asp Ile Val Xaa Thr Gln Ser Pro Ala Ser Leu Ala Val Ser Leu Gly
1               5                   10                  15 cag agg gcc acc atc tca tgc agg gcc agc aaa agt gtc agt aca ttt     96
Gln Arg Ala Thr Ile Ser Cys Arg Ala Ser Lys Ser Val Ser Thr Phe
            20                  25                  30 ggc aat agt tat atg ctc tgg tac caa cag aaa cca gga cag cca ccc    144
Gly Asn Ser Tyr Met Leu Trp Tyr Gln Gln Lys Pro Gly Gln Pro Pro
        35                  40                  45 aaa ctc ctc atc tat ctt gca tcc aac cta gaa tct ggg gtc cct gcc    192
Lys Leu Leu Ile Tyr Leu Ala Ser Asn Leu Glu Ser Gly Val Pro Ala
    50                  55                  60 agg ttc agt ggc agt ggg tct ggg aca gac ttc acc ctc aac atc cat    240
Arg Phe Ser Gly Ser Gly Ser Gly Thr Asp Phe Thr Leu Asn Ile His
65                  70                  75                  80 cct gtg gag gag gag gat gct gca acc tat tac tgt cag aac agt agg    288
Pro Val Glu Glu Glu Asp Ala Ala Thr Tyr Tyr Cys Gln Asn Ser Arg
                85                  90                  95 gag ctt ccg tac acg ttc gga ggg ggg acc aag ctg gaa ata aaa cgg    336
Glu Leu Pro Tyr Thr Phe Gly Gly Gly Thr Lys Leu Glu Ile Lys Arg
            100                 105                 110 gct gat gct gca cca                                                351
Ala Asp Ala Ala Pro
        115

<210> SEQ ID NO 54
<211> LENGTH: 117
<212> TYPE: PRT
<213> ORGANISM: Artificial Sequence
<220> FEATURE:
<221> NAME/KEY: misc_feature
<222> LOCATION: (4)..(4)
<223> OTHER INFORMATION: The 'Xaa' at location 4 stands for Met, Val,
      or Leu.
<220> FEATURE:
<223> OTHER INFORMATION: Synthetic Construct

<400> SEQUENCE: 54

Asp Ile Val Xaa Thr Gln Ser Pro Ala Ser Leu Ala Val Ser Leu Gly
```

```
            1               5                   10                  15
        Gln Arg Ala Thr Ile Ser Cys Arg Ala Ser Lys Ser Val Ser Thr Phe
                        20                  25                  30

Gly Asn Ser Tyr Met Leu Trp Tyr Gln Gln Lys Pro Gly Gln Pro Pro
                        35                  40                  45

Lys Leu Leu Ile Tyr Leu Ala Ser Asn Leu Glu Ser Gly Val Pro Ala
                        50                  55                  60

Arg Phe Ser Gly Ser Gly Ser Gly Thr Asp Phe Thr Leu Asn Ile His
         65                 70                  75                  80

Pro Val Glu Glu Glu Asp Ala Ala Thr Tyr Tyr Cys Gln Asn Ser Arg
                        85                  90                  95

Glu Leu Pro Tyr Thr Phe Gly Gly Gly Thr Lys Leu Glu Ile Lys Arg
                        100                 105                 110

Ala Asp Ala Ala Pro
                        115

<210> SEQ ID NO 55
<211> LENGTH: 391
<212> TYPE: PRT
<213> ORGANISM: Homo sapiens

<400> SEQUENCE: 55

Met Gly Tyr Pro Glu Val Glu Arg Arg Glu Leu Leu Pro Ala Ala Ala
         1              5                   10                  15

Pro Arg Glu Arg Gly Ser Gln Gly Cys Gly Cys Gly Gly Ala Pro Ala
                        20                  25                  30

Arg Ala Gly Glu Gly Asn Ser Cys Leu Leu Phe Leu Gly Phe Phe Gly
                        35                  40                  45

Leu Ser Leu Ala Leu His Leu Leu Thr Leu Cys Cys Tyr Leu Glu Leu
                        50                  55                  60

Arg Ser Glu Leu Arg Arg Glu Arg Gly Ala Glu Ser Arg Leu Gly Gly
         65                 70                  75                  80

Ser Gly Thr Pro Gly Thr Ser Gly Thr Leu Ser Ser Leu Gly Gly Leu
                        85                  90                  95

Asp Pro Asp Ser Pro Ile Thr Ser His Leu Gly Gln Pro Ser Pro Lys
                        100                 105                 110

Gln Gln Pro Leu Glu Pro Gly Glu Ala Ala Leu His Ser Asp Ser Gln
                        115                 120                 125

Asp Gly His Gln Met Ala Leu Leu Asn Phe Phe Phe Pro Asp Glu Lys
                        130                 135                 140

Pro Tyr Ser Glu Glu Glu Ser Arg Arg Val Arg Arg Asn Lys Arg Ser
        145                 150                 155                 160

Lys Ser Asn Glu Gly Ala Asp Gly Pro Val Lys Asn Lys Lys Lys Gly
                        165                 170                 175

Lys Lys Ala Gly Pro Pro Gly Pro Asn Gly Pro Pro Gly Pro Pro Gly
                        180                 185                 190

Pro Pro Gly Pro Gln Gly Pro Pro Gly Ile Pro Gly Ile Pro Gly Ile
                        195                 200                 205

Pro Gly Thr Thr Val Met Gly Pro Pro Gly Pro Pro Gly Pro Pro Gly
                        210                 215                 220

Pro Gln Gly Pro Pro Gly Leu Gln Gly Pro Ser Gly Ala Ala Asp Lys
        225                 230                 235                 240

Ala Gly Thr Arg Glu Asn Gln Pro Ala Val Val His Leu Gln Gly Gln
                        245                 250                 255
```

```
Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
        355                 360                 365

Ile Ser Ile Asn Met Ser Lys His Thr Thr Phe Phe Gly Ala Ile Arg
    370                 375                 380

Leu Gly Glu Ala Pro Ala Ser
385                 390

<210> SEQ ID NO 56
<211> LENGTH: 389
<212> TYPE: PRT
<213> ORGANISM: Mus musculus

<400> SEQUENCE: 56

Met Gly Tyr Pro Glu Val Glu Arg Arg Glu Pro Leu Pro Ala Ala Ala
1               5                   10                  15

Pro Arg Glu Arg Gly Ser Gln Gly Cys Gly Cys Arg Gly Ala Pro Ala
            20                  25                  30

Arg Ala Gly Glu Gly Asn Ser Cys Arg Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Thr Glu Ser Arg Leu Gly Gly
65                  70                  75                  80

Pro Gly Ala Pro Gly Thr Ser Gly Thr Leu Ser Ser Pro Gly Ser Leu
            85                  90                  95

Asp Pro Val Gly Pro Ile Thr Arg His Leu Gly Gln Pro Ser Phe Gln
            100                 105                 110

Gln Gln Pro Leu Glu Pro Gly Glu Asp Pro Leu Pro Asp Ser Gln
        115                 120                 125

Asp Arg His Gln Met Ala Leu Leu Asn Phe Phe Phe Pro Asp Glu Lys
    130                 135                 140

Ala Tyr Ser Glu Glu Ser Arg Val Arg Arg Asn Lys Arg Ser
145                 150                 155                 160

Lys Ser Gly Glu Gly Ala Asp Gly Pro Val Lys Asn Lys Lys Gly
            165                 170                 175

Lys Lys Ala Gly Pro Pro Gly Pro Asn Gly Pro Gly Pro Pro Gly
        180                 185                 190

Pro Pro Gly Pro Gln Gly Pro Pro Gly Ile Pro Gly Ile Pro Gly Ile
    195                 200                 205

Pro Gly Thr Thr Val Met Gly Pro Pro Gly Pro Pro Gly Pro Pro Gly
    210                 215                 220

Pro Gln Gly Pro Pro Gly Leu Gln Gly Pro Ser Gly Ala Ala Asp Lys
225                 230                 235                 240
```

```
Thr Gly Thr Arg Glu Asn Gln Pro Ala Val Val His Leu Gln Gly Gln
                245                 250                 255

Gly Ser Ala Ile Gln Val Lys Asn Asp Leu Ser Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Tyr Tyr Ile Asn Phe Thr Asp Phe Ala Ser Tyr Glu Val
305                 310                 315                 320

Val Val Asp Glu Lys Pro Phe Leu Gln Cys Thr Arg Ser Ile Glu Thr
                325                 330                 335

Gly Lys Thr Asn Tyr Asn Thr Cys Tyr Thr Ala Gly Val Cys Leu Leu
            340                 345                 350

Lys Ala Arg Gln Lys Ile Ala Val Lys Met Val His Ala Asp Ile Ser
        355                 360                 365

Ile Asn Met Ser Lys His Thr Thr Phe Phe Gly Ala Ile Arg Leu Gly
    370                 375                 380

Glu Ala Pro Ala Ser
385

<210> SEQ ID NO 57
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Met Leu Glu Glu Ser Gly Gly Gly Leu Val Lys Ser Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Gly Lys Arg Leu Glu Trp Val
        35                  40                  45

Ala Ala Ile Ser Asp Gly Gly Asp Asn Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Ser Ala Leu Tyr Tyr Cys
                85                  90                  95

Ala Arg Gln Tyr Asn Asp Tyr Glu Ala Met Asp Tyr Trp Gly Gln Gly
            100                 105                 110

Thr Ser Leu Thr Val Ser Ser Ala Lys Thr Thr Pro Pro Ser Val Tyr
        115                 120                 125

<210> SEQ ID NO 58
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Leu Thr Gln Ser Pro Thr Ser Leu Ala Val Ser Leu Gly
1               5                   10                  15
```

```
Gln Arg Ala Thr Ile Ser Cys Arg Ala Ser Glu Ser Val Asp Ser Tyr
            20                  25                  30

Gly Ser Ser Phe Met His Trp Tyr Gln Gln Lys Pro Gly Gln Pro Pro
        35                  40                  45

Lys Leu Leu Phe Tyr Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Phe Thr Phe Gly Ser Gly Thr Lys Leu Glu Ile Lys Arg
            100                 105                 110

Ala Asp Ala Ala Pro
        115
```

<210> SEQ ID NO 59
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Ala Val Gln Leu Gln Gln Ser Gly Pro Glu Met Val Lys Pro Gly Ala
 1               5                  10                  15

Ser Val Lys Ile Ser Cys Lys Ala Ser Gly Tyr Leu Phe Ile Asp Tyr
            20                  25                  30

Phe Met Asn Trp Val Lys Gln Ser His Gly Lys Ser Leu Asp Trp Ile
        35                  40                  45

Gly Asp Ile Asn Pro Asn Ser Gly Asp Ala Ser His Asn Gln Lys Phe
 50                  55                  60

Lys Gly Lys Ala Thr Leu Thr Val Asp Lys Ser Ser Ser Thr Val Tyr
 65                  70                  75                  80

Met Glu Leu Arg Ser Leu Thr Ser Glu Asp Ser Ala Val Tyr Tyr Cys
                 85                  90                  95

Ala Arg Ser Gly His Tyr Tyr Gly Ser Ser Gly Val Met Asp Tyr Trp
            100                 105                 110

Gly Gln Gly Thr Ser Val Thr Val Ser Ser Ala Lys Thr Thr Pro Pro
        115                 120                 125

Ser Val Tyr
    130
```

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Leu Asp Tyr His
            20                  25                  30

Gly Lys Ser Tyr Met Asn Trp Tyr Gln Gln Lys Pro Gly Gln Pro Pro
        35                  40                  45
```

```
Arg Leu Leu Ile Tyr Thr Ala Ser Asn Leu Glu Ser Gly Ile Pro Ala
         50                  55                  60

Arg Phe Ser Gly Ser Gly Ser Gly Thr Asp Phe Thr Leu Asn Ile Leu
 65                  70                  75                  80

Pro Val Asp Glu Glu Asp Val Ala Ser Tyr Phe Cys Gln Gln Thr Asn
                 85                  90                  95

Glu Asp Leu Tyr Thr Phe Gly Gly Gly Thr Lys Leu Glu Ile Lys Arg
            100                 105                 110

Ala Asp Ala Ala Pro
        115

<210> SEQ ID NO 61
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu His Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
             20                  25                  30

Gly Ile Ser Trp Val Lys Gln Arg Thr Gly Gln Gly Leu Glu Trp Ile
         35                  40                  45

Gly Glu Val Tyr Pro Arg Ser Gly Asp Thr Tyr Tyr His Asp Tyr Phe
     50                  55                  60

Glu Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg Gly Asp Tyr Ala Asp Val Trp Gly Thr Gly Thr Thr Val Thr
            100                 105                 110

Val Ser Ser Ala Lys Thr Thr Pro Pro Ser Val Tyr
        115                 120

<210> SEQ ID NO 62
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Phe
             20                  25                  30

Gly Asn Ser Tyr Met Leu Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Asn Ser Arg
                 85                  90                  95
```

Glu Leu Pro Tyr Thr Phe Gly Gly Gly Thr Lys Leu Glu Ile Lys Arg
                100                 105                 110

Ala Asp Ala Ala Pro
        115

<210> SEQ ID NO 63
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(384)

<400> SEQUENCE: 63 gaa gtg atg ctg gag gag tct ggg gga ggc tta gtg aag tct gga ggg      48
Glu Val Met Leu Glu Glu Ser Gly Gly Gly Leu Val Lys Ser Gly Gly
1               5                   10                  15 tcc ctg aaa ctc tcc tgt gca gcc tct gga ttc act ttc agt acc tat      96
Ser Leu Lys Leu Ser Cys Ala Ala Ser Gly Phe Thr Phe Ser Thr Tyr
            20                  25                  30 gcc atg tct tgg gtt cgc cag act ccg ggg aag agg ctg gag tgg gtc     144
Ala Met Ser Trp Val Arg Gln Thr Pro Gly Lys Arg Leu Glu Trp Val
        35                  40                  45 gca gcc att agt gat ggt ggt gat aat acc tac tat cta gac agt gtg     192
Ala Ala Ile Ser Asp Gly Gly Asp Asn Thr Tyr Tyr Leu Asp Ser Val
    50                  55                  60 aag ggt cga ttc acc atc tcc aga gac aat gcc aag aac acc ctg tac     240
Lys Gly Arg Phe Thr Ile Ser Arg Asp Asn Ala Lys Asn Thr Leu Tyr
65                  70                  75                  80 ctg caa atg agc agt ctg agg tct gag gac tcg gcc ttg tat tac tgt     288
Leu Gln Met Ser Ser Leu Arg Ser Glu Asp Ser Ala Leu Tyr Tyr Cys
                85                  90                  95 gca agg caa tat aat gac tac gag gct atg gac tac tgg ggt caa gga     336
Ala Arg Gln Tyr Asn Asp Tyr Glu Ala Met Asp Tyr Trp Gly Gln Gly
            100                 105                 110 acc tca ctc acc gtc tcc tca gcc aaa acg aca ccc cca tct gtc tat     384
Thr Ser Leu Thr Val Ser Ser Ala Lys Thr Thr Pro Pro Ser Val Tyr
        115                 120                 125

<210> SEQ ID NO 64
<211> LENGTH: 128
<212> TYPE: PRT
<213> ORGANISM: Artificial Sequence
<220> FEATURE:
<223> OTHER INFORMATION: Synthetic Construct

<400> SEQUENCE: 64

Glu Val Met Leu Glu Glu Ser Gly Gly Gly Leu Val Lys Ser Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Gly Lys Arg Leu Glu Trp Val
        35                  40                  45

Ala Ala Ile Ser Asp Gly Gly Asp Asn Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Ser Ala Leu Tyr Tyr Cys

```
                    85                  90                  95
Ala Arg Gln Tyr Asn Asp Tyr Glu Ala Met Asp Tyr Trp Gly Gln Gly
                100                 105                 110

Thr Ser Leu Thr Val Ser Ser Ala Lys Thr Thr Pro Pro Ser Val Tyr
        115                 120                 125

<210> SEQ ID NO 65
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 65 gac att gtg ctg acc caa tct cca act tct ttg gct gtg tct cta ggg      48
Asp Ile Val Leu Thr Gln Ser Pro Thr Ser Leu Ala Val Ser Leu Gly
1               5                   10                  15 cag agg gcc acc ata tcc tgc aga gcc agt gaa agt gtt gat agt tat      96
Gln Arg Ala Thr Ile Ser Cys Arg Ala Ser Glu Ser Val Asp Ser Tyr
            20                  25                  30 ggc agt agt ttt atg cac tgg tac cag cag aaa cca gga cag cca ccc     144
Gly Ser Ser Phe Met His Trp Tyr Gln Gln Lys Pro Gly Gln Pro Pro
        35                  40                  45 aaa ctc ctc ttc tat cgt gca tcc aac cta gaa tct ggg atc cct gcc     192
Lys Leu Leu Phe Tyr Arg Ala Ser Asn Leu Glu Ser Gly Ile Pro Ala
    50                  55                  60 agg ttc agt ggc agt ggg tct agg aca gac ttc acc ctc acc att aat     240
Arg Phe Ser Gly Ser Gly Ser Arg Thr Asp Phe Thr Leu Thr Ile Asn
65                  70                  75                  80 cct gtg gag gct gat gat gtt gca acc tat tac tgt cag caa agt aat     288
Pro Val Glu Ala Asp Asp Val Ala Thr Tyr Tyr Cys Gln Gln Ser Asn
                85                  90                  95 gag gat cca ttc acg ttc ggc tcg ggg aca aag ttg gaa ata aaa cgg     336
Glu Asp Pro Phe Thr Phe Gly Ser Gly Thr Lys Leu Glu Ile Lys Arg
            100                 105                 110 gct gat gct gca cca                                                  351
Ala Asp Ala Ala Pro
        115

<210> SEQ ID NO 66
<211> LENGTH: 117
<212> TYPE: PRT
<213> ORGANISM: Artificial Sequence
<220> FEATURE:
<223> OTHER INFORMATION: Synthetic Construct

<400> SEQUENCE: 66

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Ser Ser Phe Met His Trp Tyr Gln Gln Lys Pro Gly Gln Pro Pro
        35                  40                  45

Lys Leu Leu Phe Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80
```

```
                Pro Val Glu Ala Asp Asp Val Ala Thr Tyr Tyr Cys Gln Gln Ser Asn
                             85                  90                  95

Glu Asp Pro Phe Thr Phe Gly Ser Gly Thr Lys Leu Glu Ile Lys Arg
                            100                 105                 110

Ala Asp Ala Ala Pro
                        115

<210> SEQ ID NO 67
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(393)

<400> SEQUENCE: 67 gcg gtc cag ctg caa caa tct gga cct gag atg gtg aag cct ggg gcc       48
Ala Val Gln Leu Gln Gln Ser Gly Pro Glu Met Val Lys Pro Gly Ala
1               5                   10                  15 tca gtg aag ata tcc tgt aag gct tct gga tat ttg ttc att gac tac       96
Ser Val Lys Ile Ser Cys Lys Ala Ser Gly Tyr Leu Phe Ile Asp Tyr
            20                  25                  30 ttt atg aac tgg gtg aaa cag agc cat gga aag agc ctt gac tgg att      144
Phe Met Asn Trp Val Lys Gln Ser His Gly Lys Ser Leu Asp Trp Ile
        35                  40                  45 gga gat att aat cct aac agt ggg gat gct agc cac aac cag aag ttc      192
Gly Asp Ile Asn Pro Asn Ser Gly Asp Ala Ser His Asn Gln Lys Phe
    50                  55                  60 aag ggc aag gcc aca ttg act gta gac aag tcc tcc agc aca gtc tac      240
Lys Gly Lys Ala Thr Leu Thr Val Asp Lys Ser Ser Ser Thr Val Tyr
65                  70                  75                  80 atg gaa ctc cgc agc ctg aca tct gag gac tct gca gtc tat tac tgt      288
Met Glu Leu Arg Ser Leu Thr Ser Glu Asp Ser Ala Val Tyr Tyr Cys
                85                  90                  95 gca aga tcg ggc cat tac tac gga agt agc ggg gta atg gac tac tgg      336
Ala Arg Ser Gly His Tyr Tyr Gly Ser Ser Gly Val Met Asp Tyr Trp
            100                 105                 110 ggt caa gga acc tca gtc acc gtc tcc tca gcc aaa acg aca ccc cca      384
Gly Gln Gly Thr Ser Val Thr Val Ser Ser Ala Lys Thr Thr Pro Pro
        115                 120                 125 tct gtc tat                                                          393
Ser Val Tyr
    130

<210> SEQ ID NO 68
<211> LENGTH: 131
<212> TYPE: PRT
<213> ORGANISM: Artificial Sequence
<220> FEATURE:
<223> OTHER INFORMATION: Synthetic Construct

<400> SEQUENCE: 68

Ala Val Gln Leu Gln Gln Ser Gly Pro Glu Met Val Lys Pro Gly Ala
1               5                   10                  15

Ser Val Lys Ile Ser Cys Lys Ala Ser Gly Tyr Leu Phe Ile Asp Tyr
            20                  25                  30

Phe Met Asn Trp Val Lys Gln Ser His Gly Lys Ser Leu Asp Trp Ile
        35                  40                  45

Gly Asp Ile Asn Pro Asn Ser Gly Asp Ala Ser His Asn Gln Lys Phe
```

```
                          50                  55                  60
Lys Gly Lys Ala Thr Leu Thr Val Asp Lys Ser Ser Thr Val Tyr
 65                  70                  75                  80

Met Glu Leu Arg Ser Leu Thr Ser Glu Asp Ser Ala Val Tyr Cys
                     85                  90                  95

Ala Arg Ser Gly His Tyr Tyr Gly Ser Ser Gly Val Met Asp Tyr Trp
                    100                 105                 110

Gly Gln Gly Thr Ser Val Thr Val Ser Ser Ala Lys Thr Thr Pro Pro
            115                 120                 125

Ser Val Tyr
    130

<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 69 gac att gtg ctg acc caa tct cca gct tct ttg gct gtg tct cta ggg      48
Asp Ile Val Leu Thr Gln Ser Pro Ala Ser Leu Ala Val Ser Leu Gly
 1               5                  10                  15 cag agg gcc acc atc tcc tgc aag gcc agc caa agt ctt gat tat cat      96
Gln Arg Ala Thr Ile Ser Cys Lys Ala Ser Gln Ser Leu Asp Tyr His
             20                  25                  30 ggt aaa agt tat atg aac tgg tac caa cag aaa cca gga cag cca ccc     144
Gly Lys Ser Tyr Met Asn Trp Tyr Gln Gln Lys Pro Gly Gln Pro Pro
         35                  40                  45 agg ctc ctc atc tat act gca tcc aat cta gag tct ggg atc cca gcc     192
Arg Leu Leu Ile Tyr Thr Ala Ser Asn Leu Glu Ser Gly Ile Pro Ala
     50                  55                  60 agg ttt agt ggc agt ggg tct ggg aca gac ttc acc ctc aac att ctt     240
Arg Phe Ser Gly Ser Gly Ser Gly Thr Asp Phe Thr Leu Asn Ile Leu
 65                  70                  75                  80 cct gtg gat gag gag gat gtt gca tcc tat ttc tgt cag caa act aat     288
Pro Val Asp Glu Glu Asp Val Ala Ser Tyr Phe Cys Gln Gln Thr Asn
                 85                  90                  95 gaa gat ctg tat acg ttc ggc ggg ggg acc aag ctg gaa ata aaa cgg     336
Glu Asp Leu Tyr Thr Phe Gly Gly Gly Thr Lys Leu Glu Ile Lys Arg
            100                 105                 110 gct gat gct gca cca                                                 351
Ala Asp Ala Ala Pro
        115

<210> SEQ ID NO 70
<211> LENGTH: 117
<212> TYPE: PRT
<213> ORGANISM: Artificial Sequence
<220> FEATURE:
<223> OTHER INFORMATION: Synthetic Construct

<400> SEQUENCE: 70

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Leu Asp Tyr His
             20                  25                  30
```

Gly Lys Ser Tyr Met Asn Trp Tyr Gln Gln Lys Pro Gly Gln Pro Pro
            35                  40                  45

Arg Leu Leu Ile Tyr Thr Ala Ser Asn Leu Glu Ser Gly Ile Pro Ala
 50                  55                  60

Arg Phe Ser Gly Ser Gly Ser Gly Thr Asp Phe Thr Leu Asn Ile Leu
 65                  70                  75                  80

Pro Val Asp Glu Glu Asp Val Ala Ser Tyr Phe Cys Gln Gln Thr Asn
                85                  90                  95

Glu Asp Leu Tyr Thr Phe Gly Gly Gly Thr Lys Leu Glu Ile Lys Arg
            100                 105                 110

Ala Asp Ala Ala Pro
        115

<210> SEQ ID NO 71
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)

<400> SEQUENCE: 71 cag gtt cag ctg cac cag tct gga gct gag ctg gcg agg cct ggg gct      48
Gln Val Gln Leu His Gln Ser Gly Ala Glu Leu Ala Arg Pro Gly Ala
 1               5                  10                  15 tca gtg aag ctg tcc tgc aag gct tct ggc tac act ttc aca agc tat      96
Ser Val Lys Leu Ser Cys Lys Ala Ser Gly Tyr Thr Phe Thr Ser Tyr
            20                  25                  30 ggt att agc tgg gtg aag cag aga act gga cag ggc ctt gag tgg att     144
Gly Ile Ser Trp Val Lys Gln Arg Thr Gly Gln Gly Leu Glu Trp Ile
        35                  40                  45 gga gaa gtt tat cct aga agt ggt gat act tac tac cat gac tac ttc     192
Gly Glu Val Tyr Pro Arg Ser Gly Asp Thr Tyr Tyr His Asp Tyr Phe
 50                  55                  60 gag ggc aag gcc aca ctg act gca gac aaa tcc tcc agc aca gcg tac     240
Glu Gly Lys Ala Thr Leu Thr Ala Asp Lys Ser Ser Ser Thr Ala Tyr
 65                  70                  75                  80 atg gaa ctc cgc agc ctg aca tct gag gac tct gcg gtc tat ttc tgt     288
Met Glu Leu Arg Ser Leu Thr Ser Glu Asp Ser Ala Val Tyr Phe Cys
                85                  90                  95 gca aga ggg gac tat gcc gat gtc tgg ggc aca ggg acc acg gtc acc     336
Ala Arg Gly Asp Tyr Ala Asp Val Trp Gly Thr Gly Thr Thr Val Thr
            100                 105                 110 gtc tcc tca gcc aaa acg aca ccc cca tct gtc tat                     372
Val Ser Ser Ala Lys Thr Thr Pro Pro Ser Val Tyr
        115                 120

<210> SEQ ID NO 72
<211> LENGTH: 124
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu His Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
            20                  25                  30

```
Gly Ile Ser Trp Val Lys Gln Arg Thr Gly Gln Gly Leu Glu Trp Ile
        35                  40                  45

Gly Glu Val Tyr Pro Arg Ser Gly Asp Thr Tyr Tyr His Asp Tyr Phe
 50                  55                  60

Glu Gly Lys Ala Thr Leu Thr Ala Asp Lys Ser Ser Thr Ala Tyr
 65                  70                  75                  80

Met Glu Leu Arg Ser Leu Thr Ser Glu Asp Ser Ala Val Tyr Phe Cys
                85                  90                  95

Ala Arg Gly Asp Tyr Ala Asp Val Trp Gly Thr Gly Thr Val Thr
            100                 105                 110

Val Ser Ser Ala Lys Thr Thr Pro Pro Ser Val Tyr
        115                 120
```

<210> SEQ ID NO 73
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 73

```
gac att gtg ctg aca cag tct cct gct tcc tta gct gta tct ctg ggg      48
Asp Ile Val Leu Thr Gln Ser Pro Ala Ser Leu Ala Val Ser Leu Gly
 1               5                  10                  15 cag agg gcc acc atc tca tgc agg gcc agc aaa agt gtc agt aca ttt      96
Gln Arg Ala Thr Ile Ser Cys Arg Ala Ser Lys Ser Val Ser Thr Phe
            20                  25                  30 ggc aat agt tat atg ctc tgg tac caa cag aaa cca gga cag cca ccc     144
Gly Asn Ser Tyr Met Leu Trp Tyr Gln Gln Lys Pro Gly Gln Pro Pro
        35                  40                  45 aaa ctc ctc atc tat ctt gca tcc aac cta gaa tct ggg gtc cct gcc     192
Lys Leu Leu Ile Tyr Leu Ala Ser Asn Leu Glu Ser Gly Val Pro Ala
 50                  55                  60 agg ttc agt ggc agt ggg tct ggg aca gac ttc acc ctc aac atc cat     240
Arg Phe Ser Gly Ser Gly Ser Gly Thr Asp Phe Thr Leu Asn Ile His
 65                  70                  75                  80 cct gtg gag gag gag gat gct gca acc tat tac tgt cag aac agt agg     288
Pro Val Glu Glu Glu Asp Ala Ala Thr Tyr Tyr Cys Gln Asn Ser Arg
                85                  90                  95 gag ctt ccg tac acg ttc gga ggg ggg acc aag ctg gaa ata aaa cgg     336
Glu Leu Pro Tyr Thr Phe Gly Gly Gly Thr Lys Leu Glu Ile Lys Arg
            100                 105                 110 gct gat gct gca cca                                                  351
Ala Asp Ala Ala Pro
        115
```

<210> SEQ ID NO 74
<211> LENGTH: 117
<212> TYPE: PRT
<213> ORGANISM: Artificial Sequence
<220> FEATURE:
<223> OTHER INFORMATION: Synthetic Construct

<400> SEQUENCE: 74

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Phe
```

-continued

```
                20                  25                  30
Gly Asn Ser Tyr Met Leu Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Asn Ser Arg
                85                  90                  95

Glu Leu Pro Tyr Thr Phe Gly Gly Gly Thr Lys Leu Glu Ile Lys Arg
            100                 105                 110

Ala Asp Ala Ala Pro
            115

<210> SEQ ID NO 75
<211> LENGTH: 389
<212> TYPE: PRT
<213> ORGANISM: Homo sapiens

<400> SEQUENCE: 75

Met Gly Tyr Pro Glu Val Glu Arg Arg Glu Leu Leu Pro Ala Ala Ala
 1               5                  10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
            35                  40                  45

Leu Ser Leu Ala Leu His Leu Leu Thr Leu Cys Cys Tyr Leu Glu Leu
 50                  55                  60

Arg Ser Glu Leu Arg Arg Glu Arg Gly Ala Glu Ser Arg Leu Gly Gly
 65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
            115                 120                 125

Asp Gly His Gln Met Ala Leu Leu Asn Phe Phe Phe Pro Asp Glu Lys
130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
            195                 200                 205

Pro Gly Thr Thr Val Met Gly Pro Pro Gly Pro Pro Gly Pro Pro Gly
            210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270
```

Asp Trp Ser Arg Ile Thr Met Asn Pro Lys Val Phe Lys Leu His Pro
            275                 280                 285

Arg Ser Gly Glu Leu Glu Val Leu Val Asp Gly Thr Tyr Phe Ile Tyr
            290                 295                 300

Ser Gln Val Tyr Tyr Ile Asn Phe Thr Asp Phe Ala Ser Tyr Glu Val
305                 310                 315                 320

Val Val Asp Glu Lys Pro Phe Leu Gln Cys Thr Arg Ser Ile Glu Thr
                325                 330                 335

Gly Lys Thr Asn Tyr Asn Thr Cys Tyr Thr Ala Gly Val Cys Leu Leu
            340                 345                 350

Lys Ala Arg Gln Lys Ile Ala Val Lys Met Val His Ala Asp Ile Ser
            355                 360                 365

Ile Asn Met Ser Lys His Thr Thr Phe Phe Gly Ala Ile Arg Leu Gly
            370                 375                 380

Glu Ala Pro Ala Ser
385

<210> SEQ ID NO 76
<211> LENGTH: 297
<212> TYPE: PRT
<213> ORGANISM: Homo sapiens

<400> SEQUENCE: 76

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45

Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
            115                 120                 125

Ala Pro Thr Val Pro Pro Gln Glu Ala Thr Leu Val Ala Leu Val Ser
        130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Val Ser Glu Asn Ile
            195                 200                 205

Phe Gln Thr Gln Pro Leu Asn Pro Ile Leu Glu Asp Asp Cys Ser Ser
        210                 215                 220

Thr Ser Gly Phe Pro Thr Gln Glu Ser Phe Thr Met Ala Ser Cys Thr
225                 230                 235                 240

Ser Glu Ser His Ser His Trp Val His Ser Pro Ile Glu Cys Thr Glu
                245                 250                 255

```
Leu Asp Leu Gln Lys Phe Ser Ser Ser Ala Ser Tyr Thr Gly Ala Glu
            260                 265                 270
Thr Leu Gly Gly Asn Thr Val Glu Ser Thr Gly Asp Arg Leu Glu Leu
            275                 280                 285
Asn Val Pro Phe Glu Val Pro Ser Pro
    290                 295
```

ANTI-ECTODYSPLASIN ANTIBODIES

REFERENCE TO RELATED APPLICATIONS

This application is a 35 U.S.C. §371 U.S. National Stage Entry of International Application No. PCT/US2014/028048 filed Mar. 14, 2014, which claims priority of U.S. Provisional Application Ser. Nos.: 61/903,165 filed Nov. 12, 2013, and 61/787,166 filed Mar. 15, 2013; the contents of each of which are incorporated herein by reference in their entireties.

REFERENCE TO SEQUENCE LISTING

The present application is being filed along with a Sequence Listing in electronic format. The Sequence Listing is provided as a file entitled 2003-1004US371SEQLST.txt created on Sep. 14, 2015 which is 61,961 bytes in size. The information in electronic format of the sequence listing is incorporated herein by reference in its entirety.

FIELD OF THE INVENTION

The present invention concerns the preparation of substantially purified monoclonal antibodies against ectodysplasin A1 (EDA1), as well as isolated monoclonal antibody fragments or antigen binding portions or fragments thereof. The invention further relates to isolated antagonist anti-EDA1 monoclonal antibodies or isolated monoclonal antibody fragments or antigen binding portions or fragments thereof as well as their use in immunoassays. The immunoassays may be used in methods for characterizing pharmacokinetic and/or pharmacodynamic profiles during administration of recombinant EDA1 for treatments of disorders arising from a lack of EDA1 action. The isolated antagonist anti-EDA1 monoclonal antibodies or isolated monoclonal antibody fragments or antigen binding portions or fragments thereof are provided in pharmaceutical compositions for the treatment of conditions potentially related to excessive EDA1 activity, such as sebaceous gland hyperplasia, hyperhidrosis, hirsutism, or certain types of cancers such as breast cancer and dermal eccrine cylindroma. Finally, the present invention concerns a kit comprising the isolated antagonist anti-EDA1 monoclonal antibodies or isolated monoclonal antibody fragments or antigen binding portions or fragments thereof.

BACKGROUND OF THE INVENTION

An activator protein known as ectodysplasin isoform A1, (EDA-A1, hereinafter referred to as EDA1) is required for normal development of several ectodermally-derived organs in humans and mice. This influence on normal development is executed through the action of EDA1 binding to its receptor EDAR.

The ectodysplasin gene (EDA) codes for 2 protein splice isoforms, EDA1 and EDA2, which differ by the absence of Val207 and Glu308 in EDA2, a difference sufficient to specify binding and activation of two different receptors, EDA1 receptor (EDAR) and X-linked EDA1 receptor (XEDAR), respectively as detailed in "The anhidrotic ectodermal dysplasia gene (EDA) undergoes alternative splicing and encodes ectodysplasin-A with deletion mutations in collagenous repeats" Bayés M et al. Hum Mol Genet. 1998 October; 7(11):1661-9 and "Two-amino acid molecular switch in an epithelial morphogen that regulates binding to two distinct receptors" Yan M et al. Science. 2000 Oct. 20; 290(5491):523-7 the contents of which are incorporated herein by reference in their entireties.

The discovery and descriptions of EDA2 include those described in detail in U.S. Pat. No. 5,700,926 filed Jul. 22, 1996 which is a continuation of U.S. Pat. No. 5,556,786 filed Apr. 27, 1993, the contents of which are incorporated herein by reference in their entireties. The discovery and descriptions of XEDAR include PCT application PCT/US2000/009699 now granted patents EP1169448B1 filed May 8, 2013, U.S. Pat. No. 6,534,061 filed Apr. 12, 2000, and U.S. Pat. No. 7,198,913 filed Sep. 12, 2002 the contents of which are incorporated herein by reference in their entireties. Additionally, descriptions of multimeric TNF receptors are included in international application PCT/EP2009/057396 filed Jun. 15, 2009.

The EDA1 receptor is referred to as EDAR and the EDA2 receptor is referred to as XEDAR. EDA1 and EDA2 belong to the tumor necrosis factor (TNF) family as classified by the expression of a TNF homology domain. The TNF homology domain of EDA1 (from Gln247 to Ser391) and EDA2 (from Gln247 to Ser389) is more conserved than that of any other TNF family members, with human EDA being 100% and 98% identical to mouse and chicken EDA, respectively.

EDAR and XEDAR regulate aspects of ectodermal development by activation of NF-κB signaling pathways. The EDA1-EDAR axis plays a predominant role in the development of skin-derived structures, including hair and sebaceous glands. EDA2 and XEDAR are less well defined, but may play a role in myodegeneration, hypohidrotic dysplasia, and androgenic alopecia. XEDAR is closely related to the orphan receptor TROY. Based on a careful sequence analysis of EDA, EDAR, XEDAR, and TROY in various species, it has been hypothesized that TROY might be the receptor for EDA2 in vertebrates, with the exception of marsupials and mammals, where the specificity of EDA2 would have shifted to XEDAR.

Efforts to treat developmental diseases have focused on improvement of the interaction between EDA1 and EDAR. One of these approaches is the use of recombinant proteins containing the receptor-binding domain of EDA1 fused to the C-terminus of an IgG1 Fc domain. The publication "Permanent correction of an inherited ectodermal dysplasia with recombinant EDA", O. Gaide et al., *Nature Med.*, 2003, 9(5), 614-618, describes the administration of recombinant EDA1 to developing embryos and newborn Tabby mice in order to correct the phenotype and provide a basis for a possible treatment of XLHED.

Such an approach is also described in US Patent 2005152872 (Gaide et al.), which is incorporated herein by reference in entirety. In particular this document discloses a recombinant fusion protein containing an amino-acid sequence which comprises: (a) the Fc section or part of an Fc section of an immunoglobulin as component (A) or a functional variant of component (A); (b) the extracellular part of a TNF ligand or a partial sequence of the extracellular part of a TNF ligand as component (B) or a functional variant of component (B); and optionally (c) a transition area between component (A) and component (B), containing a linker.

PCT publication number WO2010113117, which is incorporated herein by reference in entirety, describes agonist anti-EDAR antibodies as another approach for treating developmental disorders. The process of improving the action of EDAR by providing agonists is used to counteract the poor interactions between EDA1 and EDAR that lead to developmental disorders.

In contrast to the developmental disorders arising from poor interactions between EDA1 and EDAR, a number of other disorders of varying severity are postulated to arise from excessive action of EDA1. Such conditions include hirsutism (excessive hair growth), ectopic teeth and/or excessive growth of teeth, hyperhidrosis (excessive sweating), sebaceous gland hyperplasia, breast cancer, dermal eccrine cylindroma, and skin conditions arising from overactive sebaceous glands, such as sebaceous gland hyperplasia, comedones, milia, acne, seborrhea, rosacea, steatoma, or furuncles.

There is a need to provide treatments for conditions arising from excessive action of EDA1. There is also a need to provide assays for quantitation of EDA1 and which facilitate characterization of pharmacokinetic and/or pharmacodynamic profiles of individuals being treated with recombinant EDA1 for developmental disorders arising from a lack of action of EDA1. The present invention addresses these needs.

SUMMARY OF THE INVENTION

One aspect of the invention is an isolated monoclonal antibody or isolated monoclonal antibody fragment or antigen binding portion or fragment thereof, that binds human and/or mouse and/or avian EDA1, the antibody comprising:
(a) a heavy chain variable region comprising the complementary determining region (CDR) amino acid sequences: SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; and/or
(b) a light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18.

Another aspect of the invention is an isolated monoclonal antibody or isolated monoclonal antibody fragment or antigen binding portion or fragment thereof, that binds human and/or mouse and/or avian EDA1, the antibody comprising a heavy chain variable region and a light chain variable region, wherein the heavy chain variable region comprises an amino acid sequence selected from the group consisting of: SEQ ID NO: 51, 53 and 55; amino acid sequences that differ from those sequences SEQ ID NO: 51, 53 and 55 by 1, 2, 3, 4, 5, 6, 7, 8, 9, or 10 conservative amino acid substitutions; and amino acid sequences having at least 95% sequence identity to the sequences specified.

Another aspect of the invention is an isolated monoclonal antibody or isolated monoclonal antibody fragment or antigen binding portion or fragment thereof, that binds human and/or mouse and/or avian EDA1, the antibody comprising a light chain variable region and a heavy chain variable region, wherein the light chain variable region comprises an amino acid sequence selected from the group consisting of: (a) SEQ ID NO: 52, 54 and 56; (b) amino acid sequences that differ from those sequences specified in (a) by 1, 2, 3, 4, 5, 6, 7, 8, 9, or 10 conservative amino acid substitutions; and (c) amino acid sequences having at least 95% sequence identity to the sequences specified in (a) or (b).

Another aspect of the invention is an isolated nucleic acid molecule encoding an isolated monoclonal antibody or isolated monoclonal antibody fragment or antigen binding portion or fragment thereof as described herein.

Another aspect of the invention is an expression vector comprising at least one copy of the nucleic acid molecule as described herein.

Another aspect of the invention is a host cell comprising the expression vector as described herein.

Another aspect of the invention is a transgenic non-human animal having a genome comprising the isolated nucleic acid molecule as described herein and/or the expression vector as described herein.

Another aspect of the invention is a hybridoma secreting isolated monoclonal antibody or isolated monoclonal antibody fragment or antigen binding portion or fragment thereof as described herein.

Another aspect of the invention is a kit for performing an immunoassay, the kit comprising the isolated monoclonal antibody or isolated monoclonal antibody fragment or antigen binding portion or fragment thereof as described herein or the isolated nucleic acid molecule as described herein.

Another aspect of the invention is a method of characterizing a pharmacokinetic profile and/or a pharmacodynamic profile of a recombinant EDA1 molecule, the method comprising:
a) obtaining samples from a patient at a plurality of time points after administration of the recombinant EDA1; and
b) determining the quantity of recombinant EDA1 at the time points using an immunoassay comprising an antibody generated against the recombinant EDA1, thereby characterizing the pharmacokinetic profile of the recombinant EDA1 molecule.

Another aspect of the invention is a method of treating a patient with a developmental disorder, the method comprising:
a) administering recombinant EDA1 to the patient;
b) characterizing a pharmacokinetic profile and/or a pharmacodynamic profile according to the method described herein;
c) selecting a dosing regimen for recombinant EDA1 based upon the characterized pharmacokinetic profile; and
d) treating the patient according to the selected dosing regimen.

Another aspect of the invention is a method for producing anti-EDA1 monoclonal antibodies or isolated monoclonal antibody fragments or antigen binding portions or fragments thereof comprising the steps of:
a) producing EDA1 antigen, or EDA1 fragment, or EDA1 fusion protein of mouse and/or human and/or vertebrate species;
b) immunizing EDA1-deficient mice with said EDA1 antigen or EDA1 fragment, or EDA1 fusion protein;
c) detecting anti-EDA1 antibodies in the serum of said EDA1 antigen or EDA1 fragment, or EDA1 fusion protein-immunized EDA1-deficient mice;
d) producing hybridomas between lymph node cells from EDA1 antigen or EDA1 fragment, or EDA1 fusion protein-immunized, EDA1-deficient mice and myeloma cells;
e) identifying anti-EDA1 antibodies or isolated monoclonal antibody fragments or antigen binding portions or fragments thereof recognizing human and/or mouse and/or avian EDA1 and/or EDA1 from vertebrate species i. by binding assays designed to detect binding between the antagonist anti-EDA1 antibodies or isolated monoclonal antibody fragments or antigen binding portions or fragments thereof and human and/or mouse and/or avian EDA1 antigen or EDA1 fragment, or EDA1 fusion protein; ii. for their ability to block binding of recombinant EDA1 to recombinant EDAR in an in vitro assay; iii. for their ability to inhibit the response induced by EDA1 in cells expressing an EDAR:Fas fusion protein in vitro; iv. for their ability to block the biological response induced by recombinant EDA1 in EDA-deficient mice; and v. for their ability to induce a biological response in vivo in organisms expressing EDA1 characterized by the effect of EDA1 inhibition;

f) selecting hybridoma lines for the antagonist anti-EDA1 monoclonal antibodies produced by the hybridoma lines on the basis of the results of steps e) ii and e) iii;

g) cloning and sub-cloning the selected hybridoma lines; and h) purifying the resulting antagonist anti-EDA1 monoclonal antibodies or isolated monoclonal antibody fragments or antigen binding portions or fragments thereof.

Another aspect of the invention is a pharmaceutical composition comprising isolated monoclonal antibody or isolated monoclonal antibody fragment or antigen binding portion or fragment thereof as described herein, and a pharmaceutically acceptable carrier.

In certain embodiments, the pharmaceutical composition is used to treat hirsutism, ectopic teeth, hyperhidrosis, breast cancer, dermal eccrine cylindroma or a skin disorder selected from the group consisting of sebaceous gland hyperplasia, comedones, milia, acne, seborrhea, rosacea, steatoma, and furuncles.

Another aspect of the invention is a method of reducing the development of one or more structures or reducing the proliferation of cells in a subject in need thereof, the method comprising administering to the subject an anti-EDA monoclonal antibody or antigen-binding portion or fragment thereof that binds human and/or mouse EDA, wherein the one or more structures are selected from the group consisting of: hair follicles, teeth, sweat glands, sebaceous glands, larynx and trachea mucus-producing cells, meibomian glands, preputial glands, mammary glands, and salivary glands.

Another aspect of the invention is a method of detecting and/or quantifying EDA1 in serum comprising, performing pre-depletion of EDA1 in serum prior to performing a sandwich ELISA using EctoD2 as the capture antibody and EctoD3 as the detection antibody. The pre-depletion of said serum may be performed by incubating said serum with EDA binding agents and EDA non-binding agent.

BRIEF DESCRIPTION OF THE FIGURES

Figure 27:
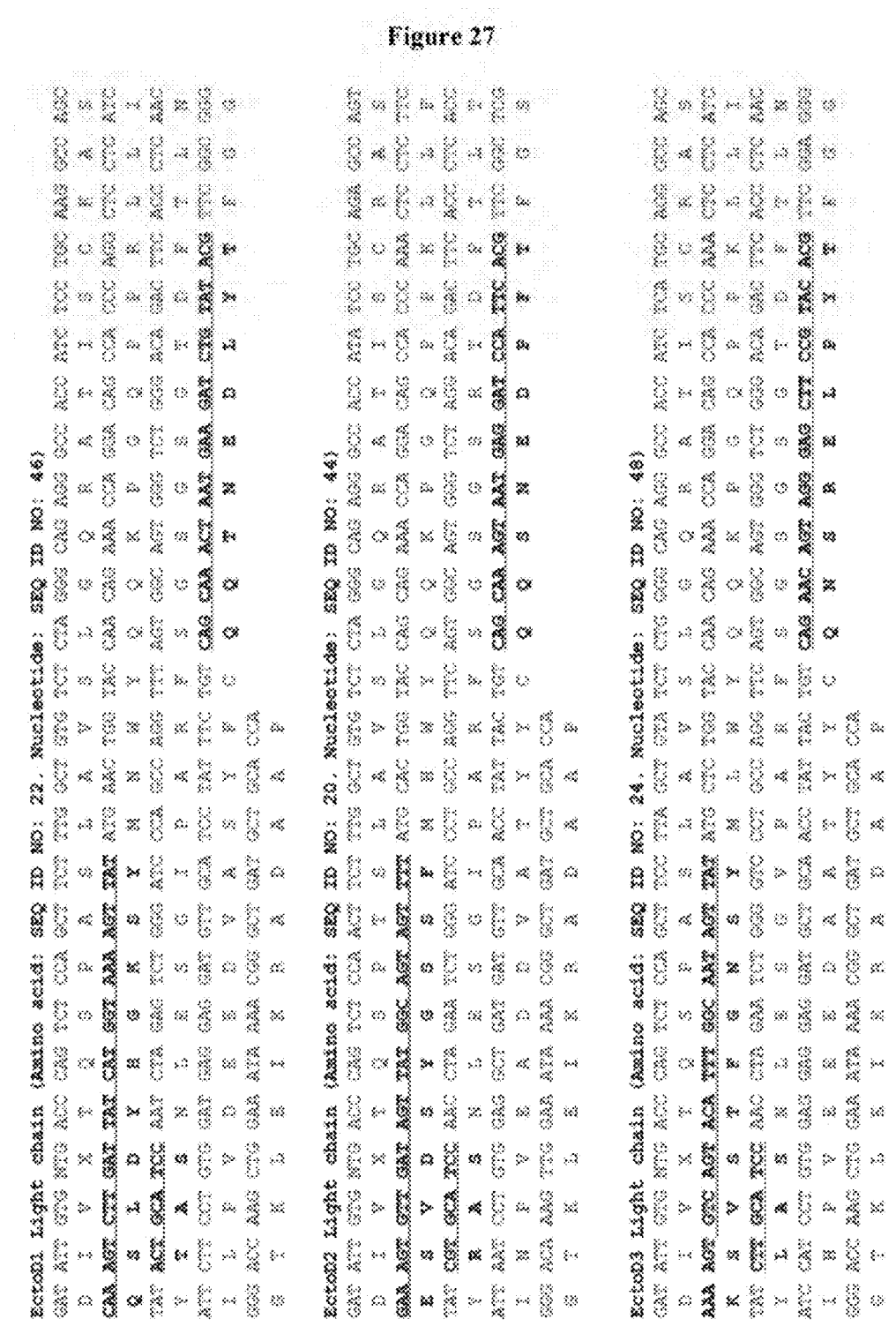

FIG. 27. Amino acid and nucleotide sequences of the light chains of mAbEDA1-EctoD1, mAbEDA1-EctoD2, and mAbEDA1-EctoD3.

Figure 28:
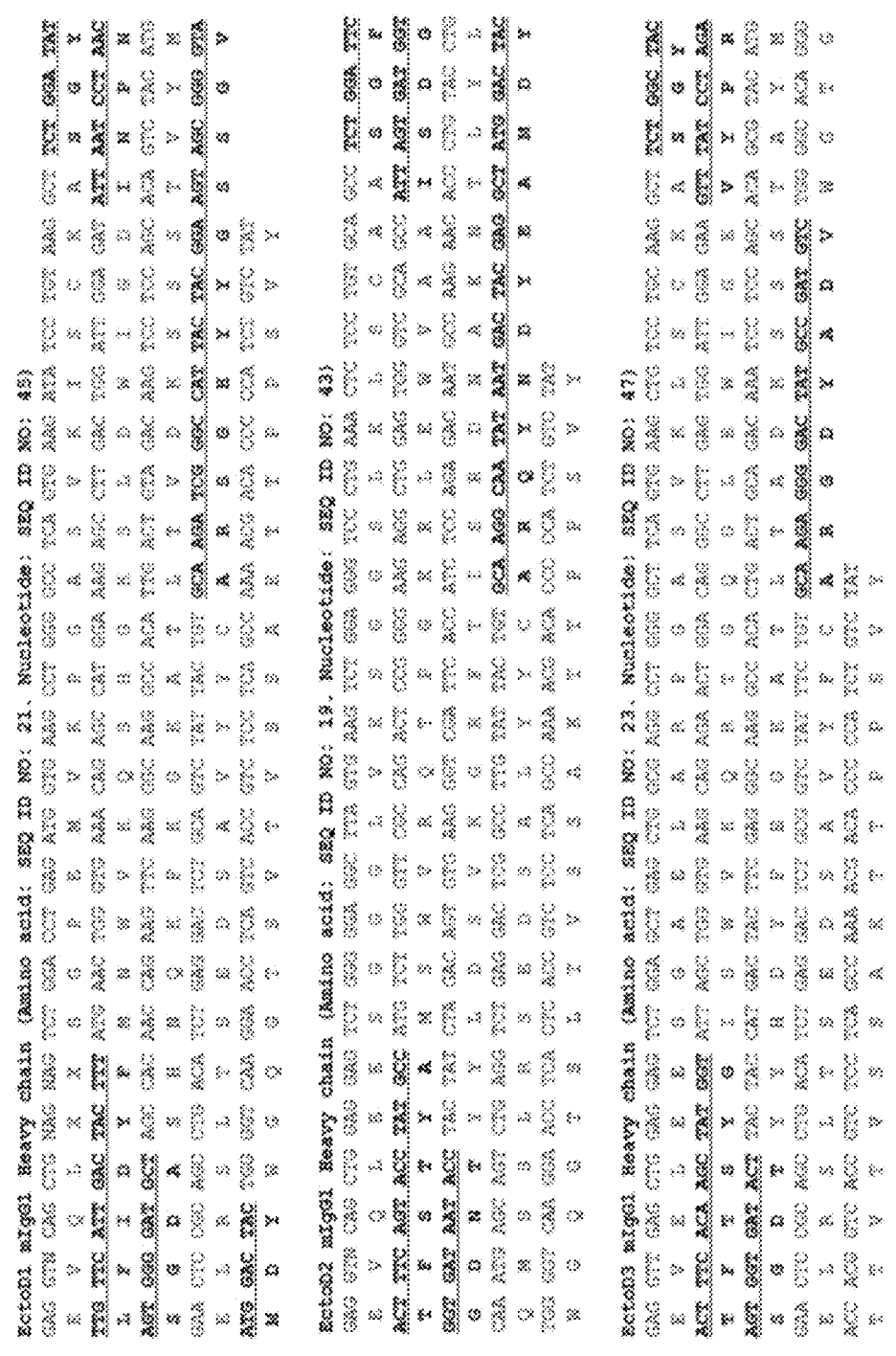

FIG. 28. Amino acid and nucleotide sequences of the heavy chains of mAbEDA1-EctoD1, mAbEDA1-EctoD2, and mAbEDA1-EctoD3.

FIG. 30. Amino acid and nucleotide sequences, re-amplified using degenerate primers in the signal peptides, of the light chains of mAbEDA1-EctoD1, mAbEDA1-EctoD2, and mAbEDA1-EctoD3.

FIG. 31. Amino acid and nucleotide sequences, re-amplified using degenerate primers in the signal peptides, of the heavy chains of mAbEDA1-EctoD1, mAbEDA1-EctoD2, and mAbEDA1-EctoD3.

SEQUENCE LISTING

Figure 1:
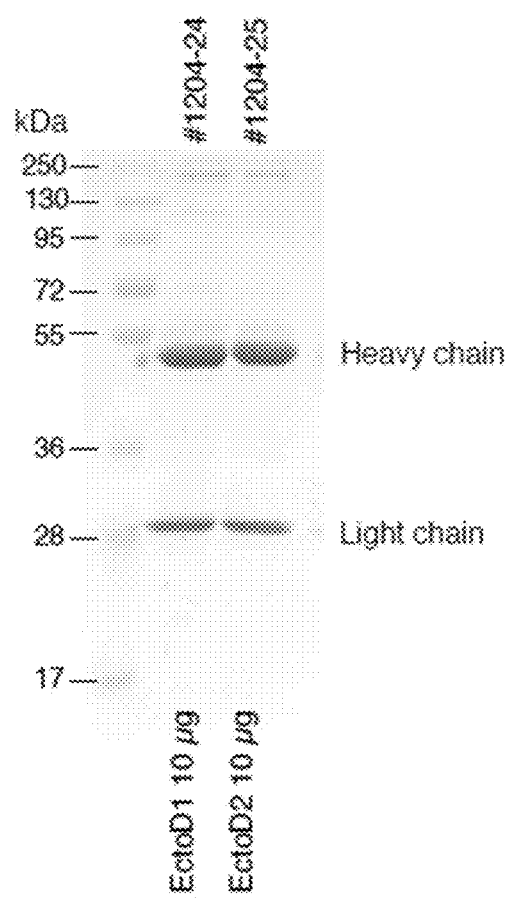
FIG. 1. Results of an SDS-PAGE analysis of mAbEDA1-EctoD1 and mAbEDA1-EctoD2.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NOs: 51-56 and SEQ ID NOs: 57-62 are re-amplified sequences for SEQ ID NOs: 19-24 and SEQ ID NOs: 43-48 respectively, using degenerate primers in the signal peptides.

SEQ ID NOs: 1-18 show the amino acid sequences of the complementarity determining regions (CDRs) CDR1, CDR2 and CDR3 of the heavy chains and light chains of three anti-EDA1 monoclonal antibodies, namely mAbEDA1-EctoD1, mAbEDA1-EctoD2 and mAbEDA1-EctoD3 (see Table 1).

SEQ ID NOs: 19-24 show the amino acid sequences of the heavy and light chains of three anti-EDA1 monoclonal antibodies, namely mAbEDA1-EctoD1, mAbEDA1-EctoD2 and mAbEDA1-EctoD3 (see Table 2).

SEQ ID NOs: 25-42 show the nucleotide sequences of the CDR1, CDR2 and CDR3 of the heavy chains and light chains of three anti-EDA1 monoclonal antibodies, namely mAbEDA1-EctoD1, mAbEDA1-EctoD2 and mAbEDA1-EctoD3 (see Table 3).

SEQ ID NOs: 43-48 show the nucleotide sequences of the heavy and light chains of three anti-EDA1 monoclonal antibodies, namely mAbEDA1-EctoD1, mAbEDA1-EctoD2 and mAbEDA1-EctoD3 (see Table 4).

SEQ ID NO: 49 is the sequence of human (*Homo sapiens*) EDA1 of GenBank Accession No. AAI26144.1.

SEQ ID NO: 50 is the sequence of mouse (*Mus musculus*) EDA1 of GenBank Accession No. CAB52696.1.

SEQ ID NOs: 51-56 show the amino acid sequences of the heavy and light chains of three anti-EDA1 monoclonal antibodies, namely mAbEDA1-EctoD1, mAbEDA1-EctoD2 and mAbEDA1-EctoD3 (see Table 2).

SEQ ID NOs: 57-62 show the nucleotide sequences of the heavy and light chains of three anti-EDA1 monoclonal antibodies, namely mAbEDA1-EctoD1, mAbEDA1-EctoD2 and mAbEDA1-EctoD3 (see Table 4).

SEQ ID NO: 63 is the sequence of human (*Homo sapiens*) EDA2 of GenBank Accession No. AAI44052.1

SEQ ID NO: 64 is the sequence of mouse (*Homo sapiens*) EDA2 receptor (XEDAR) of GenBank Accession No. AAH34919.1

DETAILED DESCRIPTION OF THE INVENTION

General Definitions

As used herein, the following general definitions are supplied in order to facilitate the understanding of the present invention. Additional definitions are provided hereinbelow in context of certain embodiments of the invention.

"A" or "an" means "at least one" or "one or more."

The term "comprise" is generally used in the sense of include, that is to say permitting the presence of one or more features or components.

As used herein, the terms "protein," "polypeptide," "polypeptidic," "peptide" and "peptidic" or "peptidic chain" are used interchangeably herein to designate a series of amino acid residues connected to the other by peptide bonds between the alpha-amino and carboxy groups of adjacent residues.

"Amino acid residue" means any amino acid residue known to those skilled in the art. This encompasses naturally occurring amino acids (including for instance, using the three-letter code, Ala, Arg, Asn, Asp, Cys, Gln, Glu, Gly, His, Ile, Leu, Lys, Met, Phe, Pro, Ser, Thr, Trp, Tyr, Val), as well as rare and/or synthetic amino acids and derivatives thereof (including for instance Aad, Abu, Acp, Ahe, Aib, Apm, Dbu, Des, Dpm, Hyl, McLys, McVal, Nva, and the like).

The amino acid residue or derivative thereof can be any isomer, especially any chiral isomer, e.g. the L- or D-isoform.

By "amino acid derivative," it is meant any amino acid derivative as known in the art. For instance, amino acid derivatives include residues derivable from natural amino acids bearing additional side chains, e.g. alkyl side chains, and/or heteroatom substitutions.

The term "purified" does not require absolute purity; rather, it is intended as a relative term. Thus, for example, a purified anti-EDA1 monoclonal antibody preparation is one in which the protein is more pure than the protein in its natural environment within a cell. In some embodiments, a preparation of an anti-EDA1 monoclonal antibody is purified such that the protein represents at least 50% of the total protein content of the preparation.

As used herein, the expression "substantially pure" refers to material that is at least 90% pure, at least 95% pure, at least 98% pure or 99% pure, or with greater purity.

An "isolated antibody", as used herein, is intended to refer to an antibody which is substantially free of other antibodies having different antigenic specificities (e. g., an isolated antibody that specifically binds to EDA1 is substantially free of antibodies that specifically bind antigens other than EDA1). An isolated antibody that specifically binds to an epitope, isoform or variant of human EDA1 may, however, have cross-reactivity to other related antigens, e. g., from other species (e.g., EDA1 species homologues or splice isoform (EDA2). Moreover, an isolated antibody may be substantially free of other cellular material and/or chemicals. In one embodiment of the invention, a combination of "isolated" monoclonal antibodies having different specificities are combined in a well-defined composition.

"Disease," as used herein, refers to a pathological condition of a part, organ, or system of an organism resulting from various causes, such as infection, genetic defect, or environmental stress, and characterized by an identifiable group of signs or symptoms.

The term "subject" refers to patients of human or other vertebrates, in particular mammals, and includes any individual it is desired to examine or treat using the methods according to the present invention. However, it will be understood that "patient" does not automatically imply that symptoms or diseases are present. In some embodiments, the term "patient" refers to a human in need of treatment for a disorder arising from excessive activity of EDA1.

"Mammal" for purposes of treatment refers to any animal classified as a mammal, including humans, domestic and farm animals, and zoo, sports, or pet animals, such as dogs, horses, cats, cows, monkeys etc. In some embodiments, the mammal is a human.

"Treatment" refers to both therapeutic treatment and prophylactic or preventive measures. Those in need of treatment include those already with the disorder as well as those in which the disorder is to be prevented. Hence, the mammal to be treated herein may have been diagnosed as having the disorder or may be predisposed or susceptible to the disorder. Thus the term "treatment" or "treating" herein encompasses curative treatment, preventive treatment as well as palliative treatment, more specifically palliative treatment and curative treatment. For the purpose of this invention, the "treatment" is an approach for obtaining beneficial results including, but not limited to, one or more of the following: reducing or totally destroying of the symptoms of a disorder and decreasing the frequency of mortality of patients.

The term "antigen" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes.

The term "antibody", as used herein, refers to a protein produced by the immune system that protects the organism against an antigen. But, as used herein, the term encompasses not only intact monoclonal antibodies but also fragments thereof, single chains, mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity. An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4.

The variable regions of the heavy and light chains contain a binding domain that interacts with an antigen. The constant regions of the antibodies may mediate the binding of the immunoglobulin to host tissues or factors, including various cells of the immune system (e. g., effector cells) and the first component (C1q) of the classical complement system.

The terms "monoclonal antibody" (mAb) or "monoclonal antibody composition" as used herein refer to a preparation of antibody molecules of single molecular composition. A monoclonal antibody composition displays a single binding specificity and affinity for a particular epitope. The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics.

The phrases "an antibody recognizing an antigen" and "an antibody specific for an antigen" are used interchangeably herein with the term "an antibody which binds specifically to an antigen."

The term "antigen-binding portion" of an antibody (or simply "antibody portion"), as used herein, refers to one or more fragments of an intact antibody that retain the ability to specifically bind to an antigen (for example, an antigen of EDA1). It has been shown that the antigen-binding function of an antibody can be performed by fragments of a full-length antibody. Examples of binding include (i) a Fab fragment, a monovalent fragment consisting of the VL, VH, CL and CH1 domains; (ii) a F (ab)' 2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341: 544-546), which consists of a VH domain; and (vi) an isolated complementarity determining region (CDR); and (vii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Huston et al. (1988) Proc. Natl. Acad. Sci USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

"Fragments" refer to sequences sharing at least 40% amino acids in length with the respective sequence of the intact or full length antagonist anti-EDA1 monoclonal antibodies (native). These sequences can be used as long as they exhibit the same properties as the native sequence from which they are derived. In some embodiments, these sequences share more than 70%, more than 80%, or more than 90% amino acids in length with the respective sequence the intact or full length anti-EDA1 monoclonal antibodies.

In the case of an anti-EDA1 monoclonal antibody of the invention, useful fragments include, but are not limited to: a CDR region, especially a CDR3 region of the heavy or light chain; a variable domain of a heavy or light chain; a portion of an antibody chain or just its variable region including two CDRs; and the like. Suitable anti-EDA1 monoclonal antibody fragments of the invention are immunologically functional immunoglobulins. The term "immunologically functional immunoglobulin fragment" as used herein refers to a polypeptide fragment that contains at least the CDRs of the immunoglobulin heavy and light chains. In some embodiments, an immunologically functional immunoglobulin fragment of the invention is capable of specifically binding to EDA1.

In some embodiments, the fragment binds specifically to EDA1 in an immunoassay used for the purpose of confirming the presence of and/or quantifying the amount of EDA1 in a biological sample.

The term "immunoassay" refers to a test that uses the binding of antibodies to antigens to identify and measure certain substances Immunoassays often are used to diagnose disease, and test results can provide information about a disease that may help in planning treatment. An immunoassay takes advantage of the specific binding of an antibody to its antigen. Monoclonal antibodies are often used as they usually bind only to one site of a particular molecule, and therefore provide a more specific and accurate test, which is less easily confused by the presence of other molecules. The antibodies used must have a high affinity for the antigen of interest, because a very high proportion of the antigen must bind to the antibody in order to ensure that the assay has adequate sensitivity.

The term "enzyme linked immunosorbent assay" or abbreviated "ELISA" as used herein refers to a technique for the detecting antigens (e.g., proteins) in a biological sample. ELISA is a technique well known to those skilled in the art. The skilled person provided with specific antibodies is able to develop ELISA for detection of the antibody target without undue experimentation. ELISA techniques are described in more detail hereinbelow.

Isolated Anti-EDA1 Monoclonal Antibodies, Variants, Fragments and Modifications Thereof Certain aspects of the invention provide isolated anti-EDA1 monoclonal antibodies or isolated monoclonal antibody fragments or antigen binding portions or fragments thereof obtainable by the above-described process and wherein said isolated anti-EDA1 monoclonal antibodies or isolated monoclonal antibody fragments or antigen binding portions or fragments thereof bind to human and/or mouse and/or avian EDA1 and/or recombinant EDA1 (including, for example, Fc-EDA1) with an affinity constant (KD) of at least $10^{-8}$ M for the Fab fragment. The specific binding according to the invention presents a high affinity. In addition, the isolated anti-EDA1 monoclonal antibodies or isolated monoclonal antibody fragments or antigen binding portions or fragments thereof that cross-react with mouse EDA1 reduce guard hair formation and/or reduce retroauricular hair formation and/or disrupt functional sweat glands and/or reduce fur upon administration to developing wild-type mice (e.g. by repeated ip or iv administration of the antibody in pregnant mice, followed by repeated administration of the antibody in the newborn pups).

As used herein, "specific binding" refers to antibody binding to a predetermined antigen. Typically, the antibody binds with an affinity constant (KD) of $10^{-8}$ M or less for the Fab fragment, and binds to the predetermined antigen with a KD that is at least ten-fold less than its KD for binding to a non-specific antigen (e. g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "Kassoc" or "Ka", as used herein, is intended to refer to the association rate of a particular antibody-antigen interaction, whereas the term "KdiS" or "Kd" is intended to refer to the dissociation rate of a particular antibody-antigen interaction. The term "high affinity" for an IgG antibody refers to an affinity constant (KD) for the Fab fragment of at least about $10^{-8}$ M, at least about $10^{-9}$ M, at least about $10^{-10}$ M, at least about $10^{-11}$ M, or at least about $10^{-12}$ M or greater, e. g., up to $10^{-13}$ M or $10^{-14}$ M or greater. However, "high affinity" binding can vary for other antibody isotypes.

In certain embodiments, the isolated anti-EDA1 monoclonal antibodies or isolated monoclonal antibody fragments or antigen binding portions or fragments thereof, that specifically bind human and mouse EDA1, comprise: a heavy chain variable region comprising the complementary determining region amino acid sequences of SEQ ID NO: 1, SEQ ID NO: 2, SEQ ID NO: 3, or SEQ ID NO: 7, SEQ ID NO: 8, SEQ ID NO: 9, or SEQ ID NO: 13, SEQ ID NO: 14, SEQ ID NO: 15 and a light chain variable region comprising the complementary determining region amino acid sequences of SEQ ID NO: 4, SEQ ID NO: 5, SEQ ID NO: 6 or SEQ ID NO: 10, SEQ ID NO: 11, SEQ ID NO: 12, or SEQ ID NO: 16, SEQ ID NO: 17, SEQ ID NO: 18 and or combinations thereof and wherein said isolated monoclonal antibodies or isolated monoclonal antibody fragments or antigen binding portions or fragments thereof specifically bind to human and/or mouse and/or avian EDA1.

CDR amino acid sequences of anti-EDA1 monoclonal antibodies or isolated monoclonal antibody fragments or antigen binding portions or fragments thereof are shown in Table 1. The single letter amino acid code is used.

TABLE 1

Amino acid sequences of CDRs of anti-EDA monoclonal antibodies

| mAb | Chain | CDR | CDR Amino acid sequence | SEQ ID NO: |
|---|---|---|---|---|
| mAbEDA1-EctoD2 | Heavy | CDR1 | SGFTFSTYA | 1 |
| mAbEDA1-EctoD2 | Heavy | CDR2 | ISDGGDNT | 2 |

TABLE 1-continued

Amino acid sequences of CDRs of anti-EDA monoclonal antibodies

| mAb | Chain | CDR | CDR Amino acid sequence | SEQ ID NO: |
|---|---|---|---|---|
| mAbEDA1-EctoD2 | Heavy | CDR3 | ARQYNDYEAMDY | 3 |
| mAbEDA1-EctoD2 | Light | CDR1 | ESVDSYGSSF | 4 |
| mAbEDA1-EctoD2 | Light | CDR2 | RAS | 5 |
| mAbEDA1-EctoD2 | Light | CDR3 | QQSNEDPFT | 6 |
| mAbEDA1-EctoD1 | Heavy | CDR1 | SGYLFIDYF | 7 |
| mAbEDA1-EctoD1 | Heavy | CDR2 | INPNSGDA | 8 |
| mAbEDA1-EctoD1 | Heavy | CDR3 | ARSGHYYGSSGVMDY | 9 |
| mAbEDA1-EctoD1 | Light | CDR1 | QSLDYHGKSY | 10 |
| mAbEDA1-EctoD1 | Light | CDR2 | TAS | 11 |
| mAbEDA1-EctoD1 | Light | CDR3 | QQTNEDLYT | 12 |
| mAbEDA1-EctoD3 | Heavy | CDR1 | SGYTFTSYG | 13 |
| mAbEDA1-EctoD3 | Heavy | CDR2 | VYPRSGDT | 14 |
| mAbEDA1-EctoD3 | Heavy | CDR3 | ARGDYADV | 15 |
| mAbEDA1-EctoD3 | Light | CDR1 | KSVSTFGNSY | 16 |
| mAbEDA1-EctoD3 | Light | CDR2 | LAS | 17 |
| mAbEDA1-EctoD3 | Light | CDR3 | QNSRELPYT | 18 |

TABLE 2

Amino acid sequences of heavy and light chains of anti-EDA monoclonal antibodies

| mAb | Chain | SEQ ID NO: |
|---|---|---|
| mAbEDA1-EctoD2 | Heavy | 19 |
| mAbEDA1-EctoD2 | Light | 20 |
| mAbEDA1-EctoD1 | Heavy | 21 |
| mAbEDA1-EctoD1 | Light | 22 |
| mAbEDA1-EctoD3 | Heavy | 23 |
| mAbEDA1-EctoD3 | Light | 24 |
| mAbEDA1-EctoD2 | Heavy | 51 |
| mAbEDA1-EctoD2 | Light | 52 |
| mAbEDA1-EctoD1 | Heavy | 53 |
| mAbEDA1-EctoD1 | Light | 54 |
| mAbEDA1-EctoD3 | Heavy | 55 |
| mAbEDA1-EctoD3 | Light | 56 |

In some embodiments, the isolated antagonist anti-EDA1 monoclonal antibodies or isolated monoclonal antibody fragments or antigen binding portions or fragments thereof, comprise: a heavy chain variable region that comprises CDR1, CDR2, CDR3 sequences and a light chain variable region that comprises CDR1, CDR2, CDR3 sequences wherein: (a) the heavy chain variable region CDR1 sequence comprises the amino acid sequence of SEQ ID NOs: 1, 7 or 13 and conservative modifications thereof; (b) the heavy chain variable region CDR2 sequence comprises the amino acid sequence of SEQ ID NOs: 2, 8 or 14 and conservative modifications thereof; (c) the heavy chain variable region CDR3 sequence comprises the amino acid sequence of SEQ ID NOs: 3, 9 or 15 and conservative modifications thereof; (d) the light chain variable region CDR1 sequence comprises an amino acid sequence selected from the group consisting of amino acid sequences of SEQ ID NOs: 4, 10 or 16 and conservative modifications thereof; (e) the light chain variable region CDR2 sequence comprises an amino acid sequence selected from the group consisting of amino acid sequences of SEQ ID NOs: 5, 11 or 17, and conservative modifications thereof;

(f) the light chain variable region CDR3 sequence comprises an amino acid sequence selected from the group consisting of amino acid sequences of SEQ ID NOs: 6, 12 or 18, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. Conservative amino acid substitutions are herein defined as exchanges within one of the following five groups:

I. Small aliphatic, nonpolar or slightly polar residues: Ala, Ser, Thr, Pro, Gly II. Polar, positively charged residues: His, Arg, Lys III. Polar, negatively charged residues: and their amides: Asp, Asn, Glu, Gln IV. Large, aromatic residues: Phe, Tyr, Trp V. Large, aliphatic, nonpolar residues: Met, Leu, Ile, Val, Cys. (see, e.g., Creighton, Proteins (1984)).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides.

The isolated anti-EDA1 monoclonal antibodies are not limited to the whole molecule, and may be a fragment of the antibody or the modified product thereof, as long as they retain their ability to bind to EDA1 (or fragment or variant thereof).

Multivalent, bivalent and monovalent antibodies are included. Examples of fragments of an antibody include Fab, F(ab)'2, Fv, Fab/c having one Fab and a complete Fc, and a single chain Fv (scFv) wherein the Fv of the H-chain or the L-chain is ligated with an appropriate linker. Specifically, an antibody fragment is synthesized by treating the antibody with an enzyme such as papain, pepsin or ficin, or genes encoding these antibody fragments are constructed, the genes are introduced into expression vectors, and the genes are then expressed by appropriate host cells (see e g, Rousseaux, J et al., *Methods Enzymol.* (1989) 121, 663-669, and Bird, R E et al, *TIBTECH* (1991) 9, 132-137).

A fragment known to those in the art as scFv is obtained by linking the H-chain V-region and the L-chain V-region of antibodies. In the scFv, the H-chain V-region and the L-chain V-region are linked via a linker, or a peptide linker (Huston, J. S. et al., *Proc. Natl. Acad. Sci. U.S.A.* (1988) 85, 5879-5883). The H-chain V-region and the L-chain V-region in scFv may be derived from any of those described as antibodies in this specification. As a peptide linker to link the V-regions, for example, any single-stranded peptide comprising 12 to 19 amino acid residues is used.

In certain embodiments, the isolated antagonist anti-EDA1 monoclonal antibodies or isolated monoclonal antibody fragments or antigen binding portions or fragments thereof, consist of:

(a) a heavy chain variable region CDR1 comprising SEQ ID NO: 1, 7 or 13;

(b) a heavy chain variable region CDR2 comprising SEQ ID NO: 2, 8 or 14;

(c) a heavy chain variable region CDR3 comprising SEQ ID NO: 3, 9 or 15;

(d) a light chain variable region CDR1 comprising SEQ ID NO: 4, 10 or 16;

(e) a light chain variable region CDR2 comprising SEQ ID NO: 5, 11 or 17; and (f) a light chain variable region CDR3 comprising SEQ ID NO: 6, 12 or 18.

According to one embodiment of the invention, the isolated anti-EDA1 monoclonal antibodies or isolated monoclonal antibody fragments or antigen binding portions or fragments thereof may present an antibody heavy chain selected among: IgG, IgM, IgA, IgE, single chain antibody and other immunoglobulin-derived constructs or non-antibody binding proteins.

As used herein, the term "isotype" refers to the antibody class (e. g., IgM, IgA, IgE or IgG) that is encoded by heavy chain constant region genes.

Usually, the non-antibody binding proteins comprise adnectins (fibronectin-based reagents), Affibody (protein A-based reagents), DARPins (ankyrin-based reagents), avimers (cysteine rich cell surface receptor proteins), anticalins (lipocalin-derived reagents), and nucleotide-based reagents and the like (see for example Nutall & Walsh *Curr. Opin. Pharmacol.* 2008, 8:609).

When the isolated antagonist anti-EDA1 monoclonal antibodies or isolated monoclonal antibody fragments or antigen binding portions or fragments thereof may present a IgG antibody heavy chain, the latter may be selected among: IgG1, IgG2, IgG3 or IgG4, mutated IgG1 that is no longer recognized by FcR; mutated IgG4 sequence that no longer undergoes heavy chain swapping; mutated IgG to modify glycosylation; PEGylated IgG and the like. It is acknowledged that all possible "isotype switching" known to the person skilled in the art may be envisioned in the context of the present invention.

As used herein, "isotype switching" refers to the phenomenon by which the class, or isotype, of an antibody changes from one Ig class to one of the other Ig classes.

Among the list of antibody-based scaffolds, $V_{NAR}$, which are lamprey-derived single domain antibodies, may be advantageously used.

The term "sequence identity/similarity" has its ordinary meaning in the field. The terms "identical" or percent "identity" in the context of two or more polypeptide sequences, refer to two or more sequences that are the same, or have a specified percentage of amino acid residues that are the same (i.e., at least 70% identity, at least 75%, 80%, 85%, 90%, 95%, 98% or 99% identity over a specified region), when compared and aligned for maximum correspondence. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

This homology is more significant when the orthologous proteins or cDNAs are derived from species which are more closely related (e.g., human and mouse sequences), compared to species more distantly related (e.g., human and C. elegans sequences).

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:23744, 1988; Higgins & Sharp, CABIOS 5:151-3, 1989; Corpet et al., Nucl. Acids Res. 16:10881-90, 1988; Huang et al. Computer Appls. Biosci. 8, 155-65, 1992; and Pearson et al., Meth. Mol. Biol. 24:307-31, 1994. Altschul et al., J. Mol Biol. 215:403-10, 1990, presents a detailed consideration of sequence alignment methods and homology calculations. The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 85%, 90%, 92%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site. Homologs of the disclosed anti-EDA1 monoclonal antibodies are typically characterized by possession of at least 70%, at least 95%, or at least 98% sequence identity sequence identity counted over the full-length alignment with the disclosed amino acid sequences using the NCBI Blast 2.0, or using the manual alignment as described above. Proteins with even greater similarity to the anti-EDA1 monoclonal antibody sequences will show increasing percentage identities when assessed by this method, such as at least 75%, 80%, 85%, 90%, 95% or even 98% sequence identity. When less than the entire sequence is being compared for sequence identity, homologs will typically possess at least 75% sequence identity over short windows of 10-20 amino acids, and can possess sequence identities of at least 85%, 90%, 95% or even 98% depending on their similarity to the reference sequence. One of skill in the art will appreciate that these sequence identity ranges are provided for guidance only; it is possible that strongly significant homologs could be obtained that fall outside the ranges provided.

The present invention also includes variants of the anti-EDA1 monoclonal antibodies. The term "variants" or derivatives or equivalents of the anti-EDA1 monoclonal antibody sequences refer to polypeptides having amino acid sequences that differ to some extent from a native sequence polypeptide that is amino acid sequences that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Typically, such variants possess at least 90%, at least 95%, or at least 98%, sequence identity with the native sequence. Variants which are particularly preferred in this connection are replacement variants which typically contain less than 10, less than 5, or less than 3 replacements as compared with the respective disclosed sequences.

In addition or alternative to modifications made within the framework or CDR regions, anti-EDA1 monoclonal antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody.

Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. Such an approach is described in further detail in U.S. Pat. Nos. 5,714,350 and 6,350,861 by Co et al., each of which is incorporated herein by reference in entirety.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express anti-EDA1 monoclonal antibodies of the invention to thereby produce an antibody with altered glycosylation. Alternatively, the fucose residues of the antibody may be cleaved off using a fucosidase enzyme.

Another modification of the antibodies herein that is contemplated by the invention is PEGylation. An antibody can be PEGylated to, for example, increase the biological (e.g., serum) half-life of the antibody. To PEGylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In some embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C1O) alkoxy- or aryloxy-polyethylene glycol or polyethylene glycol-maleimide. In certain embodiments, the antibody to be PEGylated is a glycosylated antibody. Methods for PEGylating proteins are known in the art and can be applied to the antibodies of the invention. See for example, EP 0 154 316 by Nishimura et al. and EP 0 401 384 by Ishikawa et al, each of which is incorporated herein by reference in entirety.

In one embodiment, the anti-EDA1 monoclonal antibodies do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain.

In another embodiment, antibodies are selected that do not rapidly degrade. Fragmentation of a monoclonal anti-EDA1 antibody may be measured using capillary electrophoresis (CE) and MALDI-MS, techniques which are well known to those with ordinary skill in the art (Alexander A J and Hughes D E (1995) *Anal. Chem* 67:3626-32). In another embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, 20% or less, 15% or less, 10% or less or 5% or less. Aggregation may be measured by several techniques which are well known in the art, including size-exclusion column (SEC) high performance liquid chromatography (HPLC), and light scattering to identify monomers, dimers, trimers or multimers.

Figure 30:
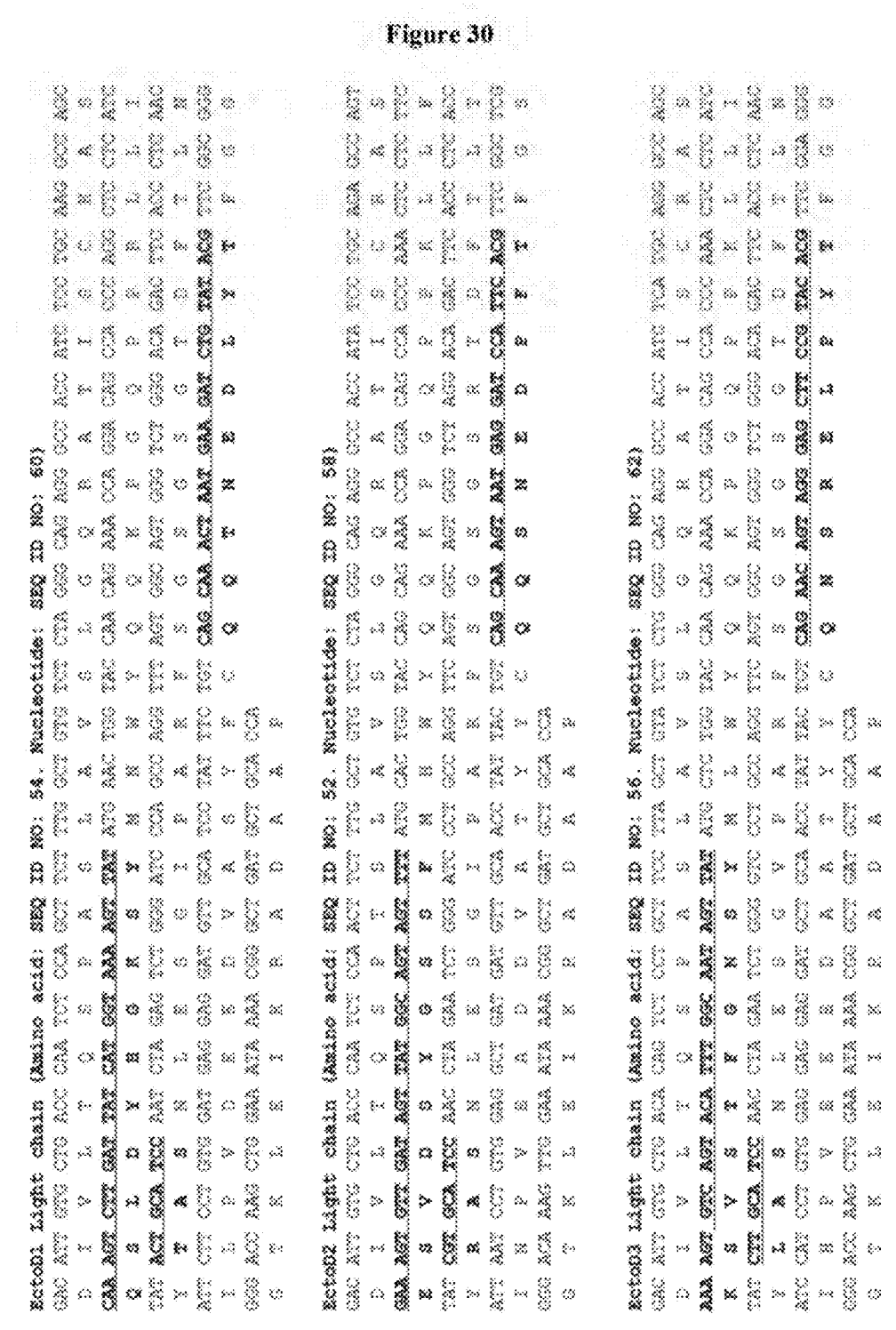
Figure 31:
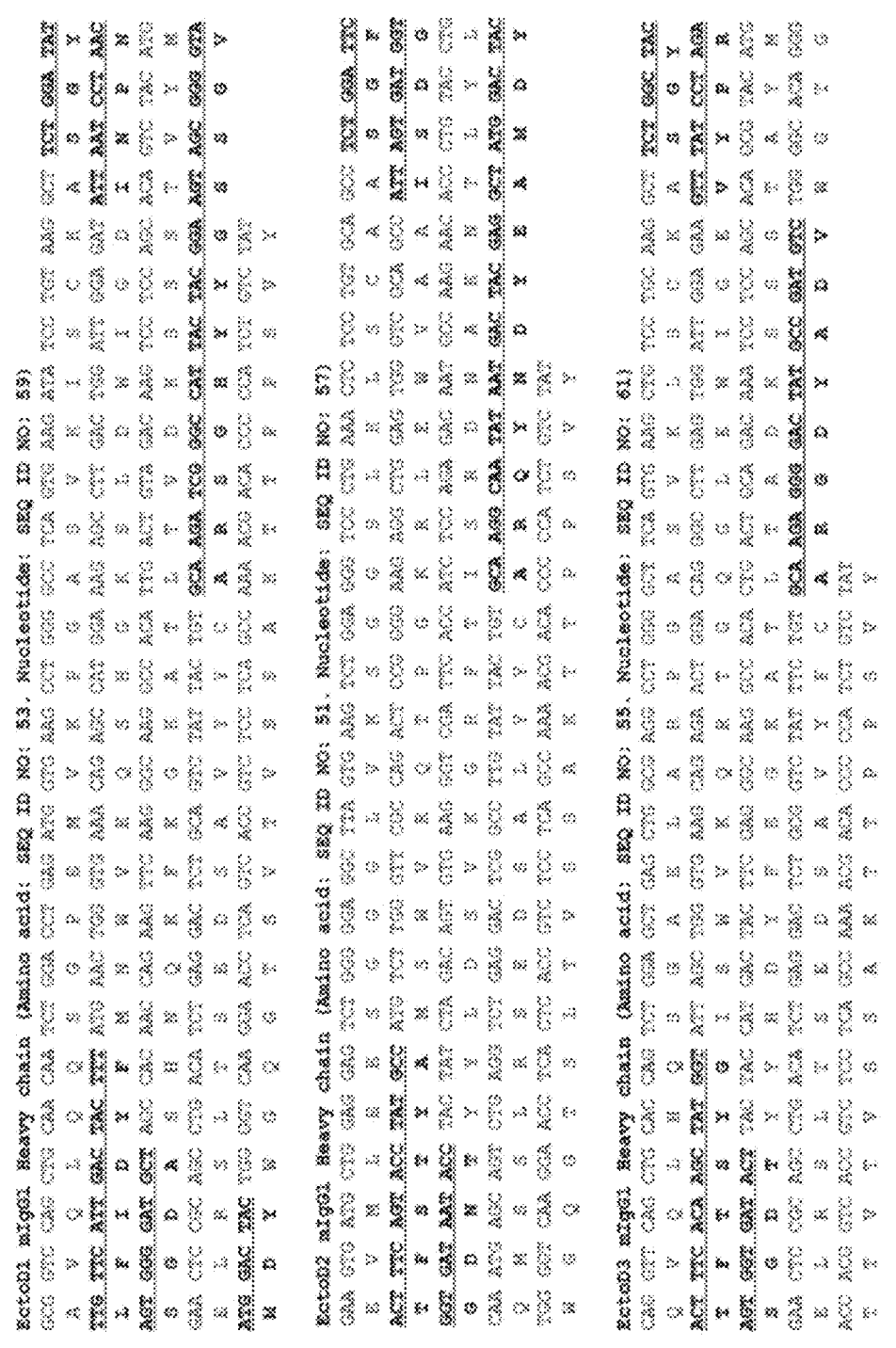
Figure 32:
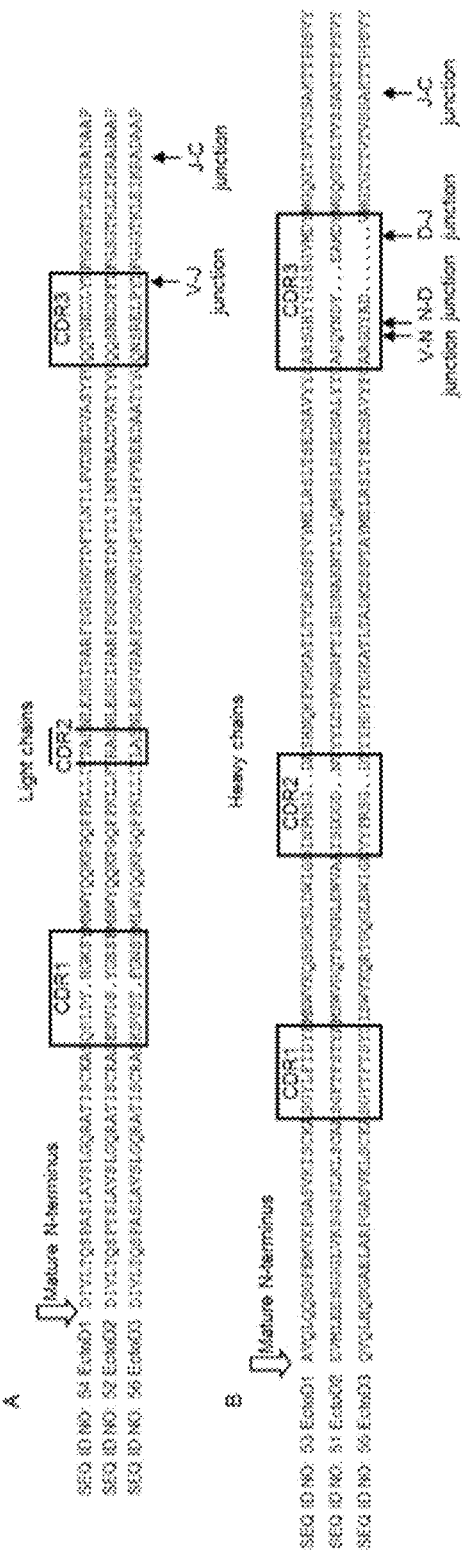
FIG. 32. Amino acid sequences of the light and heavy chains of mAbEDA1-EctoD1, mAbEDA1-EctoD2, and mAbEDA1-EctoD3 showing the three CDRs for each chain as well as a V-J junction, J-C junctions, a V-N junction, an N-D junction and a D-J junction.

FIGS. 30, 31, and 32 show the amino acid sequences of the variable regions of the light chains and heavy chains in respect of three anti-EDA1 monoclonal antibodies, namely mAbEDA1-EctoD1, mAbEDA1-EctoD2 and mAbEDA1-EctoD3.

Given a specific variable domain region sequence, one of ordinary skill can easily screen for complementary variable domain region sequences using methods well known in the art. See, for example, Klimka et al., *British Journal of Cancer* (2000) 93: 252-260; Beboer et al., *J. Mol. Biol.* (2000) 296: 833-849; Radar et al., *Proc. Natl. Acad. Sci. USA* (1998) 95:8910-8915; Portolano et al, *J. Immunol.* (193) 150: 880-887; and Clarkson et al., *Nature* (1991) 352: 624-628, each of which is incorporated herein by reference in entirety. For example, a heavy chain variable domain sequence comprising 1, 2, or 3 of the heavy chain CDR amino acid sequences described herein can be screened against a library of light chain variable domain sequences to obtain antibodies that bind human and/or mouse and/or avian EDA1. Alternatively, a light chain variable domain sequence comprising 1, 2, or 3 of the light chain CDRs described herein can be screened against a library of heavy chain variable domain sequences to obtain antibodies that bind human and/or mouse and/or avian EDA1. Without wishing to be bound by theory, this methodology can be used to humanize any known antibody. For example, a non-human variable domain sequence can be screened against human variable domain sequences and then the identified human variable domain sequences screened against a second set of human variable domain sequences.

Generally, amino acid sequences having at least 80%, 85%, 90%, or 95% sequence identity to the variable domain region sequences will differ from the variable domain region sequence at substitutable positions. A "substitutable position" is a particular position of the variable domain region sequence that can be substituted by different amino acid(s) without significantly decreasing the binding activity of the antibody. A substitutable position may also be referred to as "variation tolerant position." Substitutable positions of variable domain sequence are revealed by aligning the heavy chain or light chain variable domain sequences and determining which amino acid occurs at which position. A substitutable position of a variable domain sequence disclosed herein is identified by virtue of the fact that the identity of the amino acid at the substitutable position varies between the individual variable domain sequences of related antibodies, e.g., antibodies exemplified herein. Once identified, the amino acid at the substitutable position of an individual variable domain sequence can be substituted for a different amino acid without significantly decreasing the binding affinity of the antibody.

Generally to obtain antibodies, antibodies fragments, or antigen binding portions or fragments thereof, substitutable positions outside the CDRs are preferred. However, one, two, three, four, or five or more positions in the CDRs can also be used. In some embodiments, when substitutable positions within CDRs are used no more than one, two, three, four or five such positions may be used as substitutable positions. U.S. Patent Publication No. 20060099204, (incorporated herein by reference in entirety), describes methods for identifying substitutable positions.

In some embodiments, the antibody, antibody fragment, or antigen binding portion or fragments thereof bind to human and/or mouse and/or avian EDA1 bind to human and/or mouse and/or avian EDA1 sequence fragments corresponding to SEQ ID NO: 49 and/or SEQ ID NO: 50, respectively.

In certain embodiments, the isolated monoclonal antibody or isolated monoclonal antibody fragment or antigen binding portion or fragment thereof binds to human and/or mouse and/or avian EDA1 with an affinity constant (KD) of at least $10^{-8}$ M.

According to one embodiment of the invention, the antibody, antibody fragment, or antigen binding portion or fragment thereof is a humanized antibody, antibody fragment, or antigen binding portion or fragment thereof.

In one embodiment of the invention said antibody, antibody fragment, or antigen binding portion or fragment thereof is monovalent. According to another embodiment of the invention, said antibody, antibody fragment, or antigen binding portion or fragment thereof is bivalent or multivalent.

In some embodiments, the antibody, antibody fragment, or antigen binding portion or fragment thereof is a single chain antibody, antibody fragment, or antigen binding portion or fragment thereof.

According to one embodiment, said antibody, antibody fragment, or antigen binding portion or fragment thereof is a Fab, F(ab)'2, Fv, Fab/c, Fv, single chain Fv (scFv), or Fd fragment.

According to another embodiment, the antibody, antibody fragment, or antigen binding portion or fragment thereof is a chimeric antibody, antibody fragment, or antigen binding portion or fragment thereof.

According to another embodiment of the invention, the antibody, antibody fragment, or antigen binding portion or fragment thereof is a fusion protein.

In some embodiments, the heavy chain of the isolated monoclonal antibody or isolated monoclonal antibody fragment or antigen binding portion or fragment thereof of the invention is selected from the group consisting of heavy chain of IgG, IgM, IgA, IgE, single chain antibody, immunoglobulin-derived constructs, and non-antibody binding proteins. In some embodiments, the IgG is selected from the group consisting of IgG1, IgG2, IgG3, IgG4, mutated IgG1 that is no longer recognized by FcR, and mutated IgG4 that no longer undergoes heavy chain swapping.

According to another embodiment, the non-antibody binding protein of the isolated monoclonal antibody or isolated monoclonal antibody fragment or antigen binding portion or fragment thereof is selected from the group consisting of adnectins, Affibody, DARPins, avimers, anticalins, and nucleotide based reagents.

As used herein, the term "antigenic determinant" refers to that portion of an antigen that makes contact with a particular antibody, antibody fragment, or antigen binding portion or fragment thereof (i.e., an epitope). When a protein or fragment of a protein is used to immunize a host animal, numerous regions of the protein may induce the production of antibodies which bind specifically to a given region or three dimensional structure on the protein; these regions or structures are referred to as antigenic determinants. An antigenic determinant may compete with the intact antigen (i.e., the immunogen used to elicit the immune response) for binding to an antibody, antibody fragment, or antigen binding portion or fragment thereof.

As used herein, the phrase "competes for binding at that antigenic determinant" refers to the ability of an antibody, antibody fragment, or antigen binding portion or fragment thereof to increase the affinity constant, for binding to same antigenic determinant, of a second antibody, antibody fragment, or antigen binding portion or fragment thereof by at least 5%, 10%, 20%, 30%, 40%, 50%, 60%, 70%, 80%. 90%, 100%, 1.1 fold, 1.25 fold, 1.5 fold, 5 fold, 10, fold, 50 fold, 100 fold or more in a competition binding assay. One of ordinary skill is well aware of methods for determining binding constants. One method for measuring binding constants is the commercially available Biacore assay apparatus. In some embodiments, the binding affinity of an antibody, antibody fragment, or antigen binding portion or fragment thereof is higher than $10^{-7}$ M in the presence of the competing antibody, antibody fragment, or antigen binding portion or fragment thereof.

Chimeric antibodies are antibodies whose light and heavy chain genes have been constructed, typically by genetic engineering, from antibody variable and constant region genes belonging to different species. For example the variable region of the genes from a mouse monoclonal antibody may be joined to human constant regions, such as gamma 1, gamma 2, gamma 3 and gamma 4.

The term "fusion protein" as used herein refers to a polypeptide which comprises protein domains from at least two different proteins. For example, a fusion protein may comprise an antigen-binding portion or fragment of an antibody and a non-antibody protein.

In one embodiment of the invention, the antibody, antibody fragment, or antigen binding portion or fragment thereof is conjugated to a ligand and/or a tag.

In one example, the heavy chain of said antibody, antibody fragment, or antigen binding portion thereof is conjugated to the ligand and/or tag.

In another example, the light chain of said antibody, antibody fragment, or antigen binding portion or fragment thereof is conjugated to the ligand and/or tag.

A wide variety of ligands or tags can be coupled (i.e. linked) with the antibodies described herein. Without wishing to be bound by theory, the antibodies of the invention can be conjugated to either other peptides or other molecules to tailor, for example, the bioavailability, serum half-life or shelf-life of the antibodies, immunogenicity, tolerance by human body, or to affect the solubility of the antibodies in pharmaceutically acceptable carriers.

Although, conjugation with ligands and tags is discussed in reference to antibodies herein, it is to be understood that antibody fragments and antigen binding portions and fragments are also amenable to conjugation with ligands and tags. In some embodiments, ligands include naturally occurring molecules. In other embodiments ligands include recombinant or synthetic molecules.

Exemplary ligands include, but are not limited to, polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu$^{3+}$ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNF-alpha), interleukin-1 beta, gamma interferon, natural or recombinant low density lipoprotein (LDL), natural or recombinant high-density lipoprotein (HDL), bovine serum albumin (BSA), ovalbumin, keyhole limpet hemocyanin (KLH), and a cell-permeation agent (e.g., a helical cell-permeation agent).

Ligands can be used for any number of reasons including, but no limited to, targeting, PK modulation, and labeling/tagging. A targeting ligand can provide enhanced affinity for a selected target, e.g., a cell, cell type, tissue, organ, region of the body, or a compartment, e.g., a cellular, tissue or organ compartment. A PK modulating ligand can modulate pharmacokinetics of an antibody in vivo.

In some embodiments, the antibody of the invention is conjugated with a label/tag, such as a fluorescent label or a biotin label. Without wishing to be bound by theory, such labeling allows one to easily track the antibody, if necessary or to assist in purification of the antibody. One can also design the ligand in such a way that is can be removed after purification of the antibody is complete. For example, the ligand can be attached to the antibody via a linker that can be is easily cleavable under the appropriate conditions. Such conditions can include acid or basic pH, heating, sonication, enzymatic cleavage, and the like.

As used herein, the term "label" refers to a composition capable of producing a detectable signal indicative of the presence of a target. Suitable labels include fluorescent molecules, radioisotopes, nucleotide chromophores, enzymes, substrates, chemiluminescent moieties, magnetic particles, bioluminescent moieties, and the like.

As such, a label is any composition detectable by spectroscopic, photochemical, biochemical, immunochemical, electrical, optical or chemical means needed for the methods and devices described herein. For example, the antibody can be labeled with a detectable tag which can then be detected using an antibody specific to the label.

Exemplary fluorescent labels include, but are not limited to, hydroxycoumarin, succinimidyl ester, aminocoumarin, succinimidyl ester, methoxycoumarin, Succinimidyl ester, Cascade Blue, hydrazide, Pacific Blue, maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorophyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

The ligands can be conjugated, either directly or through a linker, to the N-terminal, C-terminal, or the amino acid side chains of the heavy and/or light chain of the antibody. A ligand can be present on an amino acid when said amino acid is incorporated into the antibody heavy and/or light during synthesis. In some embodiments, the ligand can be incorporated via coupling to a "precursor" amino acid after said "precursor" amino acid has been incorporated into the antibody heavy and/or light chain. For example, a ligand having an electrophilic group, e.g., a pentafluorophenyl ester or aldehyde group, can be conjugated to the N-terminal of heavy and/or light chain of the antibody.

In another example, a monomer having a chemical group suitable for taking part in Click Chemistry reaction can be incorporated, e.g., an azide or alkyne group. In a subsequent operation, i.e., after incorporation of the precursor monomer antibody heavy and/or light chain, a ligand having complementary chemical group, e.g., an alkyne or azide can be attached to the precursor monomer by coupling the alkyne and the azide together.

In some embodiments, the covalent linkages between the antibody and a ligand are mediated by a linker. This linker can be cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the antibody after transport to the desired target. The intended nature of the conjugation or coupling interaction, or the desired biological effect, will determine the choice of linker group.

As used herein, the term "non-peptide linker" means an organic moiety that connects two parts of the peptide and such a moiety is not a peptide. Linkers typically comprise a direct bond or an atom such as oxygen or sulfur, a unit such as $NR^1$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, $C(O)$, cleavable linking group, substituted or unsubstituted aryl, substituted or unsubstituted heteroaryl, substituted or unsubstituted heterocyclic; where $R^1$ is hydrogen, acyl, aliphatic or substituted aliphatic. The two parts of the compound can be linked together by providing on each part of the molecule complementary chemical functionalities that undergo a coupling reaction.

In some embodiments, linkers can be non-covalent coupling of two parts of a compound or two different molecules. Such non-covalent coupling can be achieved through, for example, ionic interactions, H-bonding, van der Waals interactions and affinity of one molecule for another. When non-covalent coupling is used, each part of the compound can be conjugated with a moiety that has complementary to another moiety that is conjugated to the second part of the compound. One example of such complementary coupling is the biotin/avidin coupling.

Other examples include affinity of an oligonucleotide for its complementary strand, receptor/ligand binding, aptamer/ligand binding and antibody/antigen binding.

Many strategies are known in the art for conjugating peptides to peptides and other molecules. For example, Hermanson, G. T., *Bioconjugate Techniques*, $2^{nd}$ Ed., Academic Press (2008) and Niemeyr, C. M., *Bioconjugation Protocols: Strategies and Methods (Methods in Molecular Biology)*, Humana Press (2004) provide a number of methods and techniques for conjugating peptides to other molecules. Contents of both of these are herein incorporated by reference in their entirety for all purposes. For a review of site-specific introduction of non-natural amino acids into peptides for conjugation see A. J. de Graaf, et al., *Biocon-*

*jugate Chemistry* (2009) 20(7):1281-1295, contents of which are herein incorporated in its entirety. PCT publication No.: WO9213095, incorporated herein by reference in entirety, describes methods for PEGylation of peptides.

One conjugation strategy is the biotin-sandwich method (Davis, et al., *Proc. Natl. Acad. Sci. USA* 103:8155-8160 (2006)) in which a peptide is biotinylated and bound to biotinylated ligand using tetravalent streptavidin as a linker. To accomplish this, the peptide may be coupled to the 15 amino acid sequence of an acceptor peptide for biotinylation (referred to as AP; Chen, et al., *Nat. Methods* 2:99-104 (2005)). The fusion proteins can be made by incorporating the extra sequences at the N- or the C-terminus of the peptide. The acceptor peptide sequence allows site-specific biotinylation by the *E. coli* enzyme biotin ligase (BirA; Chen, et al., *Nat. Methods* 2:99-104 (2005)).

A ligand peptide can be similarly biotinylated for conjugation with a peptide described herein. Many commercial kits are available for biotinylating proteins. Non-peptidyl ligands agents can also be conjugated with biotin using methods well known in the art for conjugating biotin to non-peptide molecules, e.g. small organic molecules. In order to prevent steric interference between the biotin/avidin groups and the peptides or the ligands, a spacer may be included between them.

The linkers and linking methods described herein can also be used for linking together heavy chain and light chain of an antibody, two or more Fv domains, and fragments thereof.

For simplicity, chemical moieties are defined and referred to throughout can be univalent chemical moieties (e.g., alkyl, aryl, etc.) or multivalent moieties under the appropriate structural circumstances clear to those skilled in the art.

The term "alkyl" refers to saturated non-aromatic hydrocarbon chains that may be a straight chain or branched chain, containing the indicated number of carbon atoms (these include without limitation methyl, ethyl, propyl, allyl, or propargyl), which may be optionally inserted with N, O, S, SS, $SO_2$, C(O), C(O)O, OC(O), C(O)N or NC(O). For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "cyclyl", "cyclic" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heterocyclyl", "heterocycle" or "heterocyclic" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "optionally substituted" means that the specified group or moiety, such as an alkyl, aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, heteroaryl, acyl, amino group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkylthio, $CF_3$, N-morphilino, phenylthio, alkanesulfonyl, arenesulfonyl, alkanesulfonamido, arenesulfonamido, aralkylsulfonamido, alkylcarbonyl, acyloxy, cyano or ureido. In some embodiments, substituent can itself be optionally substituted. In some cases, two substituents, together with the carbons to which they are attached, can form a ring.

The term "halo" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkoxy" refers to an —O-alkyl radical.

The term "aminoalkyl" refers to an alkyl substituted with an amino.

The term "mercapto" refers to an —SH radical.

The term "thioalkoxy" refers to an —S-alkyl radical.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

Nucleic Acids Encoding Anti-EDA1 Antibodies

Another aspect of the invention provides an isolated nucleic acid molecule encoding the isolated anti-EDA1 monoclonal antibody or isolated monoclonal antibody fragment or antigen binding portions or fragment thereof as defined above.

The term "nucleic acid molecule," as used herein, is intended to include DNA molecules and RNA molecules. A nucleic acid molecule may be single-stranded or double-stranded.

In addition to the above described monoclonal antibodies, artificially altered gene recombinant antibodies such as chimeric antibodies or humanized antibodies can be used for, for example, lowering heteroantigenicity against a human. These altered antibodies can be produced using known methods.

Chimeric antibodies can e.g., be obtained by ligating the DNA encoding the antibody V-region to a DNA encoding a human antibody C-region, incorporating the product into an expression vector, and then introducing the vector into a host to cause the host to produce the antibodies. Using this known method, chimeric anti-EDA1 monoclonal antibodies useful in the present invention can be obtained.

Humanized antibodies are also referred to as reshaped human antibodies, which are prepared by grafting an antibody CDR (complementarity determining region) of a mammal other than a human, such as a mouse, to the CDR of a human antibody. The general gene recombination technique thereof is also known (see European Patent Application Publication EP 125023 and WO 96/02576, or any one of their US counterparts, such as, for example, U.S. Pat. No. 6,068,040—each of these patents and publications are incorporated herein by reference in entirety).

The term "humanized antibody" is intended to refer to antibodies in which CDR sequences derived from the germline of another mammalian species, such as a mouse, have been grafted onto human framework sequences. Additional framework region modifications may be made within the human framework sequences.

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized monoclonal antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al, each of which is incorporated herein by reference in entirety). In one embodiment, the antibodies of the invention are human monoclonal antibodies.

CDR nucleotide sequences encoding the anti-EDA1 monoclonal antibodies or isolated monoclonal antibody fragments or antigen binding portions or fragments thereof are shown in Table 2.

TABLE 3

Nucleotide sequences of CDRs of anti-EDA1 monoclonal antibodies

| mAb | Chain | CDR | CDR nucleotide sequence | SEQ ID NO: |
|---|---|---|---|---|
| mAbEDA1-EctoD2 | Heavy | CDR1 | TCTGGATTCACTTTCAGTACCTATGCC | 25 |
| mAbEDA1-EctoD2 | Heavy | CDR2 | ATTAGTGATGGTGGTGATAATACC | 26 |
| mAbEDA1-EctoD2 | Heavy | CDR3 | GCAAGGCAATATAATGACTACGAGGCTATGGACTAC | 27 |
| mAbEDA1-EctoD2 | Light | CDR1 | GAAAGTGTTGATAGTTATGGCAGTAGTTTT | 28 |
| mAbEDA1-EctoD2 | Light | CDR2 | CGTGCATCC | 29 |
| mAbEDA1-EctoD2 | Light | CDR3 | CAGCAAAGTAATGAGGATCCATTCACG | 30 |
| mAbEDA1-EctoD1 | Heavy | CDR1 | TCTGGATATTTGTTCATTGACTACTTT | 31 |
| mAbEDA1-EctoD1 | Heavy | CDR2 | ATTAATCCTAACAGTGGGGATGCT | 32 |
| mAbEDA1-EctoD1 | Heavy | CDR3 | GCAAGATCGGGCCATTACTACGGAAGTAGCGGGGTAATGGACTAC | 33 |
| mAbEDA1-EctoD1 | Light | CDR1 | CAAAGTCTTGATTATCATGGTAAAAGTTAT | 34 |
| mAbEDA1-EctoD1 | Light | CDR2 | ACTGCATCC | 35 |
| mAbEDA1-EctoD1 | Light | CDR3 | CAGCAAACTAATGAAGATCTGTATACG | 36 |
| mAbEDA1-EctoD3 | Heavy | CDR1 | TCTGGCTACACTTTCACAAGCTATGGT | 37 |
| mAbEDA1-EctoD3 | Heavy | CDR2 | GTTTATCCTAGAAGTGGTGATACT | 38 |
| mAbEDA1-EctoD3 | Heavy | CDR3 | GCAAGAGGGGACTATGCCGATGTC | 39 |
| mAbEDA1-EctoD3 | Light | CDR1 | AAAAGTGTCAGTACATTTGGCAATAGTTAT | 40 |
| mAbEDA1-EctoD3 | Light | CDR2 | CTTGCATCC | 41 |
| mAbEDA1-EctoD3 | Light | CDR3 | CAGAACAGTAGGGAGCTTCCGTACACG | 42 |

TABLE 4

Nucleotide sequences of heavy and light chains of anti-EDA1 monoclonal antibodies

| monoclonal Antibody | Chain | SEQ ID NO: |
|---|---|---|
| mAbEDA1-EctoD2 | Heavy | 43 |
| mAbEDA1-EctoD2 | Light | 44 |
| mAbEDA1-EctoD1 | Heavy | 45 |
| mAbEDA1-EctoD1 | Light | 46 |
| mAbEDA1-EctoD3 | Heavy | 47 |
| mAbEDA1-EctoD3 | Light | 48 |
| mAbEDA1-EctoD2 | Heavy | 57 |
| mAbEDA1-EctoD2 | Light | 58 |
| mAbEDA1-EctoD1 | Heavy | 59 |
| mAbEDA1-EctoD1 | Light | 60 |
| mAbEDA1-EctoD3 | Heavy | 61 |
| mAbEDA1-EctoD3 | Light | 62 |

In addition, FIGS. 30 and 31 show the nucleotide sequences of the light and heavy chains of anti-EDA1 monoclonal antibodies mAbEDA1-EctoD1, mAbEDA1-EctoD2 and mAbEDA1-EctoD3.

Expression Vectors, Host Cells, Hybridomas and Transgenic Animals

Another aspect of the invention is an expression vector comprising at least one copy of the nucleic acid molecule described above.

The term "vector" as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e. g., bacterial vectors having a bacterial origin of replication and episomal mammalian vectors). Other vectors (e. g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

In general, expression vectors of utility in recombinant DNA techniques are often in the form of plasmids. In the present specification, the terms "plasmid" and "vector" may be used interchangeably as the plasmid is the most commonly used form of vector. However, the invention is intended to include such other forms of expression vectors, such as viral vectors (e. g. replication defective retroviruses, adenoviruses and adeno-associated viruses), which serve equivalent functions.

The invention also concerns host cells comprising the above described expression vector. The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

Expression vectors and host cells suitable for expression of recombinant antibodies and humanized antibodies in particular, are well known in the art. The following references are representative of methods and vectors suitable for expression of recombinant immunoglobulins which may be utilized in carrying out the present invention: Weidle et al., *Gene*, 51: 21-29 (1987); Dorai et al., *J. Immunol.*, 13 (12): 4232-4241 (1987); De Waele et al., *Eur. J. Biochem.*, 176: 287-295 (1988); Colcher et al., *Cancer Res.*, 49: 1738-1745 (1989); Wood et al., *J. Immunol.*, 145 (9): 3011-3016 (1990); Bulens et al., *Eur. J. Biochem.*, 195: 235-242 (1991); Beldsington et al., *Biol. Technology*, 10: 169 (1992); King et al., *Biochem. J.*, 281: 317-323 (1992); age et al., *Biol. Technology*, 9: 64 (1991); King et al., *Biochem. J.*, 290: 723-729 (1993); Chaudhary et al., *Nature*, 339: 394-397 (1989); Jones et al., *Nature*, 321: 522-525 (1986); Morrison and Oi, *Adv. Immunol.*, 44: 65-92 (1989); Benhar et al., *Proc. Natl. Acad. Sci. USA*, 91: 12051-12055 (1994); Singer et al., *J. Immunol.*, 150: 2844-2857 (1993); Couto et al., *Hybridoma*, 13 (3): 215-219 (1994); Queen et al., *Proc. Natl. Acad. Sci. USA*, 86: 10029-10033 (1989); Caron et al., *Cancer Res.*, 52: 6761-6767 (1992); Coloura et al, *J. Immunol. Meth.*, 152: 89-109 (1992), each of which is incorporated herein by reference in entirety. Moreover, vectors suitable for expression of recombinant antibodies are commercially available. The vector may, for example, be a bare nucleic acid segment, a carrier-associated nucleic acid segment, a nucleoprotein, a plasmid, a virus, a viroid, or a transposable element.

Host cells known to be capable of expressing functional immunoglobulins include, for example, mammalian cells such as Chinese Hamster Ovary (CHO) cells; COS cells; myeloma cells, such as NSO and SP2/0 cells; insect cells, bacteria such as *Escherichia coli*; yeast cells such as *Saccharomyces cerevisiae*; and other host cells. Of these, CHO cells are used by many researchers given their ability to effectively express and secrete immunoglobulins. NSO cells are one of the preferred types of host cells useful in the present invention.

Host cells are transformed following techniques that are known to the person skilled in the art. A "transformed" cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, calcium phosphate precipitation, and particle gun acceleration.

In particular, the present invention also relates to a hybridoma secreting the isolated anti-EDA1 monoclonal antibodies or isolated monoclonal antibody fragments or antigen binding portions or fragments thereof according to the present invention.

The hybridomas producing monoclonal antibodies can be passage-cultured in a standard culture solution, or can be stored for a long period in liquid nitrogen. One example of a method employed to obtain monoclonal antibodies from the hybridomas involves culturing the hybridomas and obtaining monoclonal antibodies in the culture supernatant according to a standard method. The former method is suitable for the mass production of antibodies.

A monoclonal antibody that can be used in the present invention can be a recombinant monoclonal antibody that is prepared by cloning the antibody gene from the hybridoma, incorporating the gene into an appropriate vector, introducing the vector into a host, and then causing the host to produce the recombinant monoclonal antibodies by genetic engineering techniques (e.g., see Vandamme, A. M. et al., *Fur. J. Biochem*, (1990) 192, 767-775, incorporated herein by reference in entirety).

In addition to the above host cell, a transgenic animal or plant can also be used to produce a recombinant antibody. Thus, another aspect of the invention concerns a transgenic non-human animal having a genome comprising the isolated nucleic acid molecule and/or the expression vector described herein. Methods for producing such transgenic animals are well known to those skilled in the art and can be adapted without undue experimentation for use with certain aspects of the present invention.

Immunoassays

Immunoassays often are used to diagnose disease, and test results can provide information about a disease that may help in planning treatment. An immunoassay takes advantage of the specific binding of an antibody to its antigen. Monoclonal antibodies are often used as they usually bind only to one site of a particular molecule, and therefore provide a more specific and accurate test, which is less easily confused by the presence of other molecules. The antibodies used must have a high affinity for the antigen of interest, because a very high proportion of the antigen must bind to the antibody in order to ensure that the assay has adequate sensitivity.

The immunoassays and kits for immunoassays of the present invention may comprise the anti-EDA1 monoclonal antibodies described herein to specifically bind to EDA1 in a biological sample. Any type of immunoassay format may be used, including, without limitation, enzyme immunoassays (ETA, ELISA), radioimmunoassay (RIA), fluoroimmunoassay (FIA), chemiluminescent immunoassay (CLIA), counting immunoassay (CIA), immunohistochemistry (IHC), agglutination, nephelometry, turbidimetry or Western Blot. These and other types of immunoassays are well-known and are described in the literature, for example, in Immunochemistry, Van Oss and Van Regenmortel (Eds), CRC Press, 1994; The Immunoassay Handbook, D. Wild (Ed.), Elsevier Ltd., 2005; and the references disclosed therein.

In certain embodiments of the present invention, the immunoassay is the enzyme-linked immunosorbent assay (ELISA). ELISA is a highly sensitive technique for detecting and measuring antigens or antibodies in a solution in which the solution is run over a surface to which immobilized antibodies specific to the substance have been attached, and if the substance is present, it will bind to the antibody layer, and its presence is verified and visualized with an application of antibodies that have been tagged or labeled so as to permit detection. ELISAs combine the high specificity of antibodies with the high sensitivity of enzyme assays by using antibodies or antigens coupled to an easily assayed enzyme that possesses a high turnover number such as alkaline phosphatase (AP) or horseradish peroxidase (HRP), and are very useful tools both for determining antibody concentrations (antibody titer) in sera as well as for detecting the presence of antigen.

There are many different types of ELISAs; the most common types include "direct ELISA," "indirect ELISA," "sandwich ELISA" and cell-based ELISA (C-ELISA). Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate typically is washed with a mild detergent solution to remove any proteins or antibodies that are not specifically bound. After the final wash step the plate is developed by adding an enzymatic substrate tagged with a detectable label to produce a visible signal, which indicates the quantity of antigen in the sample.

In a typical microtiter plate sandwich immunoassay, an antibody ("capture antibody") is adsorbed or immobilized onto a substrate, such as a microtiter plate. Monoclonal antibodies are preferred as capture antibodies due to their greater specificity, but polyclonal antibodies also may be used. When the test sample is added to the plate, the antibody on the plate will bind the target antigen from the sample, and retain it in the plate. When a second antibody ("detection antibody") or antibody pair is added in the next step, it also binds to the target antigen (already bound to the monoclonal antibody on the plate), thereby forming an antigen "sandwich" between the two different antibodies.

This binding reaction can then be measured by radio-isotopes, as in a radioimmunoassay format (RIA); by enzymes, as in an enzyme immunoassay format (EIA or ELISA); or other detectable label, attached to the detection antibody. The label generates a color signal proportional to the amount of target antigen present in the original sample added to the plate. Depending on the immunoassay format, the degree of color can be detected and measured with the naked eye (as with a home pregnancy test), a scintillation counter (for an RIA), or with a spectrophotometric plate reader (for an EIA or ELISA).

The assay then is carried out according to the following general steps:

Step 1: Capture antibodies are adsorbed onto the well of a plastic microtiter plate (no sample added);

Step 2: A test sample (such as human serum) is added to the well of the plate, under conditions sufficient to permit binding of the target antigen to the capture antibody already bound to the plate, thereby retaining the antigen in the well;

Step 3: Binding of a detection antibody or antibody pair (with enzyme or other detectable moiety attached) to the target antigen (already bound to the capture antibody on the plate), thereby forming an antigen "sandwich" between the two different antibodies. The detectable label on the detection antibodies will generate a color signal proportional to the amount of target antigen present in the original sample added to the plate.

In an alternative embodiment, sometimes referred to as an antigen-down immunoassay, the analyte (rather than an antibody) is coated onto a substrate, such as a microtiter plate, and used to bind antibodies found in a sample. When the sample is added (such as human serum), the antigen on the plate is bound by antibodies (IgE for example) from the sample, which are then retained in the well. A species-specific antibody (anti-human IgE for example) labeled with an enzyme such as horse radish peroxidase (HRP) is added next, which, binds to the antibody bound to the antigen on the plate. The higher the signal, the more antibodies there are in the sample.

In another embodiment, an immunoassay may be structured in a competitive inhibition format. Competitive inhibition assays are often used to measure small analytes because competitive inhibition assays only require the binding of one antibody rather than two as is used in standard ELISA formats. In a sequential competitive inhibition assay, the sample and conjugated analyte are added in steps similar to a sandwich assay, while in a classic competitive inhibition assay, these reagents are incubated together at the same time.

In a typical sequential competitive inhibition assay format, a capture antibody is coated onto a substrate, such as a microtiter plate. When the sample is added, the capture antibody captures free analyte out of the sample. In the next step, a known amount of analyte labeled with a detectable label, such as an enzyme or enzyme substrate, added. The labeled analyte also attempts to bind to the capture antibody adsorbed onto the plate. However, the labeled analyte is inhibited from binding to the capture antibody by the presence of previously bound analyte from the sample. This means that the labeled analyte will not be bound by the monoclonal on the plate if the monoclonal has already bound unlabeled analyte from the sample. The amount of unlabeled analyte in the sample is inversely proportional to the signal generated by the labeled analyte. The lower the signal, the more unlabeled analyte there is in the sample. A standard curve can be constructed using serial dilutions of an unlabeled analyte standard. Subsequent sample values can then be read off the standard curve as is done in the sandwich ELISA formats. The classic competitive inhibition assay format requires the simultaneous addition of labeled (conjugated analyte) and unlabeled analyte (from the sample). Both labeled and unlabeled analyte then compete simultaneously for the binding site on the monoclonal capture antibody on the plate. Like the sequential competitive inhibition format, the colored signal is inversely proportional to the concentration of unlabeled target analyte in the sample. Detection of labeled analyte can be read on a microtiter plate reader.

In addition to microtiter plates, immunoassays are also may be configured as rapid tests, such as a home pregnancy test. Like microtiter plate assays, rapid tests use antibodies to react with antigens and can be developed as sandwich formats, competitive inhibition formats, and antigen-down formats. With a rapid test, the antibody and antigen reagents are bound to porous membranes, which react with positive samples while channeling excess fluids to a non-reactive part of the membrane. Rapid immunoassays commonly come in two configurations: a lateral flow test where the sample is simply placed in a well and the results are read immediately; and a flow through system, which requires placing the sample in a well, washing the well, and then finally adding an analyte-detectable label conjugate and the result is read after a few minutes. One sample is tested per strip or cassette. Rapid tests are faster than microtiter plate assays, require little sample processing, are often cheaper, and generate yes/no answers without using an instrument. However, rapid immunoassays are not as sensitive as plate-based immunoassays, nor can they be used to accurately quantitate an analyte.

In certain embodiments of the present invention, the amount of EDA1 in circulating cells is determined using sandwich ELISA, in which the monoclonal antibodies are used to detect sample antigen. The sandwich ELISA method comprises the following general steps:

Prepare a surface to which a known quantity of capture antibody is bound;

(Optionally) block any non-specific binding sites on the surface;

Apply the antigen-containing sample to the surface;

Wash the surface, so that unbound antigen is removed;

Apply primary (detection) antibodies that bind specifically to the bound antigen;

Apply enzyme-linked secondary antibodies which are specific to the primary antibodies;

Wash the plate, so that the unbound antibody-enzyme conjugates are removed;

Apply a chemical which is converted by the enzyme into a detectable (e.g., color or fluorescent or electrochemical) signal; and Measure the absorbance or fluorescence or electrochemical signal to determine the presence and quantity of antigen.

In an alternate embodiment, the primary antibody (step 5) is linked to an enzyme; in this embodiment, the use of a secondary antibody conjugated to an enzyme (step 6) is not necessary if the primary antibody is conjugated to an enzyme. However, use of a secondary-antibody conjugate avoids the expensive process of creating enzyme-linked antibodies for every antigen one might want to detect. By using an enzyme-linked antibody that binds the Fc region of other antibodies, this same enzyme-linked antibody can be used in a variety of situations. The major advantage of a sandwich ELISA is the ability to use crude or impure samples and still selectively bind any antigen that may be present. Without the first layer of "capture" antibody, any proteins in the sample (including serum proteins) may competitively adsorb to the plate surface, lowering the quantity of antigen immobilized.

In a currently preferred embodiment of the present invention, a solid phase substrate, such as a microtiter plate or strip, is treated in order to fix or immobilize a capture antibody to the surface of the substrate. The material of the solid phase is not particularly limited as long as it is a material of a usual solid phase used in immunoassays. Examples of such material include polymer materials such as latex, rubber, polyethylene, polypropylene, polystyrene, a styrene-butadiene copolymer, polyvinyl chloride, polyvinyl acetate, polyacrylamide, polymethacrylate, a styrene-methacrylate copolymer, polyglycidyl methacrylate, an acrolein-ethyleneglycol dimethacrylate copolymer, polyvinylidene difluoride (PVDF), and silicone; agarose; gelatin; red blood cells; and inorganic materials such as silica gel, glass, inert alumina, and magnetic substances. These materials may be used singly or in combination of two or more thereof.

The form of the solid phase is not particularly limited insofar as the solid phase is in the form of a usual solid phase used in immunoassays, for example in the form of a microtiter plate, a test tube, beads, particles, and nanoparticles. The particles include magnetic particles, hydrophobic particles such as polystyrene latex, copolymer latex particles having hydrophilic groups such as an amino group and a carboxyl group on the surfaces of the particles, red blood cells and gelatin particles. The solid phase is preferably a microtiter plate or strip, such as those available from Cell Signaling Technology, Inc.

The capture antibody may be one or more monoclonal anti-EDA1 antibodies described herein.

Where microtiter plates or strips are used, the capture antibody is immobilized within the wells. Techniques for coating and/or immobilizing proteins to solid phase substrates are known in the art, and can be achieved, for example, by a physical adsorption method, a covalent bonding method, an ionic bonding method, or a combination thereof. See, e.g., W. Luttmann et al., Immunology, Ch. 4.3.1 (pp. 92-94), Elsevier, Inc. (2006) and the references cited therein. For example, when the binding substance is avidin or streptavidin, a solid phase to which biotin was bound can be used to fix avidin or streptavidin to the solid phase. The amounts of the capture antibody, the detection antibody and the solid phase to be used can also be suitably established depending on the antigen to be measured, the antibody to be used, and the type of the solid phase or the like. Protocols for coating microtiter plates with capture antibodies, including tools and methods for calculating the quantity of capture antibody, are described for example, on the websites for Immunochemistry Technologies, LLC (Bloomington, Minn.) and Meso Scale Diagnostics, LLC (Gaithersburg, Md.).

The detection antibody can be any anti-EDA1 antibody. If the detection antibody is not conjugated with a detectable label or an enzyme, then a labeled secondary antibody that specifically binds to the detection antibody is included. In certain embodiments, the pair of anti-EDA1 antibodies comprises two of the anti-EDA1 antibodies described herein, such as for example, mAbEDA1-EctoD2 and mAbEDA1-EctoD3.

Techniques for labeling antibodies with detectable labels are well-established in the art. The detectable label can be selected, e.g., from a group consisting of radioisotopes, fluorescent compounds, chemiluminescent compounds, enzymes, and enzyme co-factors, or any other labels known in the art. See, e.g., Zola, Monoclonal Antibodies: A Manual of Techniques, pp. 147-158 (CRC Press, Inc. 1987). A detectable label can be attached to the subject antibodies and is selected so as to meet the needs of various uses of the method which are often dictated by the availability of assay equipment and compatible immunoassay procedures. Appropriate labels include, without limitation, radionuclides, enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Evidot® quantum dots supplied by Evident Technologies, Troy, N.Y., or Qdot™ nanoparticles supplied by the Quantum Dot Corporation, Palo Alto, Calif.).

Preferably, the sandwich immunoassay of the present invention comprises the step of measuring the labeled secondary antibody, which is bound to the detection antibody, after formation of the capture antibody-antigen-detection antibody complex on the solid phase. The method of measuring the labeling substance can be appropriately selected depending on the type of the labeling substance. For example, when the labeling substance is a radioisotope, a method of measuring radioactivity by using a conventionally known apparatus such as a scintillation counter can be used. When the labeling substance is a fluorescent substance, a method of measuring fluorescence by using a conventionally known apparatus such as a luminometer can be used.

When the labeling substance is an enzyme, a method of measuring luminescence or coloration by reacting an enzyme substrate with the enzyme can be used. The substrate that can be used for the enzyme includes a conventionally known luminescent substrate, calorimetric substrate, or the like. When an alkaline phosphatase is used as the enzyme, its substrate includes chemilumigenic substrates such as CDP-star® (4-chloro-3-(methoxyspiro(1,2-dioxetane-3,2'-(5'-chloro)tricyclo[3.3.1.1.sup.3 7]decane)-4-yl) disodium phenylphosphate) and CSPD® (3-(4-methoxyspiro(1,2-dioxetane-3,2-(5'-chloro)tricyclo [3.3.1.1.sup.3 7]-decane)-4-yl)disodium phenylphosphate) and colorimetric substrates such as p-nitrophenyl phosphate, 5-bromo-4-chloro-3-indolyl-phosphoric acid (BCIP), 4-nitro blue tetrazolium chloride (NBT), and iodonitro tetrazolium (INT). These luminescent or calorimetric substrates can be detected by a conventionally known spectrophotometer, luminometer, or the like.

In some embodiments, the detectable labels comprise quantum dots (e.g., Evidot® quantum dots supplied by Evident Technologies, Troy, N.Y., or Qdot™ nanoparticles supplied by the Quantum Dot Corporation, Palo Alto, Calif.). Techniques for labeling proteins, including antibodies, with quantum dots are known. See, e.g., Goldman et al., Phys. Stat. Sol., 229(1): 407-414 (2002); Zdobnova et al., J. Biomed. Opt., 14(2):021004 (2009); Lao et al., JACS, 128(46):14756-14757 (2006); Mattoussi et al., JACS, 122 (49):12142-12150 (2000); and Mason et al., Methods in Molecular Biology: NanoBiotechnology Protocols, 303:35-50 (Springer Protocols, 2005). Quantum-dot antibody labeling kits are commercially available, e.g., from Invitrogen (Carlsbad, Calif.) and Millipore (Billerica, Mass.).

The sandwich immunoassay of the present invention may comprise one or more washing steps. By washing, the unreacted reagents can be removed. For example, when the solid phase comprises a strip of microtiter wells, a washing substance or buffer is contacted with the wells after each step. Examples of components of the washing solution that can be used include 2-[N-morpholino]ethanesulfonate buffer (MES), or phosphate buffered saline (PBS), etc. The pH of the buffer is preferably from about pH 6.0 to about pH 10.0. The buffer may contain a detergent or surfactant, such as Tween 20.

The sandwich immunoassay can be carried out under typical conditions for immunoassays. The typical conditions for immunoassays comprise those conditions under which the pH is about 6.0 to 10.0 and the temperature is about 30 to 45° C. The pH can be regulated with a buffer, such as phosphate buffered saline (PBS), a triethanolamine hydrochloride buffer (TEA), a Tris-HCl buffer or the like. The buffer may contain components used in usual immunoassays, such as a surfactant, a preservative and serum proteins. The time of contacting the respective components in each of the respective steps can be suitably established depending on the antigen to be measured, the antibody to be used, and the type of the solid phase or the like.

Kits

The invention further provides kits for performing an immunoassay using the antibodies of the present invention. The kits comprise, at a minimum, one or more of the antibodies described herein for use as capture or detection agents for determining the presence and amount of EDA1 in a biological sample. The kit optionally may include reagents useful in performing the assay, additional antibodies for use in capture/detection of EDA1, detection reagents, blocking reagents, or washing reagents. The kits may include instructions for performing an immunoassay using the antibodies and reagents.

Pharmacokinetics, Pharmacodynamics and Methods of Treatment of Developmental Disorders One embodiment of the present invention is a method of characterizing a pharmacokinetic profile and/or a pharmacodynamic profile of a recombinant EDA1 molecule, the method comprising: a) obtaining samples from a patient at a plurality of time points after administration of the recombinant EDA1; and b) determining the quantity of recombinant EDA1 at the time points using an immunoassay comprising an antibody generated against the recombinant EDA1, thereby characterizing the pharmacokinetic profile of the recombinant EDA1 molecule.

Another embodiment of the present invention is a method for treating a patient with a developmental disorder. This method comprises a) administering recombinant EDA1 to the patient; b) characterizing a pharmacokinetic profile and/or a pharmacodynamic profile according to the method of claim 30; c) selecting a dosing regimen for recombinant EDA1 based upon the characterized pharmacokinetic profile; and d) treating the patient according to the selected dosing regimen.

The term "profile" is used according to its art accepted meaning and refers to the collection of results of one or more analyses or examinations of: (1) the presence of; or (2) extent to which an observed phenomenon exhibits various characteristics. Illustrative profiles typically include the results from a series of observations which, in combination, offer information on factors such as, for example, the presence and/or levels and/or characteristics of recombinant EDA1.

The term "dosing regimen" is used according to its art accepted meaning and refers to, for example, a treatment plan for an individual suffering from a pathological condition that specifies factors such as the dosages of recombinant EDA1, as well as the schedule and duration of the treatment.

The term "pharmacokinetics" is used according to its art accepted meaning and refers to the study of the action of drugs in the body, for example the effect and duration of drug action after administration of recombinant EDA1, the rate at which recombinant EDA1 is absorbed, distributed, metabolized, and eliminated by the body.

The term "pharmacodynamics" is used according to its art accepted meaning and refers to study of the biochemical and physiological effects of drugs on the body or on microorganisms or parasites within or on the body, the mechanisms of drug action and the relationship between drug concentration and effect (for example the study of a concentration of recombinant EDA1 present in a patient's plasma following one or more dosing regimens).

Typically, pharmacokinetic or pharmacodynamic parameters comprise a concentration of the therapeutic agent in the blood of the patient that results from the first therapeutic regimen. In certain embodiments of the invention, practitioners can then use the pharmacokinetic or pharmacodynamic parameters observed in the patient in response to the first therapeutic regimen to obtain a patient-specific regimen responsiveness profile. This patient-specific regimen responsiveness profile is based upon each patient's individualized physiology and necessarily takes into account a variety of factors. This patient-specific regimen responsiveness profile is then used to design a patient-specific dosing regimen.

By using the methods described herein to obtain patient-specific regimen responsiveness profiles which are in turn used to design a patient-specific therapeutic regimens, practitioners can reduce or avoid complications in therapy that result from individualized factors.

Embodiments of the invention can use information obtained from patient-specific regimen responsiveness profiles to design a variety of patient-specific therapeutic regimens.

In certain embodiments of the invention, measurements of phenomena such as the in vivo levels of administered recombinant EDA1 is determined. Optionally, such determinations are made 0, 1, 2, 3, 4, 6, or 7 days (i.e. week 1) after the administration of a therapeutic regimen and/or any day of weeks 2, 3, 4, 5, 6, 7, 8, 9, 10, 11, 12 etc. up to for example week 72. In one illustrative embodiment, after the initiation of a therapeutic regimen, patients can return for safety and efficacy evaluations on a weekly basis up to week 4 and every 28 days thereafter throughout a 48-week treatment duration, with weekly or monthly follow-up visits up to week 72. Optionally determinations of actual efficacy and limits of critical efficacy occur between 0 and 7 days, and more preferably around between about 0 to 2 days. Alternatively, this determination may be made intermittently throughout therapy, to take into account for example individualized patient response to various therapeutic regimens. One with ordinary skill in the art will undoubtedly realize that different pharmacokinetic and pharmacodynamic models may be used.

Certain embodiments of the invention use algorithms to obtain pharmacokinetic or pharmacodynamic parameters that comprise the patient-specific profile. Such embodiments of the invention can use one of a variety of art accepted methodologies. For example, certain embodiments of the invention can employ numerical methods with these equations and parameters. Some embodiments of the invention use analytical solutions to observe such parameters. In one illustrative embodiment of the invention, the values of such model parameters can be determined using standard nonlinear regression techniques (see, e.g. Motulsky and Christopoulos "Fitting Models to Biological Data Using Linear and Nonlinear Regression: A Practical Guide to Curve Fitting" Oxford University Press, USA; 1 edition (May 27, 2004)). Those of skill in the art understand that there are many variations of these illustrative model equations that can be used in embodiments of the invention (e.g. those having small changes such as including time delays and the like) and that such variations are contemplated and encompassed by the disclosure provided herein.

The patient-specific profiles of the invention can be used to design patient specific therapeutic regimens in a number of contexts. Those of skill in the art understand that a variety of patient-specific factors can be observed as part of a profile. For example, certain embodiments of the invention include observing additional patient-specific factors to those discussed above (e.g. "surrogate" PK markers such as PD marker molecules that are altered in response to administration of recombinant EDA1).

Once a first patient-specific regimen is designed and administered, practitioners can then obtain a further patient-specific regimen responsiveness profile that results from the administration first patient-specific regimen. Such further patient-specific regimen responsiveness profile can then be used to design further patient-specific regimens. For example, certain embodiments of the invention comprise obtaining pharmacokinetic or pharmacodynamic parameters from the patient so as to observe a patient-specific response to the first patient-specific therapeutic regimen as discussed above., wherein the pharmacokinetic or pharmacodynamic parameters comprise at least one of: a concentration of administered EDA1 in the plasma of the patient; using the pharmacokinetic or pharmacodynamic parameters observed in the patient in response to the first patient-specific therapeutic regimen to obtain a second patient-specific regimen responsiveness profile; and using the second patient-specific regimen responsiveness profile to design a second (or third or fourth etc.) patient-specific therapeutic regimen.

Effective regimens for dosing a patient with recombinant EDA1 are adjusted, based upon the pharmacokinetic and/or pharmacodynamic profiles determined as described herein to provide the optimum desired response (e. g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of recombinant EDA1 can be varied so as to obtain an amount of the active ingredient which is effective to achieve the desired therapeutic response for a particular patient, composition, and mode of administration, without being toxic to the patient. The selected dosage level depends upon a variety of pharmacokinetic and/or pharmacodynamic factors including the activity of the particular compositions of the present invention employed, or the salt or amide thereof, the route of administration, the time of administration, the duration of the treatment, other drugs, compounds and/or materials used in combination with the particular compositions employed, the age, sex, weight, condition, general health and prior medical history of the patient being treated, and like factors.

A physician or veterinarian can start doses of recombinant EDA1 at levels lower than that required to achieve the desired therapeutic effect and gradually increase the dosage until the desired effect is achieved. In general, a suitable daily dose of a composition of the invention is that amount of the compound which is the lowest dose effective to produce a therapeutic effect. Such an effective dose generally depends upon the factors described above. It is preferred that administration be intravenous, intramuscular, intraperitoneal, or subcutaneous, or administered proximal to the site of the target. If desired, the effective daily dose of a therapeutic composition can be administered as two; three, four, five, six or more sub-doses administered separately at appropriate intervals throughout the day, optionally, in unit dosage forms.

It is thus demonstrated that certain aspects of the present invention have important implications for the design of novel treatment strategies.

Methods for Producing Isolated Monoclonal Anti-EDA1 Antibodies

In one embodiment, the present invention concerns a method for producing anti-EDA1 monoclonal antibodies or isolated monoclonal antibody fragments or antigen binding portions or fragments thereof comprising the steps of: producing EDA1 antigen, or EDA1 fragment, or EDA1 fusion protein of mouse and/or human and/or vertebrate species; immunizing EDA1-deficient mice with said EDA1 antigen or EDA1 fragment, or EDA1 fusion protein; detecting anti-EDA1 antibodies in the serum of said EDA1 antigen or EDA1 fragment, or EDA1 fusion protein-immunized EDA1-deficient mice; producing hybridomas between lymph node cells from EDA1 antigen or EDA1 fragment, or EDA1 fusion protein-immunized, EDA1-deficient mice and myeloma cells; identifying anti-EDA1 antibodies or isolated monoclonal antibody fragments or antigen binding portions or fragments thereof recognizing human and/or mouse and/or avian EDA1 and/or EDA1 from vertebrate species i. by binding assays designed to detect binding between the antagonist anti-EDA1 antibodies or isolated monoclonal antibody fragments or antigen binding portions or fragments thereof and human and/or mouse and/or avian EDA1 antigen or EDA1 fragment, or EDA1 fusion protein; and ii. for their ability to block binding of recombinant EDA1 to recombinant EDAR in an in vitro assay and iii. for their ability to inhibit the response induced by EDA1 in cells expressing an EDAR:Fas fusion protein in vitro iv. for their ability to block the biological response induced by recombinant EDA1 in EDA-deficient mice v. for their ability to induce a biological response in vivo in organisms expressing EDA1 characterized by the effect of EDA1 inhibition; selecting hybridoma lines for the antagonist anti-EDA1 monoclonal antibodies produced by the hybridoma lines on the basis of the results of steps e) ii and e) iii; cloning and sub-cloning the selected hybridoma lines; and purifying the resulting antagonist anti-EDA1 monoclonal antibodies or isolated monoclonal antibody fragments or antigen binding portions or fragments thereof.

In certain embodiments, the EDA1 antigen of step a) is human EDA1, or mouse EDA1, or EDA1 from another mammalian species, or EDA1 from another vertebrate species.

In certain embodiments, the EDA1 antigen of step a) is a cell line naturally expressing full length EDA1 or transfected with full length EDA1, or the EDA1 antigen is a soluble EDA1 fragment, or the EDA1 antigen is a fusion protein between the extracellular domain of EDA1 and another protein, or the EDA1 antigen is part of a virus-like particle.

In certain embodiments, the EDA1 antigen is human or mouse EDA1 fused to the Fc portion of human IgG1, (a molecule known as Fc-EDA1) as described, for example, in Gaide et al., *Nature Med.*, 2003, 9(5), 614-618, which is incorporated herein by reference in entirety.

As an alternative to steps b), c) and d), anti-EDA1 antibodies, or fragments thereof such as single chain Fvs can be obtained by selecting antibody sequences by phage display on the antigen of step a).

In certain embodiments, the binding assays of step e) is carried out by applying visualizing methods comprising ELISA, dot blot, Western blot, RIA, immunoprecipitation, flow cytometry, fluorescence microscopy, electron microscopy, confocal microscopy, calorimetry, plasmon resonance, test of Ouchterlony, complement-mediated lysis of red blood cells, antibody-dependent cell cytotoxicity and the like.

In certain embodiments, the binding assays of step e) i is carried out by direct or capture enzyme-linked immunosorbent assay (ELISA).

In certain embodiments, the biological in vitro assay of step e) ii is the measure of inhibition of placode formations in embryonic skin of WT mouse embryos ex vivo (Mustonen et al. "Ectodysplasin A1 promotes placodal fate during early morphogenesis of ectodermal appendages," *Development* 2004, 131:4907-4919, incorporated herein by reference in entirety), the measure of inhibition of EDA-induced NF-κB activation in EDAR-positive cells, or the measure of the inhibition of EDA-induced apoptosis of Fas-deficient Jurkat cells transduced with chimeric human and/or mouse EDAR-Fas receptor.

In certain embodiments, the biological in vitro assay of step e) ii is the measure of the inhibition of EDA-induced apoptosis of Fas-deficient Jurkat cells transduced with chimeric human and/or mouse EDAR-Fas receptor.

The biological in vivo assay of step e) iii is the measure of reduction of guard hair formation and/or the measure of reduction of retroauricular hair formation and/or the measure of disruption of functional sweat glands and/or the measure of reduction of fur upon administration to developing wild-type mice (e.g. by repeated ip or iv administration of the antibody in pregnant mice, followed by repeated administration of the antibody in the newborn pups).

In some embodiments, the purification of step h) is carried out by protein A or G affinity chromatography or by protein L, anti-mouse IgG antibody-based affinity chromatography, ion exchange, ethanol or ammonium sulfate precipitation and the like.

Methods for preparing an immunogen and immunizing an animal are well-known in the art (Kohler and Milstein 1975 *Nature* 256:495-497; Brown et al. 1981 *J Immunol* 127:539-46; Brown et al., 1980 *J Biol Chem* 255:4980-83; Yeh et al., 1976 *Proc Natl Acad Sci USA* 76:2927-31; Yeh et al., 1982 *Int J Cancer* 29:269-75; Kozbor et al., 1983 *Immunol Today* 4:72; Cole et al., 1985 Monoclonal Antibodies and Cancer Therapy, Alan R. Liss, Inc., pp. 77-96; U.S. Pat. No. 4,816,567; Clackson, et al., 1991 *Nature* 352:624-628; Marks, et al., 1991 *J Mol Biol* 222:581-597).

Pharmaceutical Compositions and Treatments

In another aspect, the present invention provides a pharmaceutical composition comprising the isolated antagonist anti-EDA1 monoclonal antibodies or isolated monoclonal antibody fragments or antigen binding portions or fragments thereof and a pharmaceutically acceptable carrier. The pharmaceutical composition comprises at least a therapeutically effective quantity or amount of the substantially purified and isolated antagonist anti-EDA1 monoclonal antibodies or isolated monoclonal antibody fragments or antigen binding portions or fragments thereof according to the present invention.

The isolated antagonist anti-EDA1 monoclonal antibodies or isolated monoclonal antibody fragments or antigen binding portions or fragments thereof described herein as the "compound" may be administered with a physiologically acceptable carrier. A physiologically acceptable carrier is a formulation to which the compound can be added to dissolve it or otherwise facilitate its administration. An important factor in choosing an appropriate physiologically acceptable carrier is selecting a carrier in which the compound remains active or the combination of the carrier and the compound produces an active compound. Usually, the pharmaceutically acceptable carrier can be a solvent or dispersion medium. Examples of suitable aqueous and nonaqueous carriers which may be employed in the pharmaceutical composition of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of emulsifying agents such as lecithin, by the maintenance of the required particle size in the case of dispersions, and by the use of surfactants, such as Tween 20.

The pharmaceutical composition may also contain adjuvants such as preservatives, wetting agents, emulsifying agents, pharmaceutically-acceptable antioxidants and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutically acceptable salts of the isolated antagonist anti-EDA1 monoclonal antibodies or isolated monoclonal antibody fragments or antigen binding portions or fragments thereof according to the present invention may also be envisioned.

A "pharmaceutically acceptable salt" refers to a salt that retains the desired biological activity of the parent compound and does not impart any undesired toxicological effects (see for example, Berge, S. M., et al. (1977) *J. Pharm. Sci.* 66: 1-19).

In a preferred embodiment, the pharmaceutical composition of the invention is formulated for parenteral, intravenous, oral, subcutaneous, intradermal, intramuscular or topical, administration.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Preferred routes of administration for the isolated antagonist anti-EDA1 monoclonal antibodies or isolated monoclonal antibody fragments or antigen binding portions or fragments thereof according to the present invention are intravenously, intramuscularly and intraperitoneally. Preferred modes of delivery are by injection and infusion.

Injectable forms may include sterile aqueous solutions or dispersions. Furthermore, form of sterile powders may be prepared for the extemporaneous preparation of such sterile injectable solutions or dispersions. In all cases, the final injectable form must be sterile and must be effectively fluid for easy syringability. The pharmaceutical composition must be stable under the conditions of manufacture and storage; thus, preferably should be preserved against the contaminating action of microorganisms such as bacteria and fungi.

Medicaments for parenteral administration may be prepared as solutions or suspensions of the combined components in physiological solution. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

In preparing oral dosage forms, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or non-aqueous techniques.

A tablet may be prepared by compression or molding, optionally with one or more accessory ingredients or adjuvants. Compressed tablets may be prepared by compressing, in a suitable machine, the combined components in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Effective dosage regimens are adjusted to provide the optimum desired response (e. g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Regardless of the route of administration selected, the isolated antagonist anti-EDA1 monoclonal antibodies or isolated monoclonal antibody fragments or antigen binding portions or fragments thereof according to the present invention, which may be used in a suitable hydrated form, and/or the pharmaceutical composition of the present invention, are formulated into pharmaceutically acceptable dosage forms by conventional methods known to those of skill in the art.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the salt or amide thereof, the route of administration, the time of administration, the duration of the treatment, other drugs, compounds and/or materials used in combination with the particular compositions employed, the age, sex, weight, condition, general health and prior medical history of the patient being treated, and like factors.

A physician or veterinarian can start doses of the compounds of the invention-employed in the pharmaceutical composition at levels lower than that required to achieve the desired therapeutic effect and gradually increase the dosage until the desired effect is achieved. In general, a suitable daily dose of a composition of the invention is that amount of the compound which is the lowest dose effective to produce a therapeutic effect. Such an effective dose generally depends upon the factors described above. It is preferred that administration be intravenous, intramuscular, intraperitoneal, or subcutaneous, or administered proximal to the site of the target. If desired, the effective daily dose of a therapeutic composition can be administered as two; three, four, five, six or more sub-doses administered separately at appropriate intervals throughout the day, optionally, in unit dosage forms. While it is possible for the isolated antagonist anti-EDA1 monoclonal antibodies or isolated monoclonal antibody fragments or antigen binding portions or fragments thereof according to the present invention to be administered alone, it is preferable to administer the latter as a pharmaceutical formulation (composition).

Effective doses of the compositions of the present invention, for the treatment of immune-related conditions and diseases described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1 to 10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of anti-EDA1 antibodies in the patient. In some methods, dosage is adjusted to achieve a plasma antibody concentration of 0.001-1000 μg/mL. Alternatively, antibody can be administered as a sustained release formulation, in which case less frequent administration is required.

Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The dosage ranges of the isolated antagonist anti-EDA1 monoclonal antibodies or isolated monoclonal antibody fragments or antigen binding portions or fragments thereof according to the present invention may vary with the administration routes, as well as the state of the patient (age, sex, body weight, extent of the disease etc.). Ideally, the isolated antagonist anti-EDA1 monoclonal antibodies or isolated monoclonal antibody fragments or antigen binding portions or fragments thereof is administered to a patient in need thereof at a dosage unit from 0.1 mg/kg of body weight to 100 mg/kg of body weight.

The present invention has important implications for the design of novel treatment strategies of patients suffering from conditions arising from excessive EDA1 activity, such as sebaceous gland hyperplasia, hyperhidrosis, hirsutism, skin disorders such as comedones, milia, acne, seborrhea, rosacea, steatoma, and furuncles, or certain types of cancers such as breast cancer and dermal eccrine cylindroma.

The present invention also concerns the use of the isolated antagonist anti-EDA1 monoclonal antibodies or isolated monoclonal antibody fragments or antigen binding portions or fragments thereof or the pharmaceutical composition of the invention, for the preparation of a medicament for modulating the development of cells or tissues of ectodermal origin, such as hair, teeth, skin, sweat glands, sebaceous glands, larynx and trachea mucus-producing cells, Meibomian glands, preputial glands, mammary glands and salivary glands.

In the present invention, the term "modulating" refers to a molecule which is capable to interact with a specific receptor and to modify or control its activity.

The medicament according to the invention can be used for the treatment of disorders relating to excessive activity of EDA1 such as sebaceous gland hyperplasia, hyperhidrosis, hirsutism, skin disorders such as comedones, milia, acne, seborrhea, rosacea, steatoma, and furuncles, or certain types of cancers such as breast cancer and dermal eccrine cylindroma.

In one embodiment, the medicament may be administered to the mother/the mother animal during pregnancy. Injection of the medicament to the fetus, may be carried out either directly, following the same routes as identified above (parenterally, intravenously, orally, subcutaneously, intradermally, intramuscularly or topically) or alternatively through the umbilical vein.

In another embodiment of the invention, the medicament may be administered to a pre-term newborn, a newborn, a child, a young adult or an adult.

Additionally, the present invention pertains to a pharmaceutical kit comprising at least an effective amount of the isolated antagonist anti-EDA1 monoclonal antibodies or isolated monoclonal antibody fragments or antigen binding portions or fragments thereof or the pharmaceutical composition of the invention, together with instructions for use and in particular instructions directed to the treatment of disorders arising from excessive action of EDA1, such as sebaceous gland hyperplasia, hyperhidrosis, hirsutism, skin disorders such as comedones, milia, acne, seborrhea, rosacea, steatoma, and furuncles, or certain types of cancers such as breast cancer and dermal eccrine cylindroma.

The pharmaceutical kit according to the present invention may comprise a container comprising at least the isolated antagonist anti-EDA1 monoclonal antibodies or isolated monoclonal antibody fragments or antigen binding portions or fragments thereof. The kit may include a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The label or package insert indicates that the composition is used for treating the condition of choice, such as sebaceous gland hyperplasia, hyperhidrosis, hirsutism, skin disorders such as comedones, milia, acne, seborrhea, rosacea, steatoma, and furuncles, or certain types of cancers such as breast cancer and dermal eccrine cylindroma.

Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Antagonist anti-EDA1 antibodies that cross-react with mouse and human EDA1 are expected to also cross-react with EDA1 of most mammalian species, and also with EDA1 of other vertebrate species. If the antagonist antibodies do not cross-react with EDA1 of a given mammalian or vertebrate species, it is possible to generate them according to the process described in this application by immunizing mice with an EDA1 antigen in which the EDA1 sequence corresponds to that of the species of interest.

Finally, another aspect of the invention is the use of the isolated antagonist anti-EDA1 monoclonal antibodies or isolated monoclonal antibody fragments or antigen binding portions or fragments thereof or the pharmaceutical composition of the invention, for the manufacture of a medicament for use in veterinary applications in any mammal or vertebrate species. The medicament can be utilized in utero (for mammals) or in ovo (for example, in birds, reptiles, egg-laying fishes and the like), or in young animals, or in adult animals. The treatment can be used to modulate the development of cells or tissues of ectodermal origin, such as hair, feathers, scales, horns, claws, beaks, teeth, skin, sweat glands, sebaceous glands, larynx and trachea mucus-producing cells, meibomian glands, preputial glands, mammary glands and salivary glands, In particular, the treatment can be used to temporarily or permanently modify hair, scale or feathers color and/or morphology.

EXAMPLES

The foregoing description will be more fully understood with reference to the following examples. These examples, are, however, exemplary of methods of making and using certain aspects of the present invention and are not intended to impose limits on the scope of the invention as defined by the appended claims.

Example 1

Generation of Monoclonal Antibodies Against Fc-EDA1

To generate monoclonal antibodies against Fc-EDA1, Tabby mice were immunized with Fc-EDA1 (also known in the art as EDI200 and APO200). Hybridomas were generated by existing methods. Supernatants were screened using both a direct ELISA and a competition ELISA. Several anti-EDA1 antibodies were identified (2 of which, EctoD2 and EctoD3, were found to be capable of blocking EDA1). Several hybridomas were subcloned using existing methods. Hybridomas of mAbEDA1-EctoD1 (VF12H6), mAbEDA1-EctoD2 (IID12E10) and mAbEDA1-EctoD3 were amplified in DMEM-10% FCS, Hepes, β-mercaptoethanol, and Hybridokine (Uptima), then washed and passed in OptiMEM for protein secretion. Supernatants were purified with Protein A-Sepharose (all done at Adipogen). mAbEDA1-EctoD1 (#1204-24) and mAbEDA1-EctoD2 (#1204-25) were prepared at a concentration of 2 mg/mL in PBS and loaded on a reducing (DTT) SDS-PAGE and followed by staining with Coomassie Blue. Results are shown in FIG. 1. It was found that similar amounts of both antibodies with light and heavy chains were obtained. Subcloning was successful for 3 antibodies, mAbEDA1-EctoD1, mAbEDA1-EctoD2 and mAbEDA1-EctoD3. cDNAs were prepared and the antibody sequences were determined About 10 mg each of antibodies mAb EctoD1, EctoD2 and EctoD3 were produced.

Example 2

Testing of Anti-EDA1 Antibodies by Direct and Competition ELISA

Figure 2:
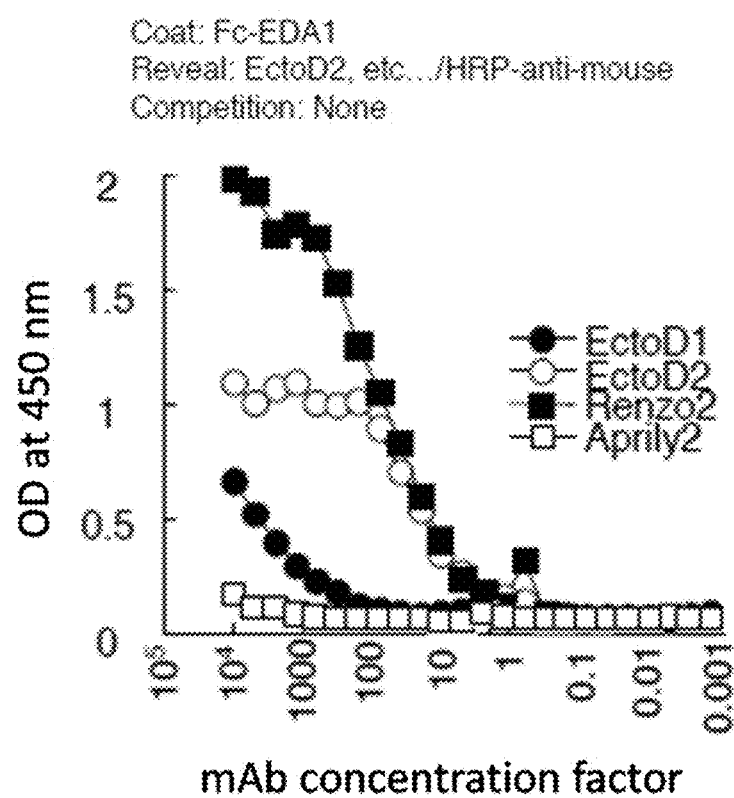
FIG. 2. Results of a direct ELISA for detection of Fc-EDA1 with mAbEDA1-EctoD1 and mAbEDA1-EctoD2 and positive and negative control antibodies (Renzo2 and Aprily2, respectively).

In a direct ELISA test, 100 µl of APO200 (#0701) (a version of Fc-EDA1) was coated on plates at 1 µg/mL in PBS, followed by blocking. Then 100 µL of mAbEDA1-EctoD1, mAbEDA1-EctoD2, Renzo2 (a control antibody capable of binding to EDA1) or Aprily2 (a control antibody which does not bind to EDA1) were added at 10 µg/mL in incubation buffer. Two-fold dilutions were performed directly in the coated plate. Binding was then revealed with anti-mouse HRP (⅕₀₀₀) followed by addition of the substrates OPD and $H_2O_2$. The results are shown in FIG. 2 which shows a plot of detection of the HRP reaction (indicating reactivity of the anti-EDA1 antibodies vs. the concentration factor of the tested monoclonal antibodies. It can be seen that there is little reactivity with mAbEDA1-EctoD1. On the other hand, mAbEDA1-EctoD2 binds to Fc-EDA1 with an EC50 value similar to that of Renzo2, but with less signal at saturation.

Figure 3:
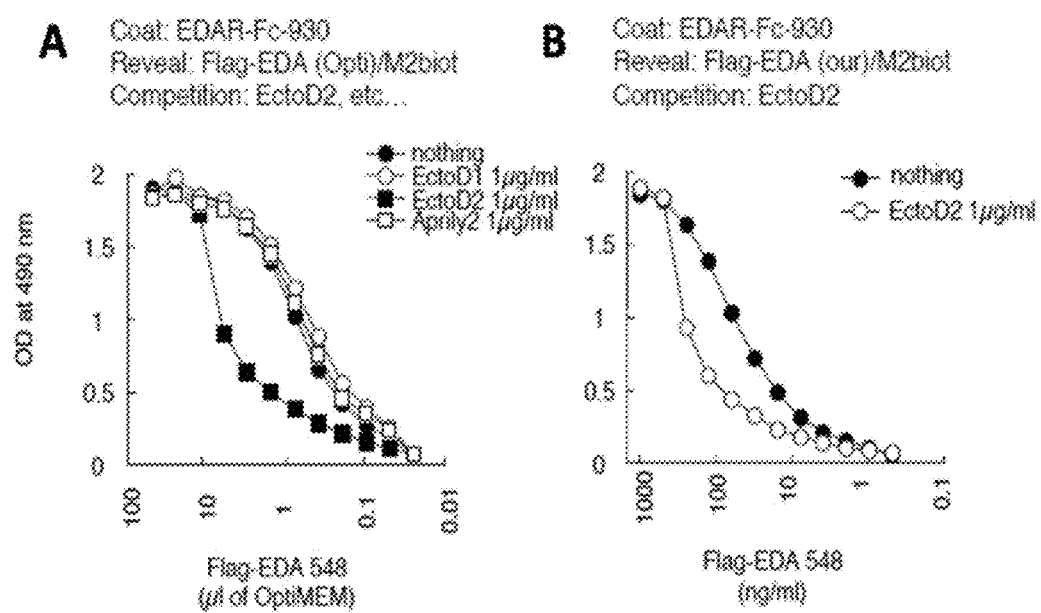
FIG. 3. Results of a competition ELISA between EDAR-Fc-930 and FLAG-EDA (the latter present in conditioned supernatant of transfected cells) in the presence of mAbEDA1-EctoD1 and mAbEDA1-EctoD2, Aprily2 and a negative control (panel A). Panel B shows a comparison of the negative control with mAbEDA1-EctoD2 using purified FLAG-EDA.
Figure 4:
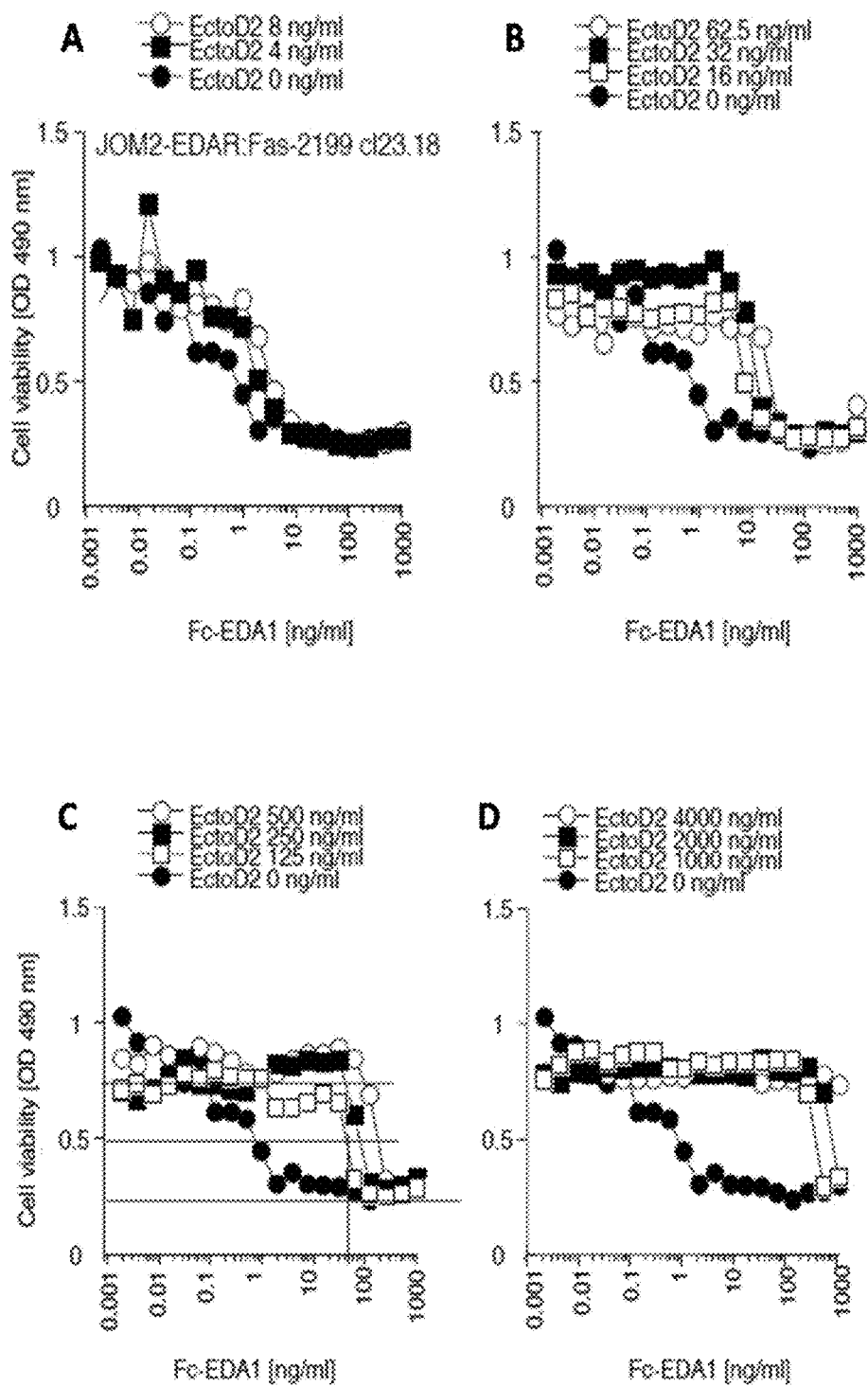
FIG. 4. Results of a cytotoxicity assay for determination of binding sites on Fc-EDA1 and mAbEDA1-EctoD2 using EDAR-Fas Jurkat cells. Each of the curves shown in panels A to D is a titration of Fc-EDA1 in the presence of a fixed concentration of antiEDA1-EctoD2 antibody (0, 4, 8, 16, 32, 62.5, 125, 250, 500, 1000, 2000 and 4000 ng/ml, as indicated).

In a competition ELISA test, 100 µL of 1 µg/mL hEDAR-Fc-930 (#1106-30) in PBS was coated on plates, followed by blocking. Two-fold dilutions of Flag-EDA1-548 OptiMEM (#811-10) or purified Flag-EDA-548 (#1111-01) were made in incubation buffer containing nothing (control), 1 µg/mL of mAbEDA1-EctoD1 (clone VF12H6) (#1204-24), 1 µg/mL of mAbEDA1-EctoD2 (clone 2D12E10) (#1204-25) or 1 µg/mL of Aprily2 (#1205-04), so that the first final concentration of optiMEM Flag-EDA was 0.5-fold concentrated and the first final concentration of purified Flag-EDA1 was 1000 ng/mL. The solutions were incubated for 2 hours at room temperature. The solutions were then added to the coated plates. Binding was revealed with anti-Flag M2-biot (⅕₀₀₀) followed by streptavidin-HRP (⅕₀₀₀). The results (see FIGS. 3A and 3B) indicate that mAbEDA1-EctoD2 inhibits the binding of Flag-EDA1 to EDAR-Fc. This does not occur for Aprily2 or mAbEDA1-EctoD1. Stoichiometry cannot be determined from this experiment because the Flag-EDA1 concentration in OptiMEM is not known, and because the concentration of pure Flag-EDA1 is probably underestimated because the protein is not entirely pure. In any case, the results of this experiment indicate that purified mAbEDA1-EctoD2 blocks EDA1.

Example 3

Determination of Binding Sites on mAbEDA1-EctoD2 and Fc-EDA1

Figure 5:
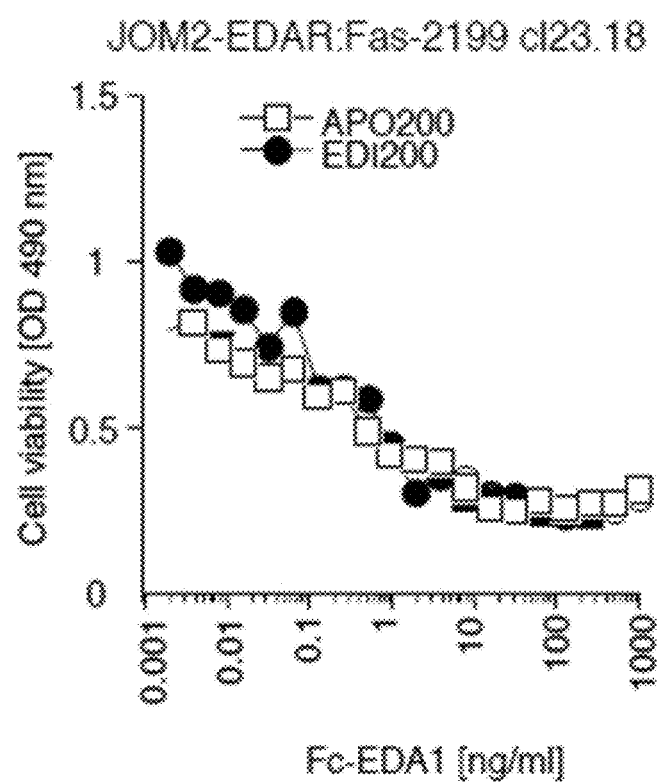
FIG. 5. Results of the same cytotoxicity assay described for FIG. 4 with a comparison of APO200 and EDI200 which represent two different lots of Fc-EDA1 (a recombinant form of EDA1).

A cytotoxicity assay using EDAR-Fas Jurkat cells was performed to determine the stoichiometry of inhibition of mAbEDA1-EctoD2 on Fc-EDA1. The procedure used for this cytotoxicity assay has been described in Schneider et al., *J. Exp. Med.* 1998, 187, 1205-1213, which is incorporated herein by reference in entirety. Briefly, medium containing mAbEDA1-EctoD2 (#1204-24) at 8 µg/mL was prepared with a series of 2-fold dilutions. For each of these solutions, 98 µL was added to well 1, and 50 µL was added to wells 2-20. In well 1, 2 µL of Fc-EDA1 (GMP2 #11-0015 filter flush) at 100 µg/mL (–>2000 ng/mL) was added. For a comparison, APO200 (#0701) was also titrated. A 50 µL volume of cells (JOM2-EDAR:Fas-2199 c123 sc18) (-->1st final concentration of EctoD2=4000 ng/mL; the first concentration of Fc-EDA1=1000 ng/mL) was incubated O/N. Cell viability was monitored with the PMS/MTS viability test. The results, shown in FIGS. 4A-4D indicate that when more mAbEDA1-EctoD2 is present, additional Fc-EDA1 inhibition is obtained. For mAbEDA1-EctoD2 at 125 ng/mL, 40 ng/mL of Fc-EDA1 is completely inhibited. FIG. 5 indicates that there is no difference between APO200 and EDI200 (these are two different preparations of Fc-EDA1). Considering that i. a concentration of 125 ng/ml mAb is approximately equal to 0.8 nM, that ii. a concentration of 40 ng/mL Fc-EDA1 is approximately equal to 0.15 nM, that iii. an antibody has 2 binding sites, that iv. Fc-EDA1, which is a hexamer, displays 6 epitopes for the antibody, it is concluded that there are about 5 antibodies per APO200 or EDI200, i.e. about 10 binding sites for 6 epitopes. Therefore, inhibition of Fc-EDA1 by EctoD2 is close to stoichiometric.

Example 4

Figure 6:
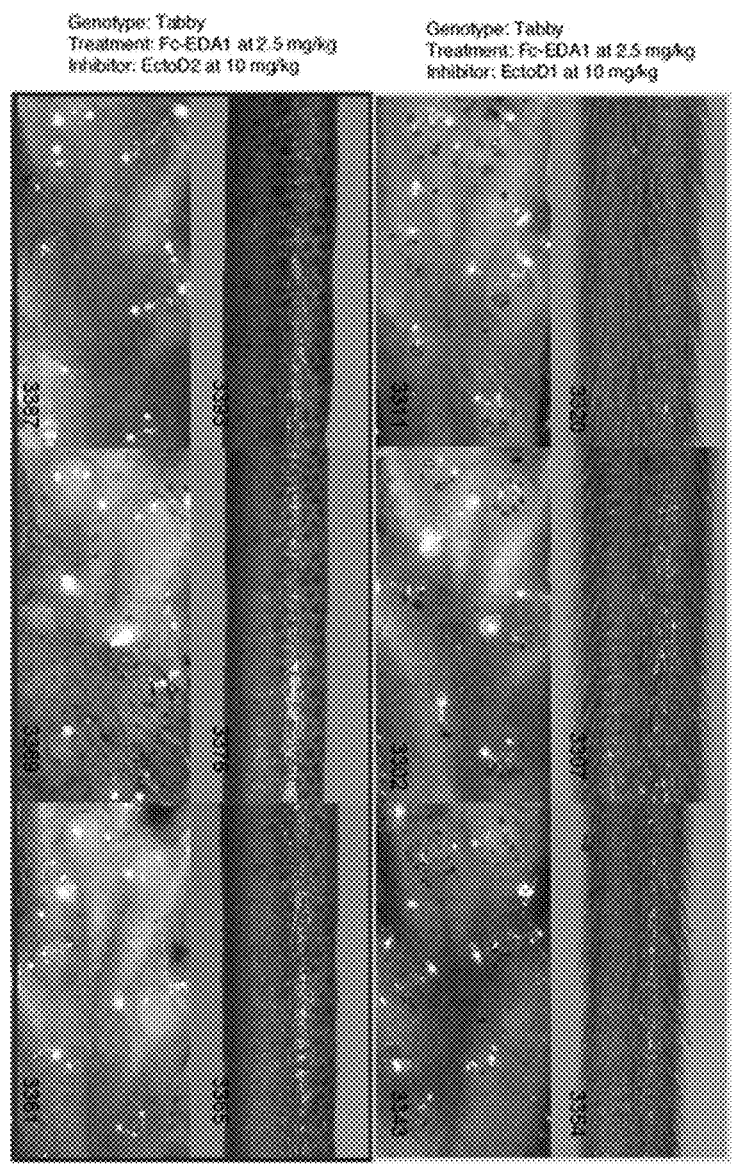
FIG. 6. Photographs of tail hair and sweat glands of Tabby mice treated with Fc-EDA1 at 2.5 mg/kg pre-mixed before administration with an excess (10 mg/kg) of mAbEDA1-EctoD1 and mAbEDA1-EctoD2. In this assay, the presence of tail hair and of sweat glands indicate that Fc-EDA1 could exert its activity unimpaired.

Analysis of the Effects of Administration of mAbEDA1-EctoD1 and mAbEDA1-EctoD2 to Tabby Mice The Tabby mouse phenotype is similar to the phenotype exhibited by humans with XLHED. Newborn Tabby mice were treated with Fc-EDA1 (#0701) at 2.5 mg/kg premixed with mAbEDA1-EctoD1 (#1204-25) at 10 mg/kg or mAbEDA1-EctoD2 (#1204-25) at 10 mg/kg. At day 23, mice were analyzed for the presence of tail hair and functional sweat glands. The results are shown in FIG. 6 where photographs of tails and sweat glands are shown. All three of the mice treated with Fc-EDA1 and non-blocking mAb EctoD1 have tail hair and sweat glands, indicating that there is a shift toward a normal phenotype as a result of administration of Fc-EDA1. Therefore, mAbEDA1-EctoD1 does not block the action of Fc-EDA1. All four of the mice treated with the combination of Fc-EDA1 and mAbEDA1-EctoD2 were found to resemble the Tabby phenotype. This indicates that the action of Fc-EDA1 is blocked by mAbEDA1-EctoD2. A 4-fold mass excess of mAbEDA1-EctoD2 is sufficient to completely block the in vivo activity of Fc-EDA1.

Example 5

Figure 7:
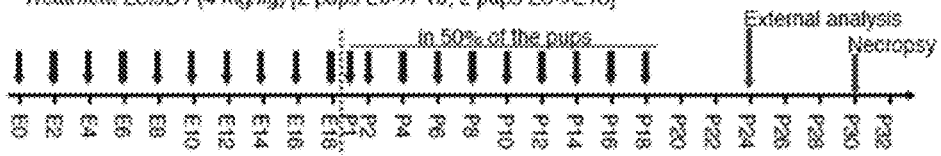
FIG. 7. Schematic representation of the treatment regimen used for blocking endogenous EDA1 in developing WT mice with mAbEDA1-EctoD1, mAbEDA1-EctoD2 and mAbEDA1-EctoD3.
Figure 7:
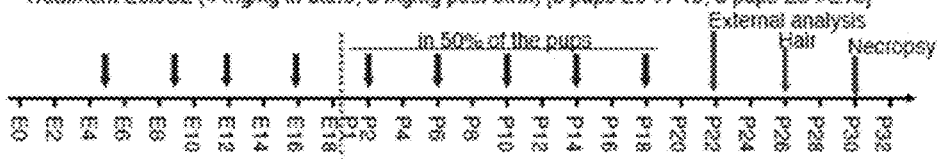
Figure 7:
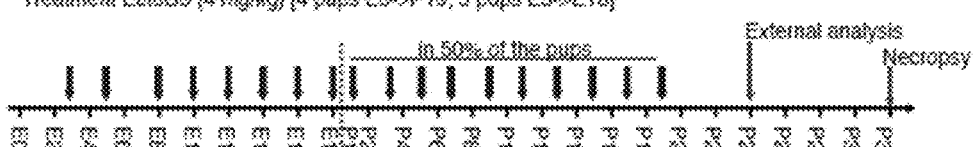
Figure 7:
Figure 8:
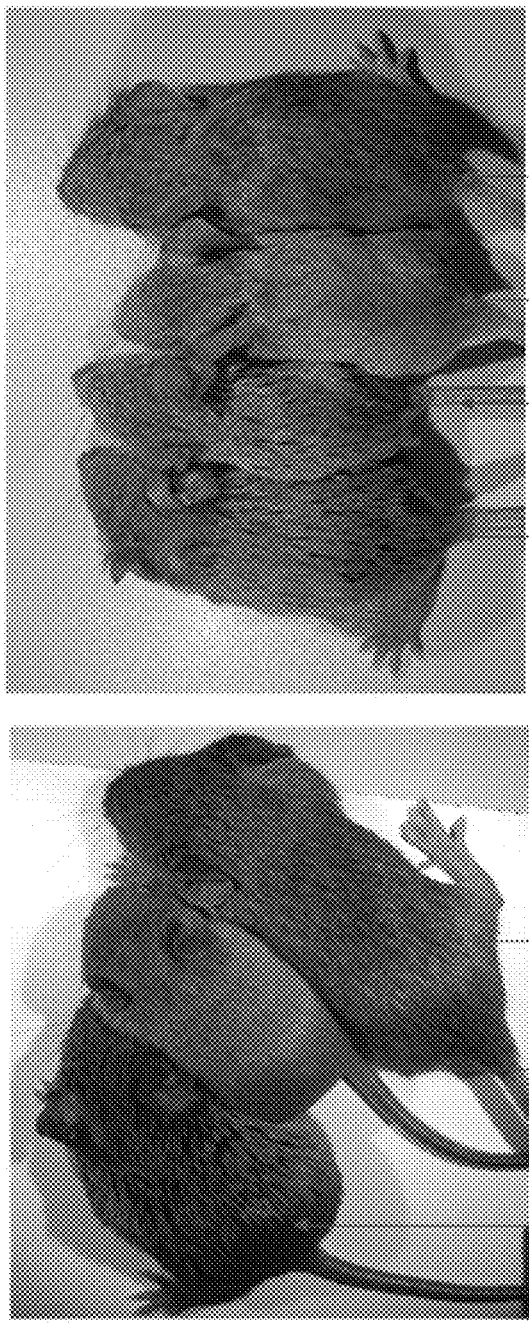
FIG. 8. Photographs of Tabby mice, wild-type mice treated with mAbEDA1-EctoD2 or mAbEDA1-EctoD3, and untreated wild-type mice.
Figure 9:
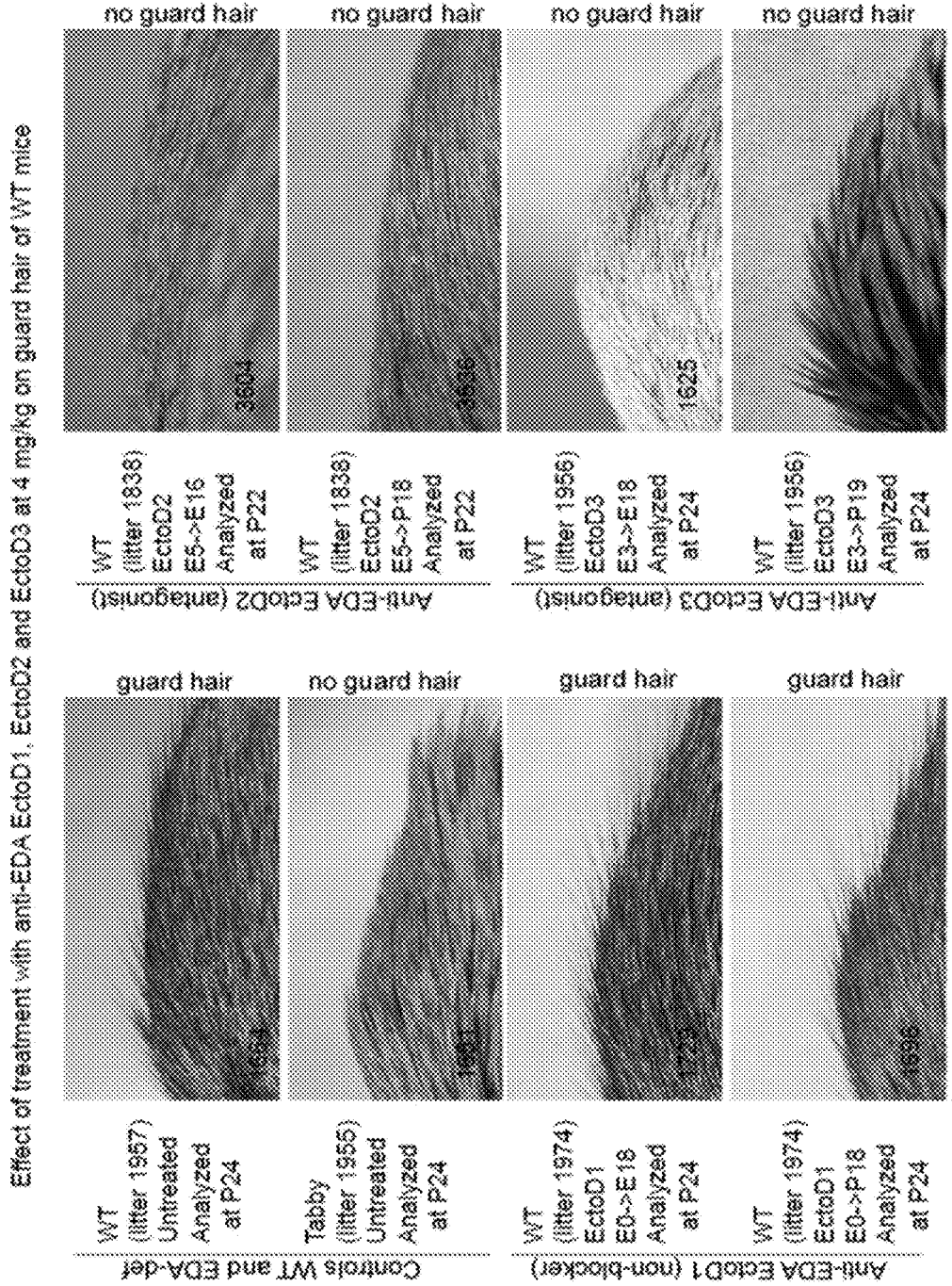
FIG. 9. Photographs of guard hair of an untreated wild-type control mouse, and untreated Tabby mouse, and wild-type mice treated with mAbEDA1-EctoD1, mAbEDA1-EctoD2 or mAbEDA1-EctoD3 in utero only (until E16 to E18, as indicated), or in utero and with continuing treatment after birth (until P18 to P19, as indicated). Pictures are representative of two (mAbEDA1-EctoD1) to three (mAbEDA1-EctoD2) to four (mAbEDA1-EctoD3) mice per group with similar results. WT mice have long guard hair protruding out of the hair coat. Tabby mice lack guard hair.
Figure 10:
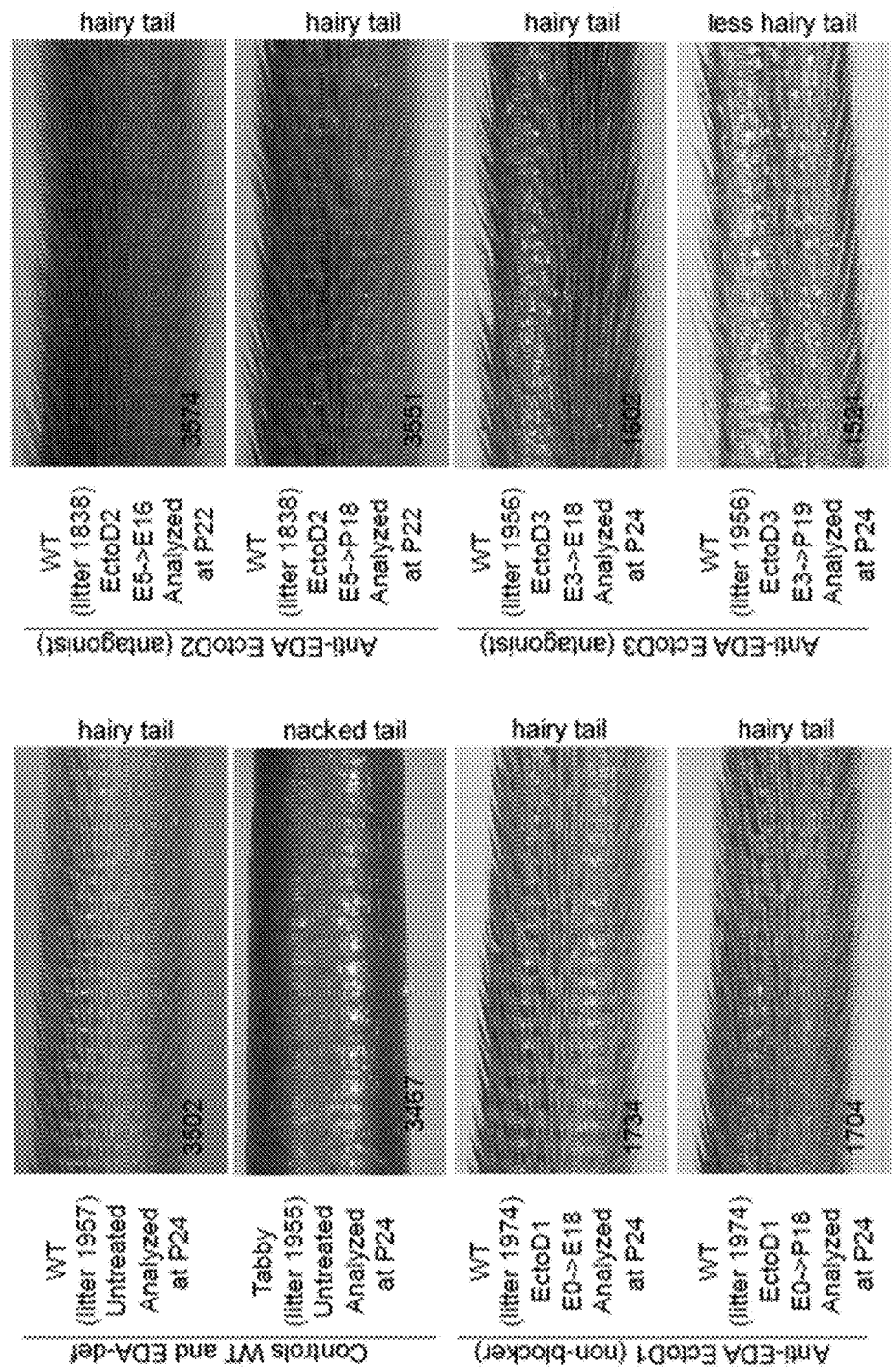
FIG. 10. Photographs of tail hair of the same mice shown in FIG. 9. WT mice have hairy tails, Tabby mice have a nacked tail.
Figure 11:
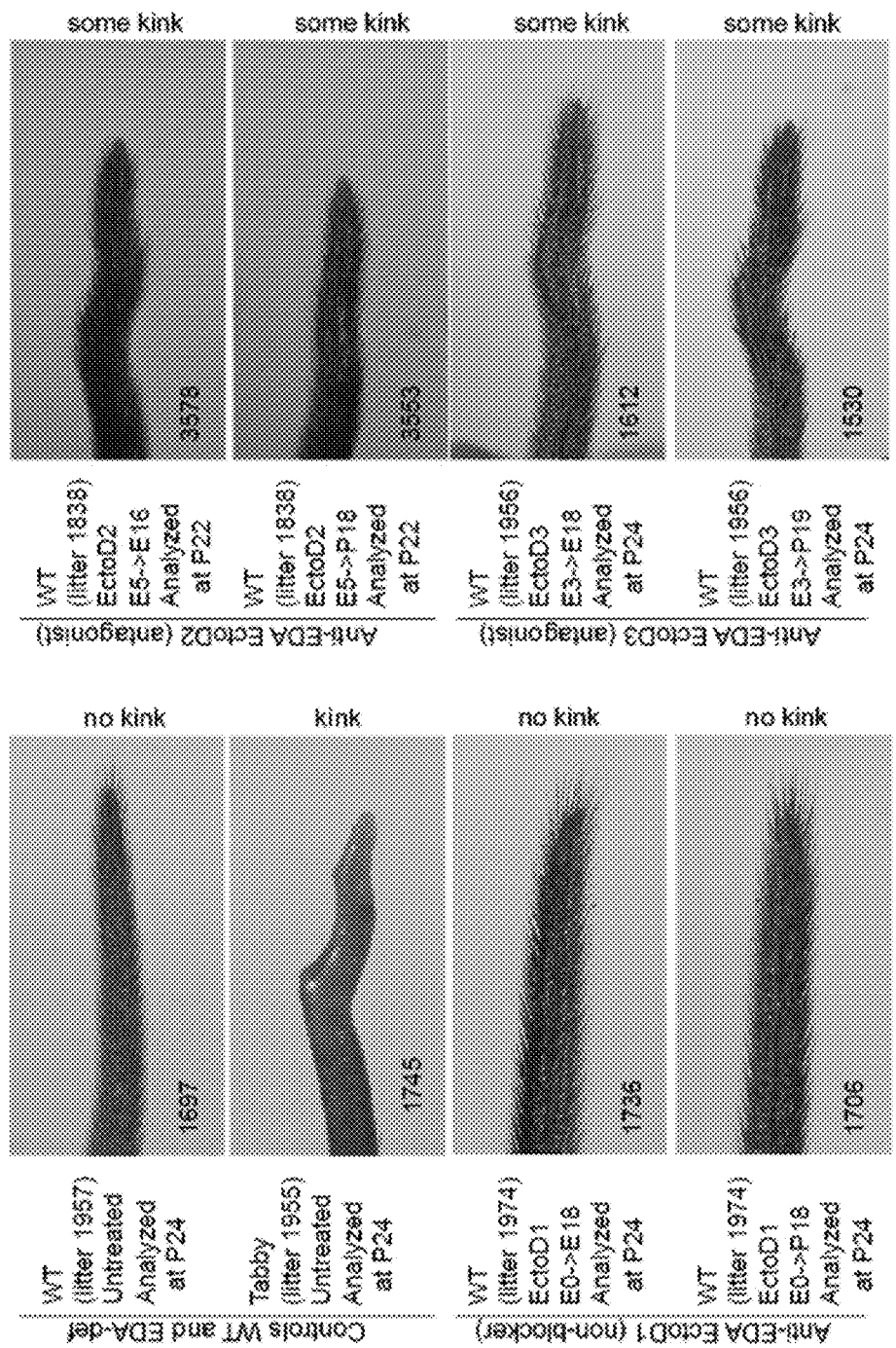
FIG. 11. Photographs of the tip of the tail of the same mice shown in FIG. 9. WT mice never present kinks. Tabby mice very often have kinks of variable shapes.
Figure 12:
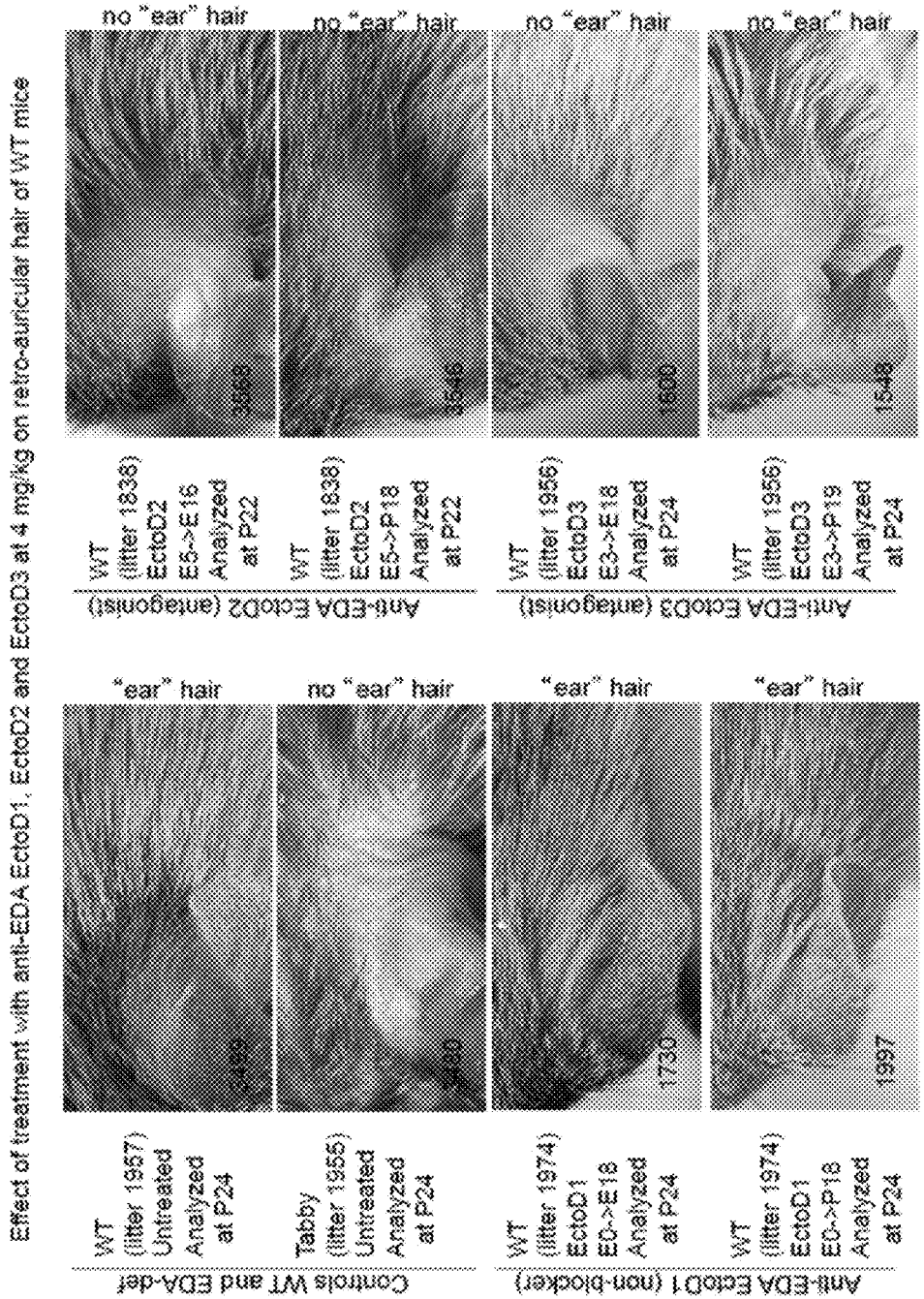
FIG. 12. Photographs of the ear region of the same mice shown in FIG. 9. WT mice have fine hair behind ears. Tabby mice lack this type of hair.
Figure 13:
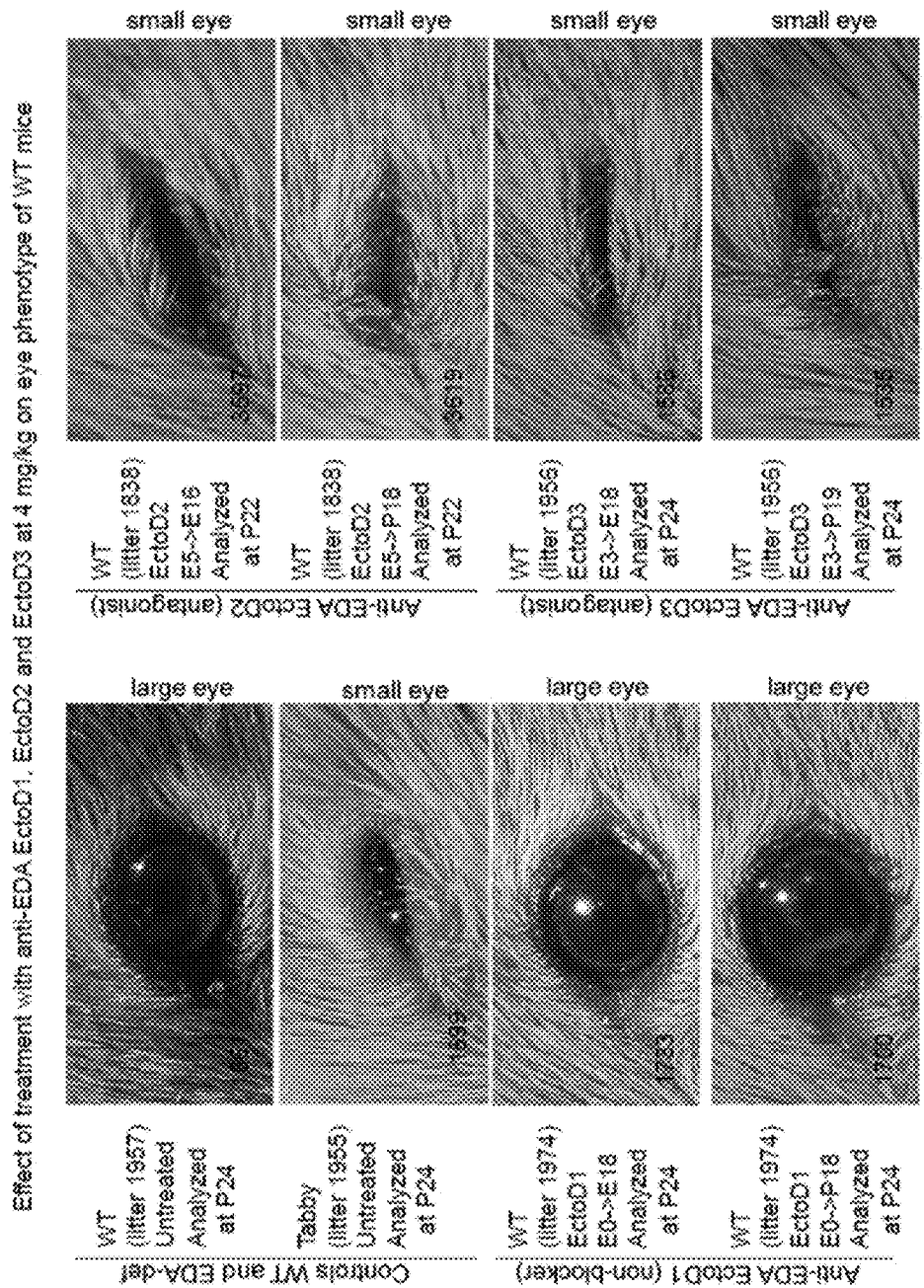
FIG. 13. Photographs of eyes of the same mice shown in FIG. 9. WT mice have wide opened, protruding eyes. Tabby mice have much smaller eye slits.
Figure 14:
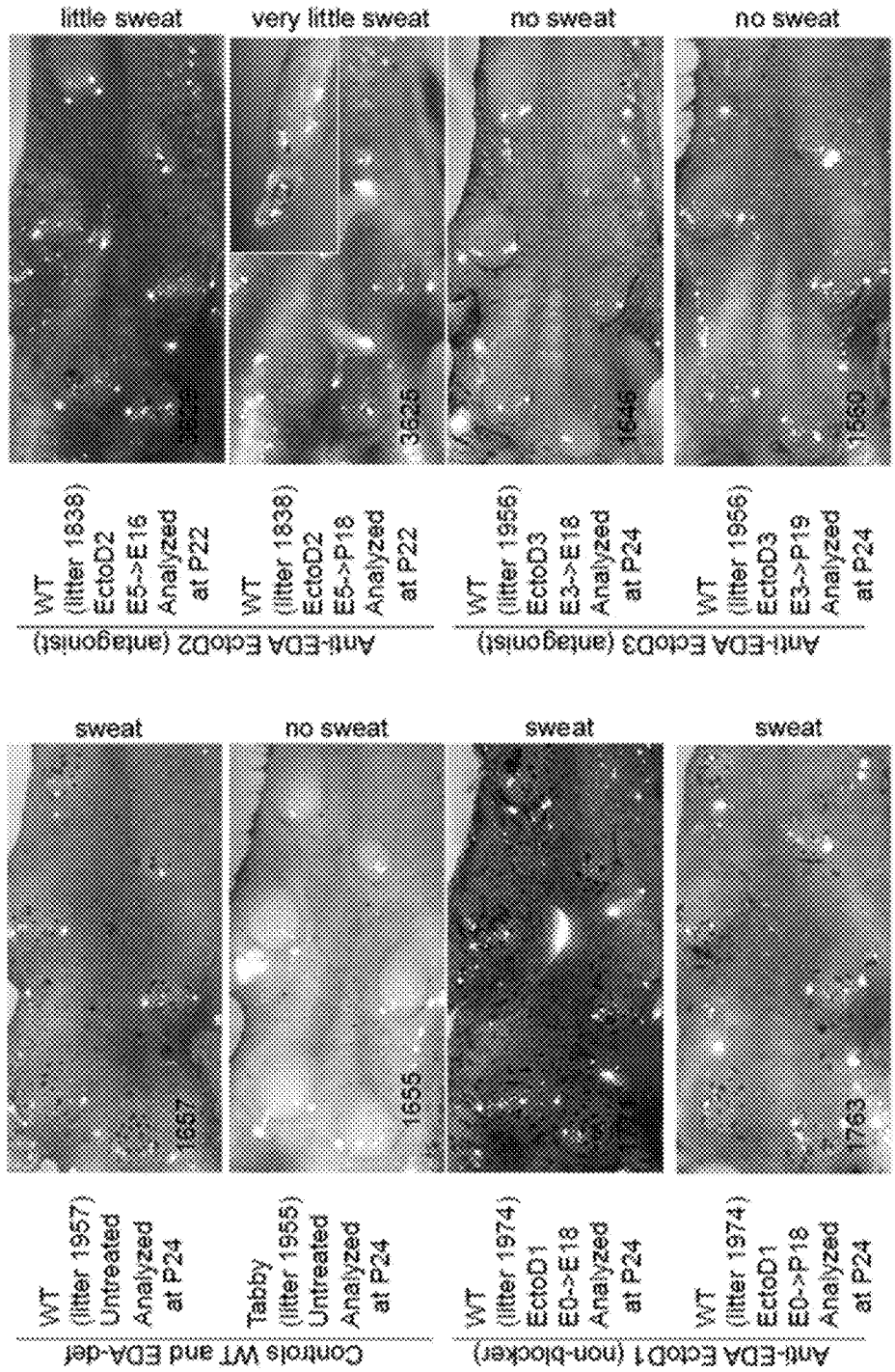
FIG. 14. Photographs of starch-iodine sweat tests performed in palms of the same mice shown in FIG. 9. Functional sweat glands appear as small dark spots. WT mice have numerous sweat glands mainly in footpads. Tabby mice lack sweat glands. The insert in one of the panels shows a single functional sweat gland at a finger tip.
Figure 15:
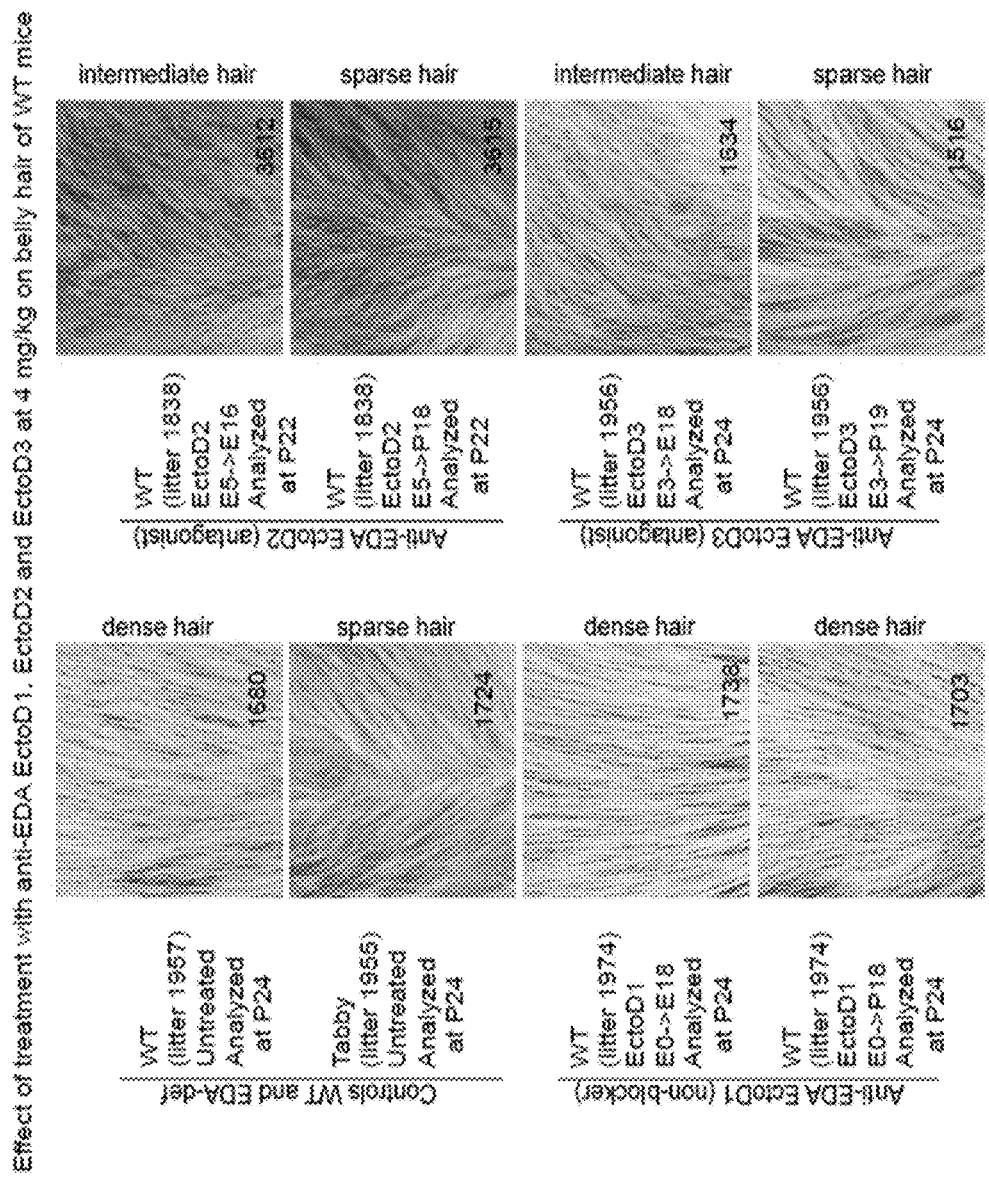
FIG. 15. Photographs of bellies of the same mice shown in FIG. 9. WT mice have a dense, well-organized fur. Tabby mice have sparse, disheveled belly hair.
Figure 16:
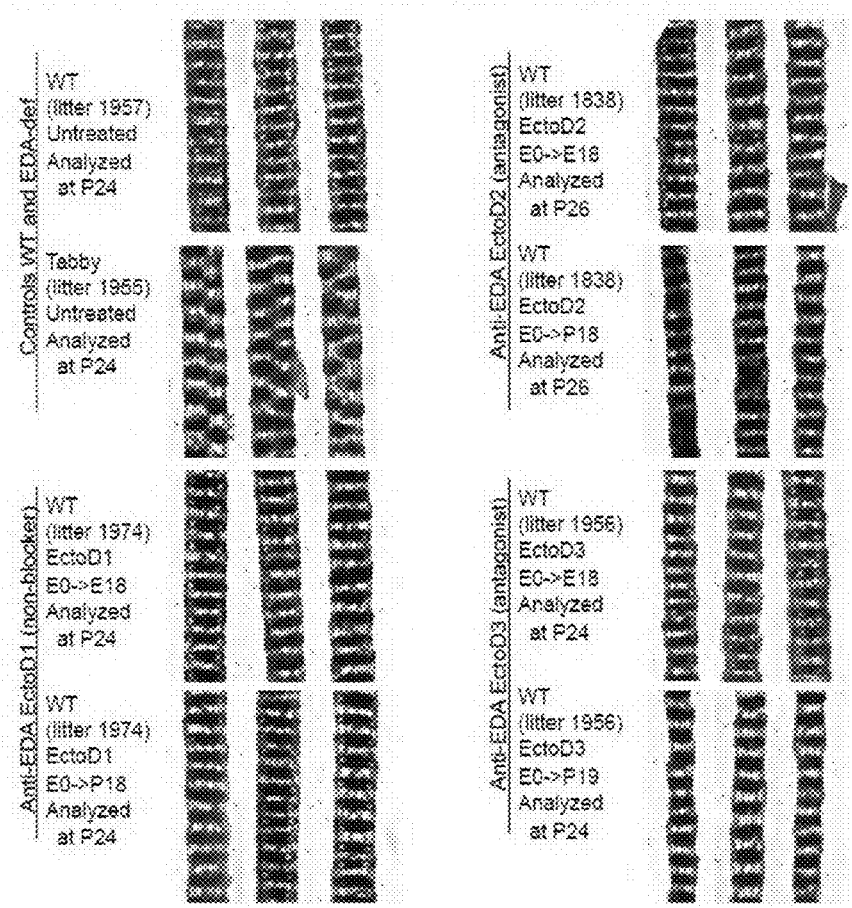
FIG. 16. Photographs of microscope images of pelage (zigzag) hair of the same mice shown in FIG. 9. Hair of WT mice have a single stack of pigmented cell remnants separated by non-pigmented air cells. Tabby mice have two columns of pigmented cells.
Figure 17:
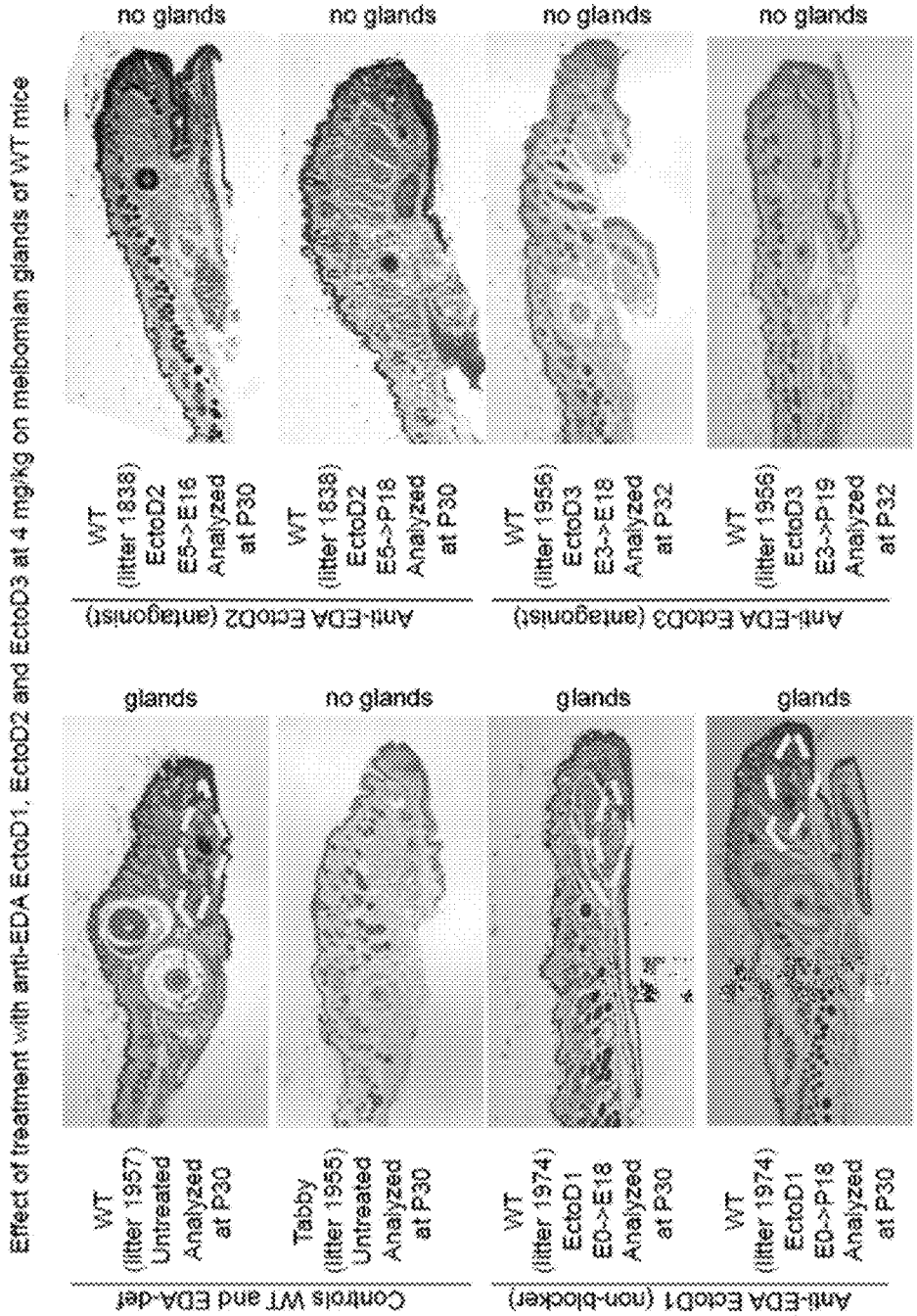
FIG. 17. Photographs of microscope images of H&E-stained eyelid sections of the same mice shown in FIG. 9. Glandular tissue of meibomian glands is apparent in WT mice (highlighted with a dotted line). Tabby mice lack meibomian glands.
Figure 18:
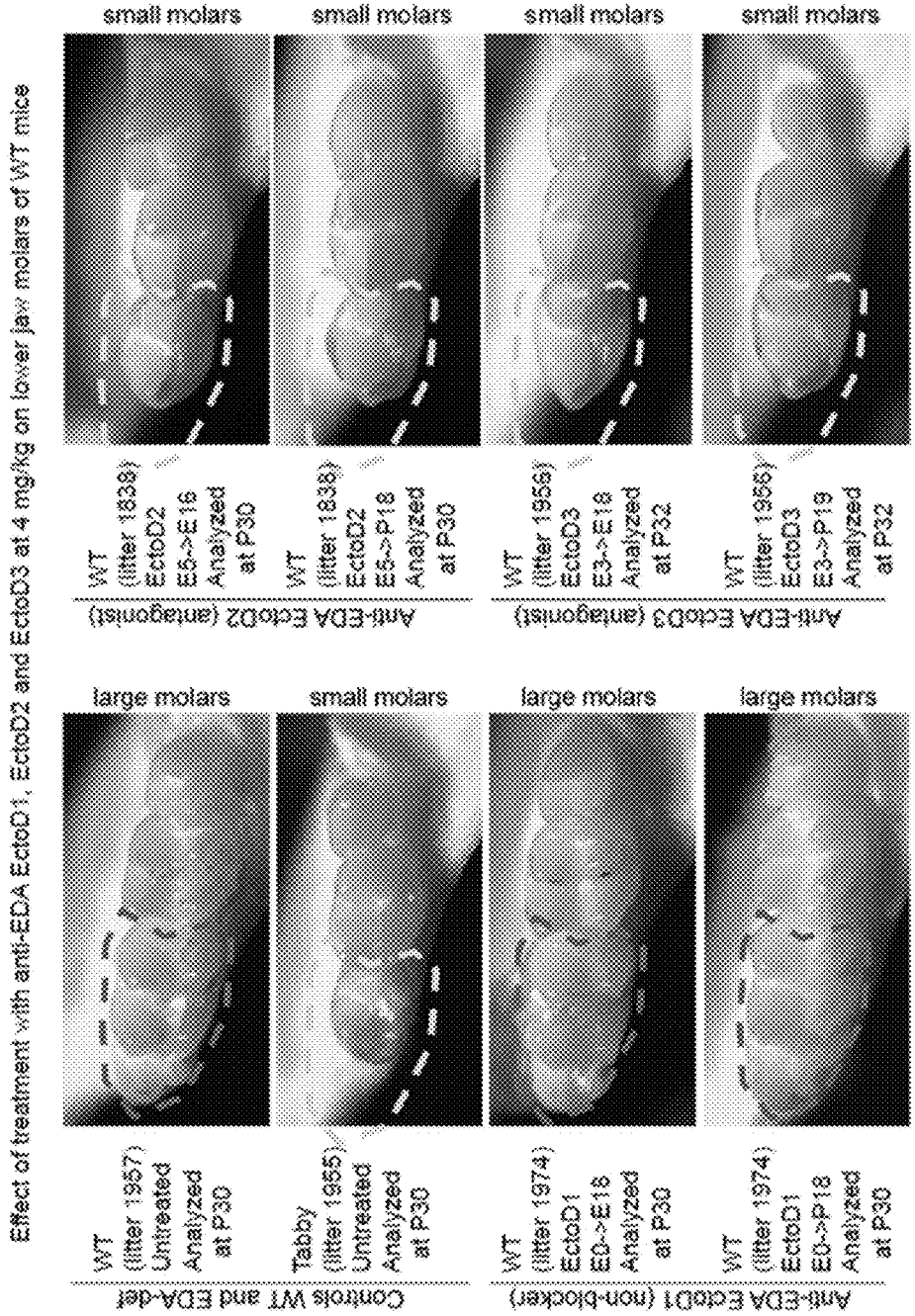
FIG. 18. Photographs of lower molars of the same mice shown in FIG. 9. The first molar of WT mice is big with well-defined cusps. The first molar of Tabby mice is smaller with a less complex shape. The dotted line indicates the approximate size of the first lower molar of WT mice.
Figure 19:
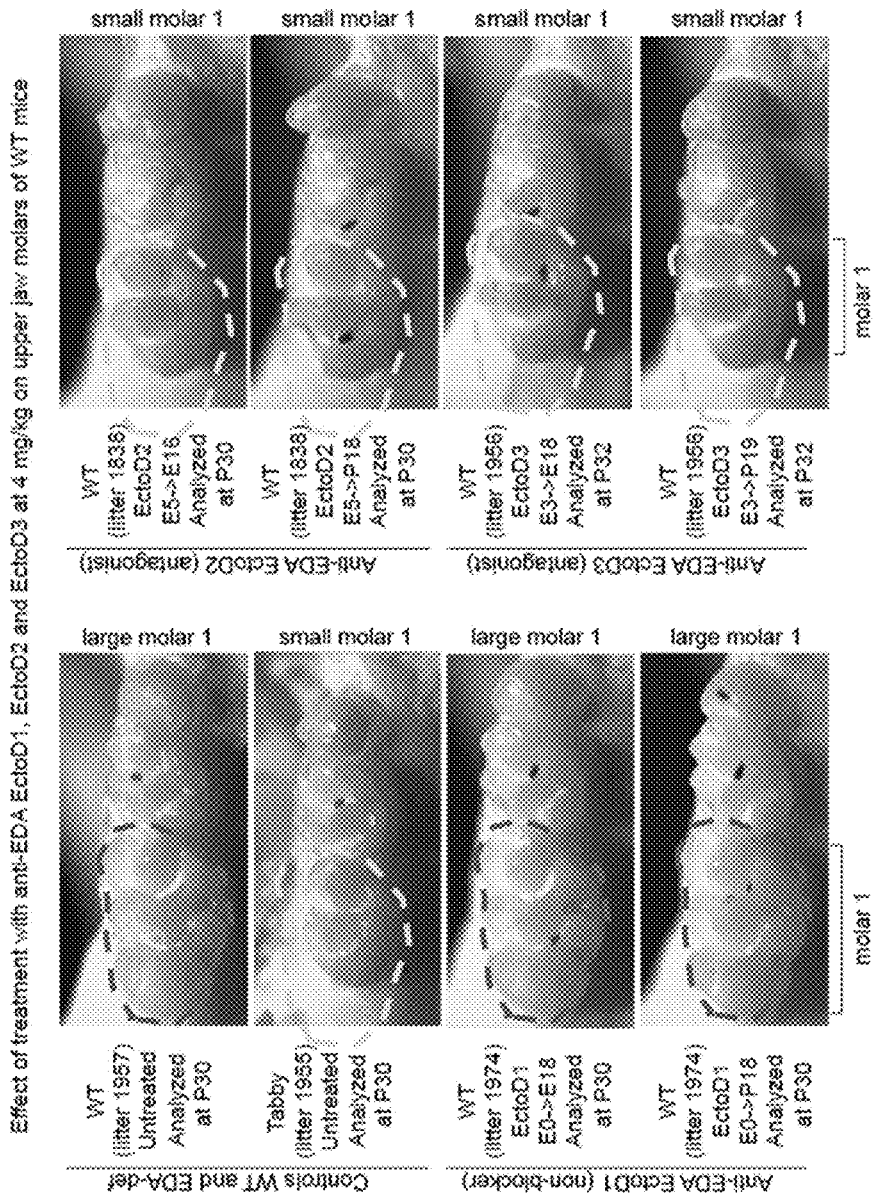
FIG. 19. Photographs of upper molars of the same mice shown in FIG. 9. The first molar of WT mice is big with well-defined cusps. The first molar of Tabby mice is smaller. The dotted line indicates the approximate size of the first upper molar of WT mice.
Figure 20:
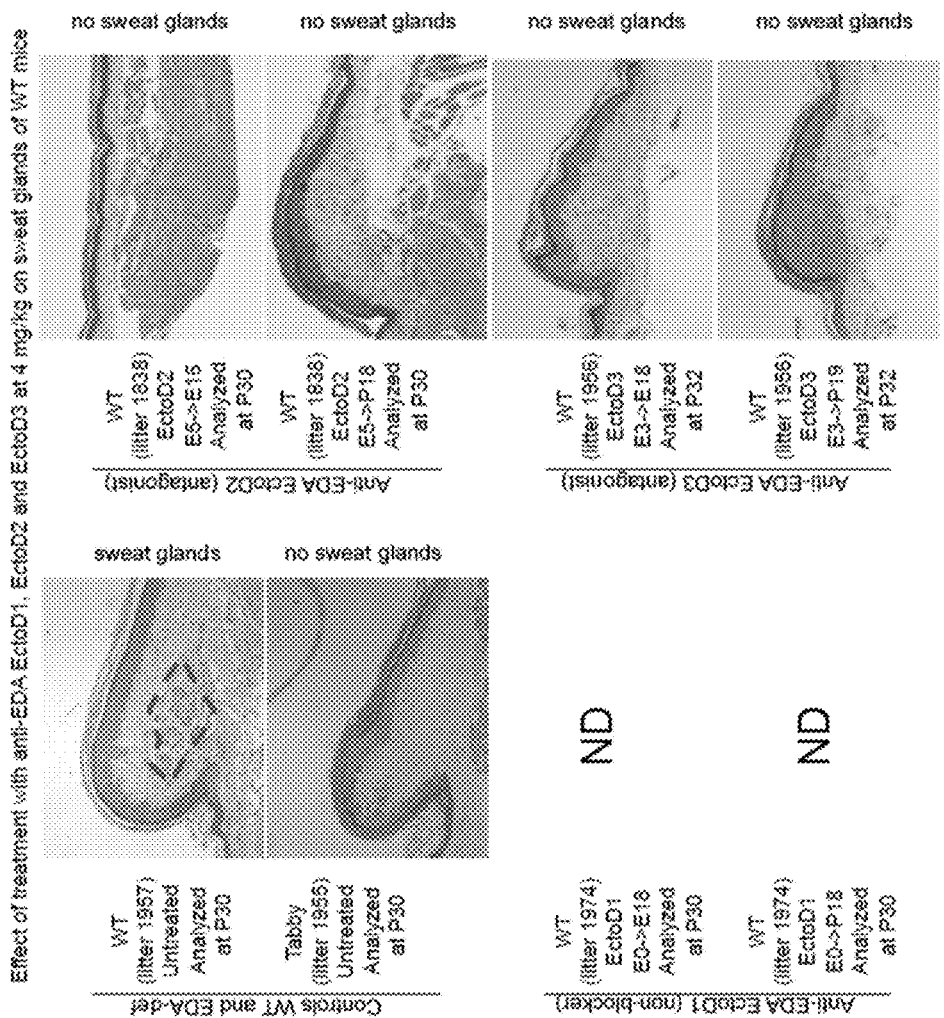
FIG. 20. Photographs of microscope images of H&E-stained footpad sections of the same mice shown in FIG. 9. Glandular tissue of sweat glands is apparent in WT mice (highlighted with a dotted line). Tabby mice lack sweat glands.
Figure 21:
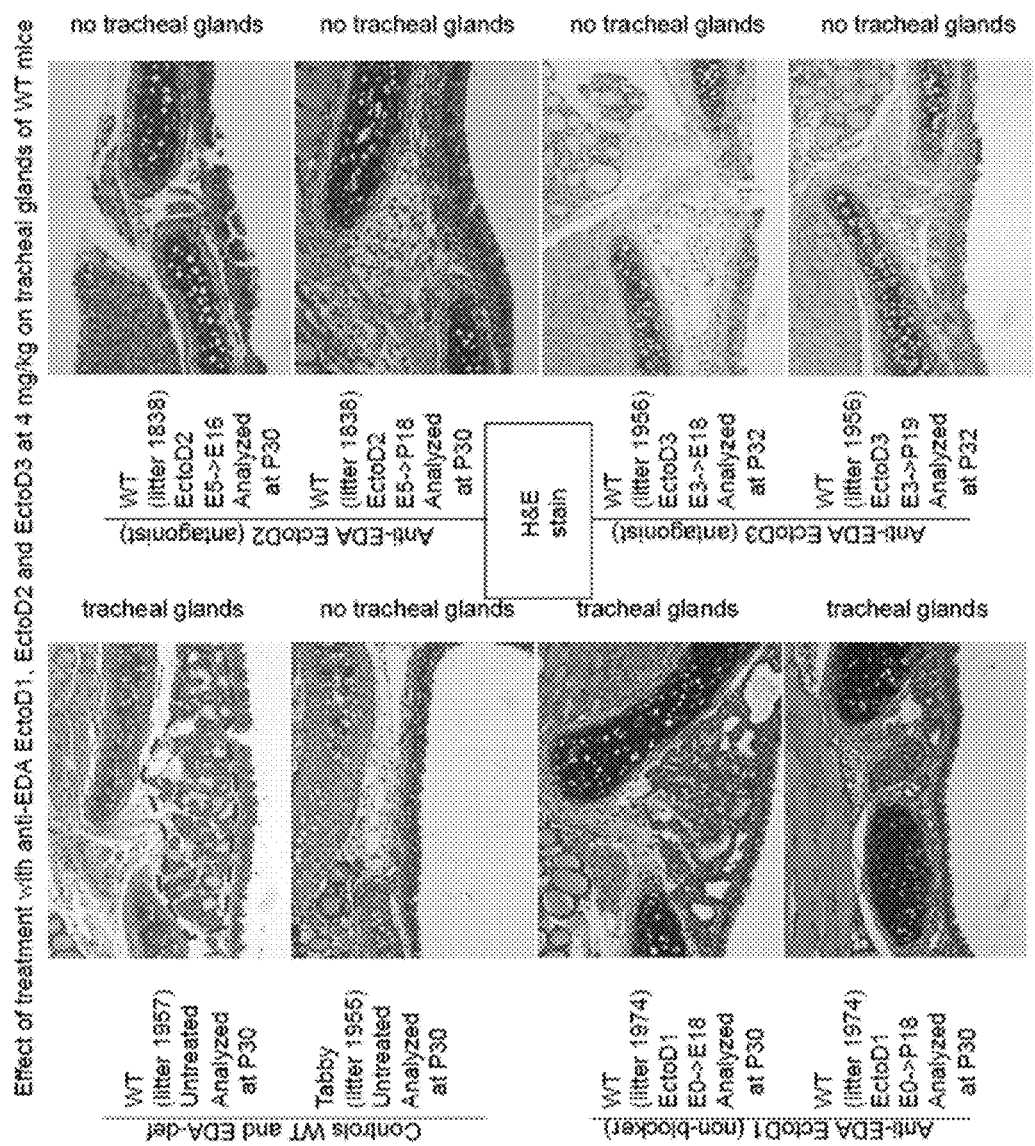
FIG. 21. Photographs of microscope images of sections through the trachea for the same mice shown in FIG. 9. Sections are stained with H&E. Glandular tissue of tracheal glands is apparent in WT mice (highlighted with a dotted line). Tabby mice lack tracheal glands.
Figure 22:
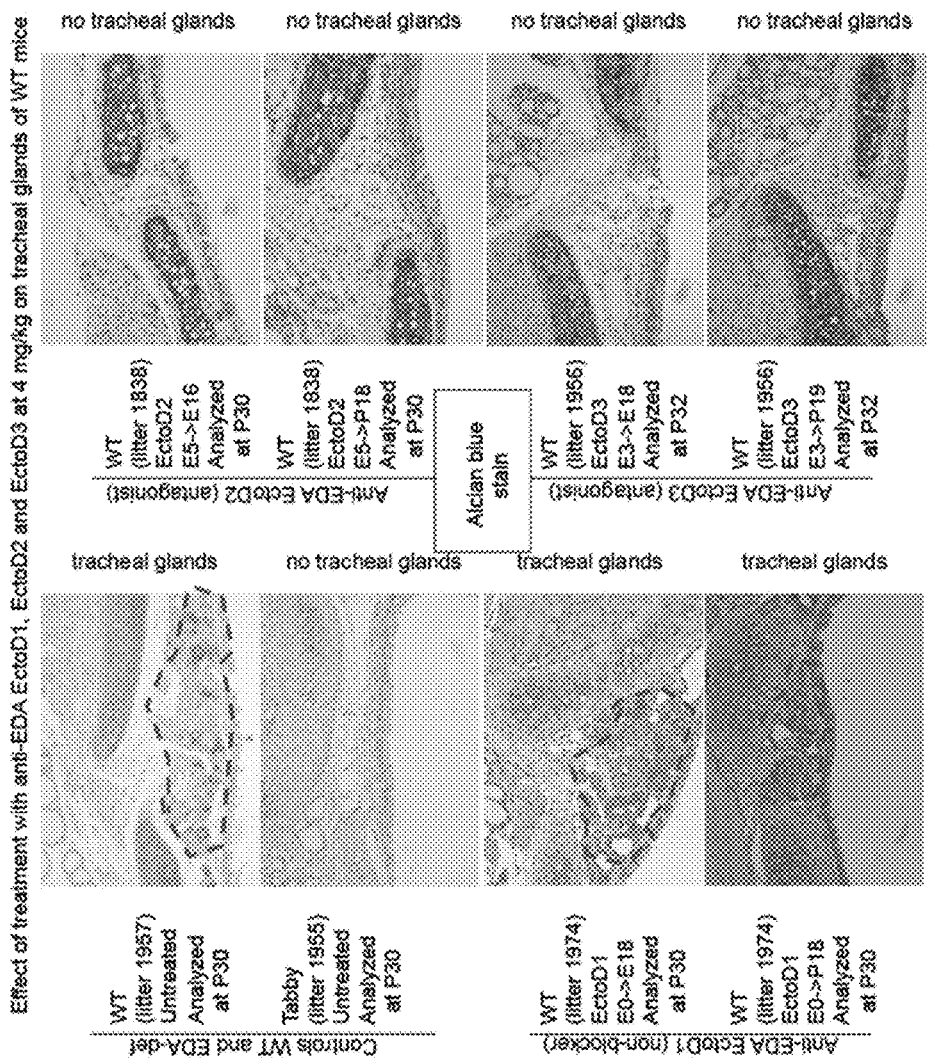
FIG. 22. Same as FIG. 21, except that trachea were stained with Alcian blue to reveal cartilage and mucus. Regions containing tracheal glands are highlighted with dotted lines.

Investigation of the Effects of Administration of mAbEDA1-EctoD1, mAbEDA1-EctoD2 and mAbEDA1-EctoD3 to Wild Type Mice In order to determine the effects of administration of mAbEDA1-EctoD1, mAbEDA1-EctoD2 and mAbEDA1-EctoD3 to wild type mice, a pregnant WT mouse was treated with 100 µg/injection of mAbEDA1-EctoD1 (#1204-24) (~4 mg/kg) at E0, E2, E4, E6, E8, E10, E12, E14, E16, E18. After birth, 2 pups were treated at P1, P2, P4, P6, P8, P10, P12, P14, P16 and P18 with mAbEDA1-EctoD1 at ~4 mg/kg, and 2 pups were not further treated (FIG. 7). Another pregnant WT mouse was treated with 100 µg/injection of mAbEDA1-EctoD2 (#1204-25) (~4 mg/kg) at E5, E9, E12, E16. After birth, 3 pups were treated at P2, P6, P10, P14, P18 with mAbEDA1-EctoD2 at ~3 mg/kg, and 3 pups were not further treated. Another pregnant WT mouse was treated with 100 µg/injection of mAbEDA1-EctoD2 (#A2420-1208) (~4 mg/kg) at E3, E5, E8, E10, E12, E14, E16, E18. After birth, 4 pups were treated at P1, P3, P5, P7, P9, P11, P13, P15, P17 and P19 with mAbEDA1-EctoD3 at ~4 mg/kg, and 5 pups were not further treated (FIG. 7). External appearance and functional sweat tests were assessed/performed at P22 or P24. Mice were sacrificed at P30 or P32 for collection of eyelids, footpads, trachea and skulls. Hair was collected at P22 or P26. FIG. 8 is a photograph showing comparisons of Tabby mice, wild-type mice treated with mAbEDA1-EctoD2 or mAbEDA1-EctoD3 and untreated wild-type mice. The photographs indicate that the mice treated with mAbEDA1-EctoD2 or mAbEDA1-EctoD3 resemble Tabby mice. FIG. 9 shows a series of photographs of guard hair. FIG. 10 shows a series of photographs of tails. FIG. 11 shows a series of photographs of the tip of tails. FIG. 12 shows a series of photographs of ears. FIG. 13 shows a series of photographs of eyes. FIG. 14 shows a series of photographs of footpads after a starch-iodine sweat test where functional sweat glands are revealed as small black dots. FIG. 15 shows a series of photographs of bellies. FIG. 16 shows a series of photographs displaying the central portion of the most abundant type of dorsal hair (zig-zag hair). FIG. 17 shows a series of microscope images of eyelid sections, where meibomian glands, when present, are highlighted by a dotted line. FIG. 18 shows a series of photographs of lower jaw molars. FIG. 19 shows a series of photographs of upper jaw molars. FIG. 20 shows a series of microscope images of footpad sections where sweat glands, when present, are highlighted by a dotted line. FIG. 21 shows a series of microscope images of trachea sections stained with hematoxylin and eosin where mucus-secreting tracheal glands, when present, are highlighted by a dotted line. FIG. 22 shows sections adjacent to those of FIG. 21 stained with Alcian blue that stains cartilage and mucus blue. The conclusions reached by analysis of these photographs are that with administration of mAbEDA1-EctoD2 or mAbEDA1-EctoD3, tail hair is not or only mildly affected, a kink at the tip of the tail becomes visible, retroauricular and guard hair does not develop, teeth take on abnormal shape and size, sweat glands fail to develop in the pups treated continuously with mAbEDA1-EctoD2 or mAbDA1-EctoD3, or in mice treated in utero with mAbEDA1-EctoD3, but some develop in pups treated in utero but not postnatally with mAbEDA1-EctoD2, tracheal glands do not develop, Mebomian glands do not develop, eyes are small and like in Tabby mice and far less protuberant than in WT mice, and that morphology of zigzag hair is affected, especially upon prolonged treatment, but without reaching the morphology of Tabby hair. In contrast, none of Tabby-specific phenotypes develops in WT mice treated with mAbEDA1-EctoD1.

These observations provide evidence that the wild-type mice treated with mAbEDA1-EctoD2 or mAbEDA1-EctoD3 take on characteristics of Tabby mice. Therefore, administration of mAbEDA1-EctoD2 or mAbEDA1-EctoD3 blocks the action of endogenous EDA1 in binding to its receptor EDAR and inducing normal development. This provides an indication of specific binding of mAbEDA1-EctoD2 and mAbEDA1-EctoD3 to EDA1 in vivo and further indicates that mAbEDA1-EctoD2 and mAbEDA1-EctoD3 will be useful for detection and quantitative analysis of EDA1 or recombinant EDA1 (such as Fc-EDA1) in immunoassays such as ELISAs. These results also indicate that treatment with mAbEDA1-EctoD2 may be useful for treating disorders arising from excessive action of EDA1 such as sebaceous gland hyperplasia, hyperhidrosis, hirsutism, or certain types of cancers such as breast cancer and dermal eccrine cylindroma.

Example 6

Usage of mAbEDA1-EctoD2 and mAbEDA1-EctoD3 for the Specific Detection of Naturally Cleaved EDA1 or Recombinant Fc-EDA1

Figure 23:
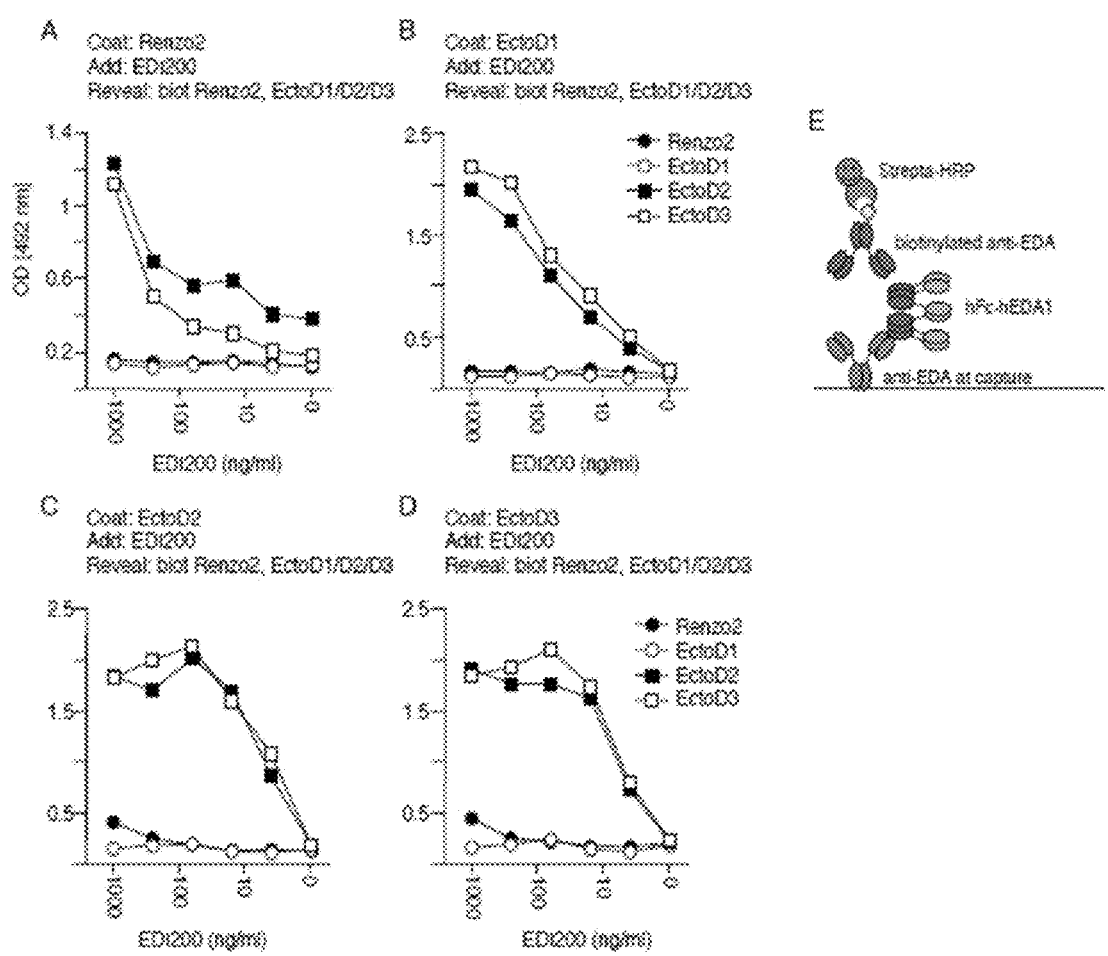
FIG. 23. Results of a series of sandwich ELISAs using four mAbEDA1 antibodies (Renzo2, EctoD1, EctoD2, EctoD3) in all possible combinations. A signal indicate the successful capture of Fc-EDA1 by the coated antibody and its efficient revelation by the revelation antibody.
Figure 24:
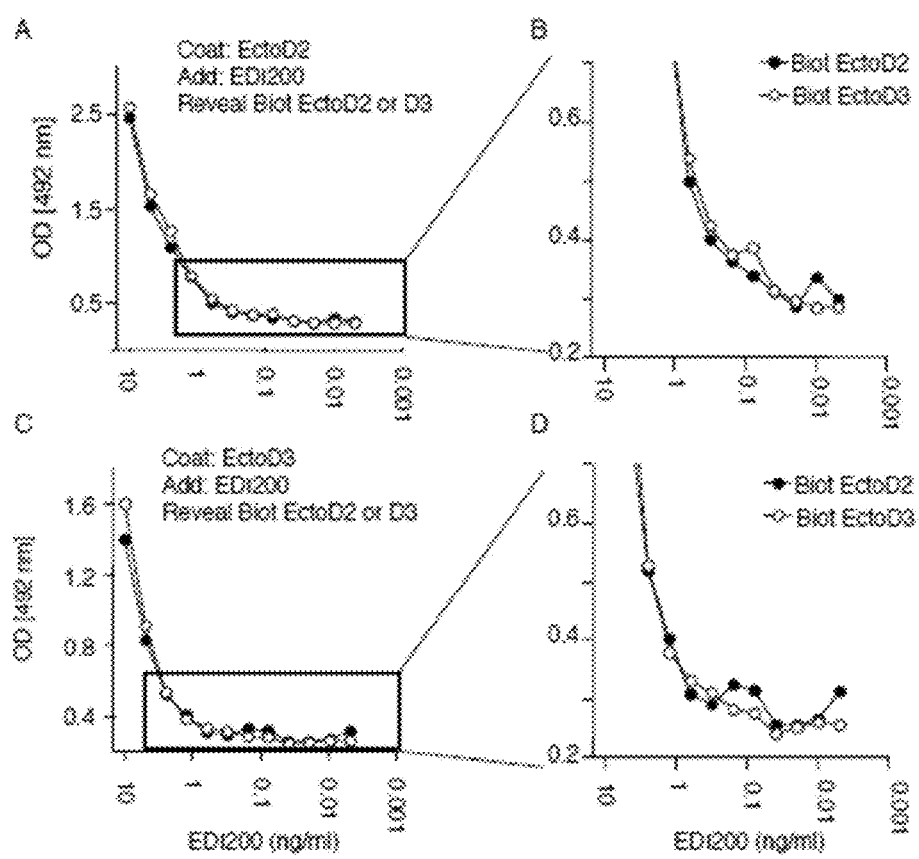
FIG. 24. Results of a sandwich ELISA using either mAbEDA1-EctoD2 or mAbEDA1-EctoD3 at capture and the same biotinylated antibodies at revelation. Graphs on the right are enlargements of a portion of the graphs on the left.

In order to evaluate whether anti-EDA1 could be used for the specific detection of EDA1, four different anti-EDA1 antibodies (mAbEDA1-Renzo2, mAbEDA1-EctoD1, mAbEDA1-EctoD2 and mAbEDA1-EctoD3) were prepared in biotinylated and non-biotinylated forms and tested in all possible combinations in a sandwich ELISA. mAbEDA1-EctoD2 and mAbEDA1-EctoD3 proved superior to mAbEDA1-EctoD1 and mAbEDA1-Renzo2 at both capture and revelation of recombinant Fc-EDA1 (FIG. 23). A repetition of the experiment using lower concentrations of recombinant Fc-EDA1 revealed that mAbEDA1-EctoD2 used at capture yielded more sensitive signals than mAbEDA1-EctoD3, but that both antibodies gave comparable performance at revelation (FIG. 24). With the combination of EctoD2 and biotinylated EctoD3, less than a ng/ml of Fc-EDA1 was readily detected.

Figure 25:
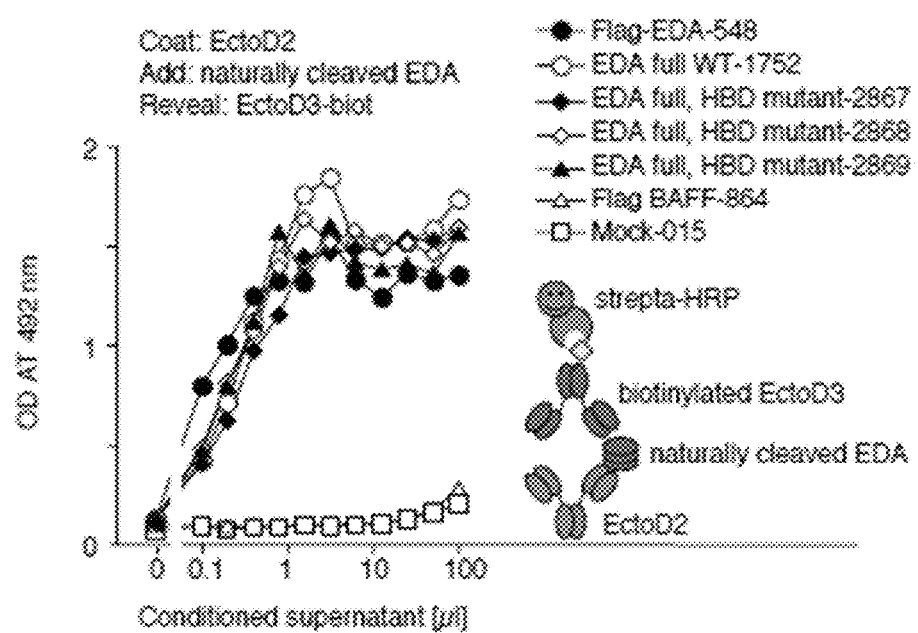
FIG. 25. Results of a sandwich ELISA using mAbEDA1-EctoD2 at capture and biotinylated mAbEDA1-EctoD3 at revelation, showing that this pair of antibodies specifically recognized Flag-tagged-EDA1 and naturally processed untagged EDA1, but not an irrelevant control.
Figure 26:
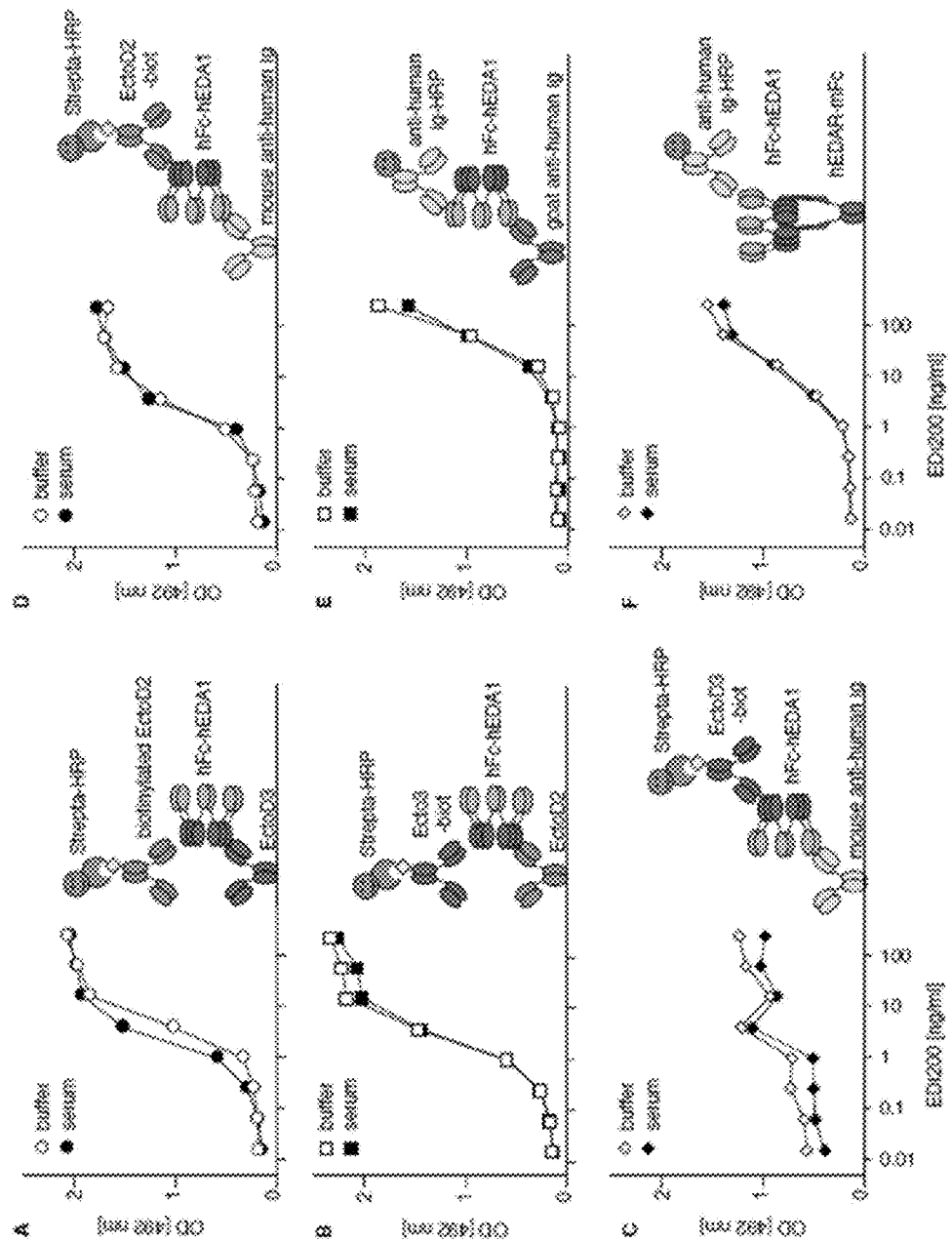
FIG. 26. Results of a several sandwich ELISAs to detect recombinant Fc-EDA1 in buffer (opened symbols) or in mouse serum (closed symbols). The sandwich ELISAs use mAbEDA1-EctoD2, mAbEDA1-EctoD3, mouse anti-human Ig antibodies, goat anti-human Ig antibodies, or recombinant EDAR-Fc in various combinations, as indicated.
Figure 29:
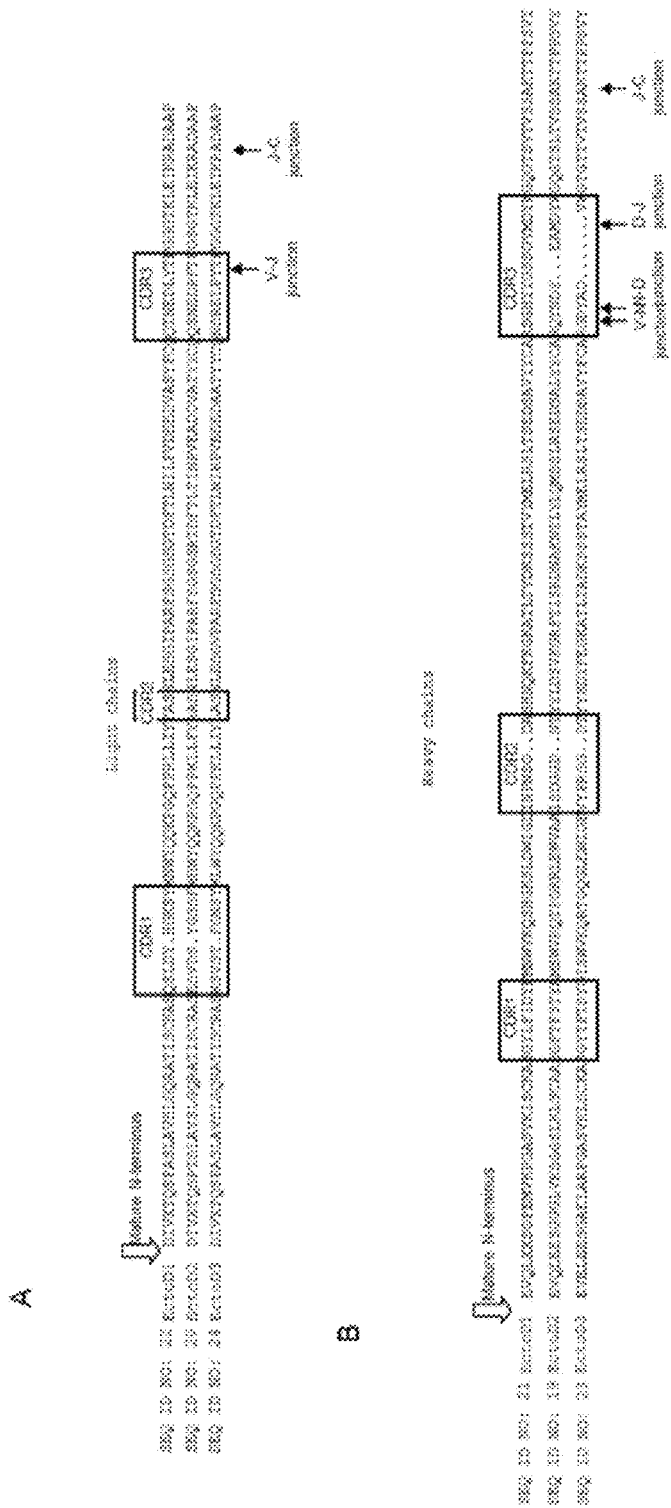
FIG. 29. Amino acid sequences of the light and heavy chains of mAbEDA1-EctoD1, mAbEDA1-EctoD2, and mAbEDA1-EctoD3 showing the three CDRs for each chain as well as a V-J junction, J-C junctions, a V-N junction, an N-D junction and a D-J junction.

FIG. 25 shows that mAbEDA1-EctoD2 and biotinylated mAbEDA1-EctoD3 can also recognize untagged, naturally cleaved EDA1 harvested in conditioned supernatants of 293T HEK cells transfected with full-length EDA1. The recognition was similar for WT EDA1 and for EDA1 harbouring various mutations in the proteoglycan-binding portion of EDA1. The irrelevant Flag-tagged TNF family member BAFF was not recognized in this assay (FIG. 25). The detection of recombinant Fc-EDA1 pre-incubated in buffer or in mouse serum was tested in various sandwich ELISA formats revealing either the EDA1 portion of Fc-EDA1, or the Fc portion of Fc-EDA1, or both (see schematic diagrams of FIG. 26). The most sensitive detection (less than 1 ng/ml) was achieved with mAbEDA1-EctoD2 at capture and biotinylated mAbEDA1-EctoD3 at revelation.

It is noteworthy that detection was as efficient in the presence of serum than in buffer (FIG. 26B). Efficient detection of Fc-EDA1 was also achieved with a mouse anti-human Ig a capture, but this detection system is predicted not to work in serum due to the presence of high concentrations of human Ig (FIG. 26D).

In conclusion, anti-EDA1 antibodies disclosed in this invention allow sensitive detection of recombinant Fc-EDA1, also in the presence of serum. Such immunoassays are expected to provide useful tools for characterizing pharmacokinetic and pharmacodynamic profiles of patients being treated with recombinant EDA1 and improving dosing regimens for such treatments. They may also be suitable to detect endogenous EDA1 in biological fluids, which may be used as diagnostic tools for the detection of conditions with EDA1-deficiency (such as hypohidrotic ectodermal dysplasia) or with an excess of EDA1 (such as hirsutism, hyperhidrosis, sebaceous gland hyperplasia, breast cancer, dermal eccrine cylindroma, and skin conditions arising from overactive sebaceous glands, such as sebaceous gland hyperplasia, comedones, milia, acne, seborrhea, rosacea, steatoma, or furuncles).

Example 7

Usage of mAbEDA1-EctoD2 and mAbEDA1-EctoD3 for Blockage of EDA1 and EDA2

In order to evaluate whether anti-EDA antibodies could inhibit EDA ligand binding to cognate receptors, a cell based in vitro flow cytometry assay was performed. The 293T cell line was co-transfected with plasmids expressing EGFP and modified human or chicken EDAR and XEDAR receptors containing a glycoloipid anchor addition signal domain. Recombinant human or chicken Fc-EDA1 and Fc-EDA2 ligands were added to the cell culture either alone or following pre-incubation with anti-EDA1 antibodies. The cells were then stained and analyzed by flow cytometry for ligand-receptor binding.

Figure 33:
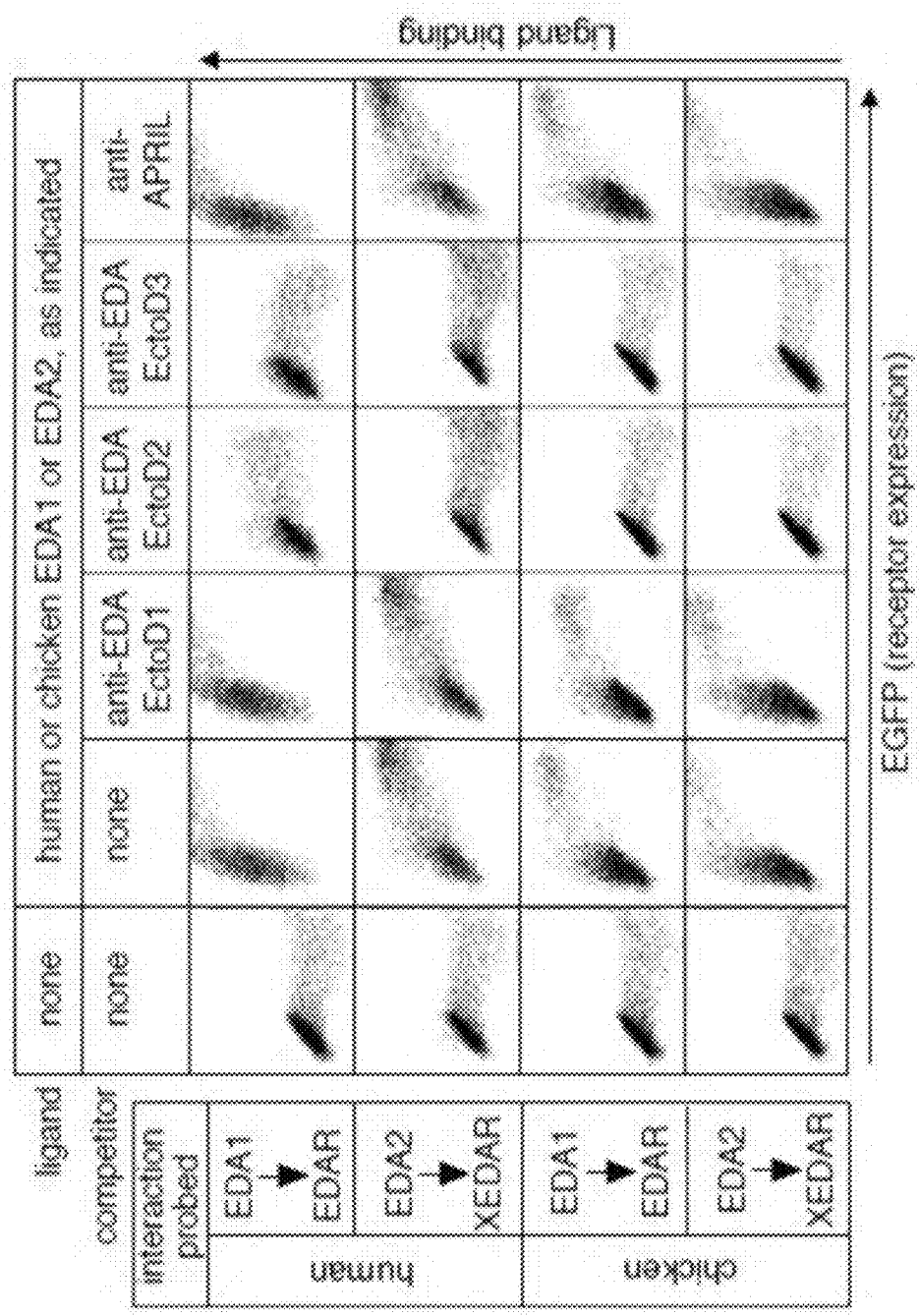
FIG. 33. Receptors (human or chicken EDAR or XEDAR) fused to the GPI anchor of TRAILR3 were expressed in 293T cells together with an EGFP tracer (x-axis). Cells were stained with or without cell supernatants containing Fc-EDA1 or Fc-EDA2 of human/mouse (human) or chicken origin (y-axis). The interactions of Fc-EDAs with GPI-anchored receptors were challenged by preincubation of the ligand with anti-EDA antibodies (EctoD1, EctoD2, EctoD3) or with an irrelevant antibody (anti-APRIL). Both scattergram axes show fluorescence intensity on a logarithmic scale ($10^0$-$10^4$).

As noted previously, human EDA1 and EDA2 differ in sequence only by a lack of two amino acids in EDA2. Across species human EDA1 is 100% and 98% identical to mouse and chicken EDA respectively. FIG. 33 shows that both mAbEDA1-EctoD2 and mAbEDA1-EctoD3 block the interactions of EDA1 and EDA2 with cognate receptors EDAR and XEDAR in both human and chicken. mAbEDA1-EctoD2 and mAbEDA1-EctoD3 are concluded to recognize common epitopes shared by the splice isoform EDA1 and EDA2 ligands.

In conclusion, anti-EDA1 antibodies disclosed in this invention allow for the broad spectrum inhibition of EDA signaling in post-developmental functions where EDA1 and EDA2 ligands may have overlapping pathological activities from excess signaling. Additionally, FIG. 33 demonstrates the ability of EDA2 to bind chicken XEDAR and the ability of mAbEDA1-EctoD2 and mAbEDA1-EctoD3 to block this interaction.

Example 8

Figure 34:
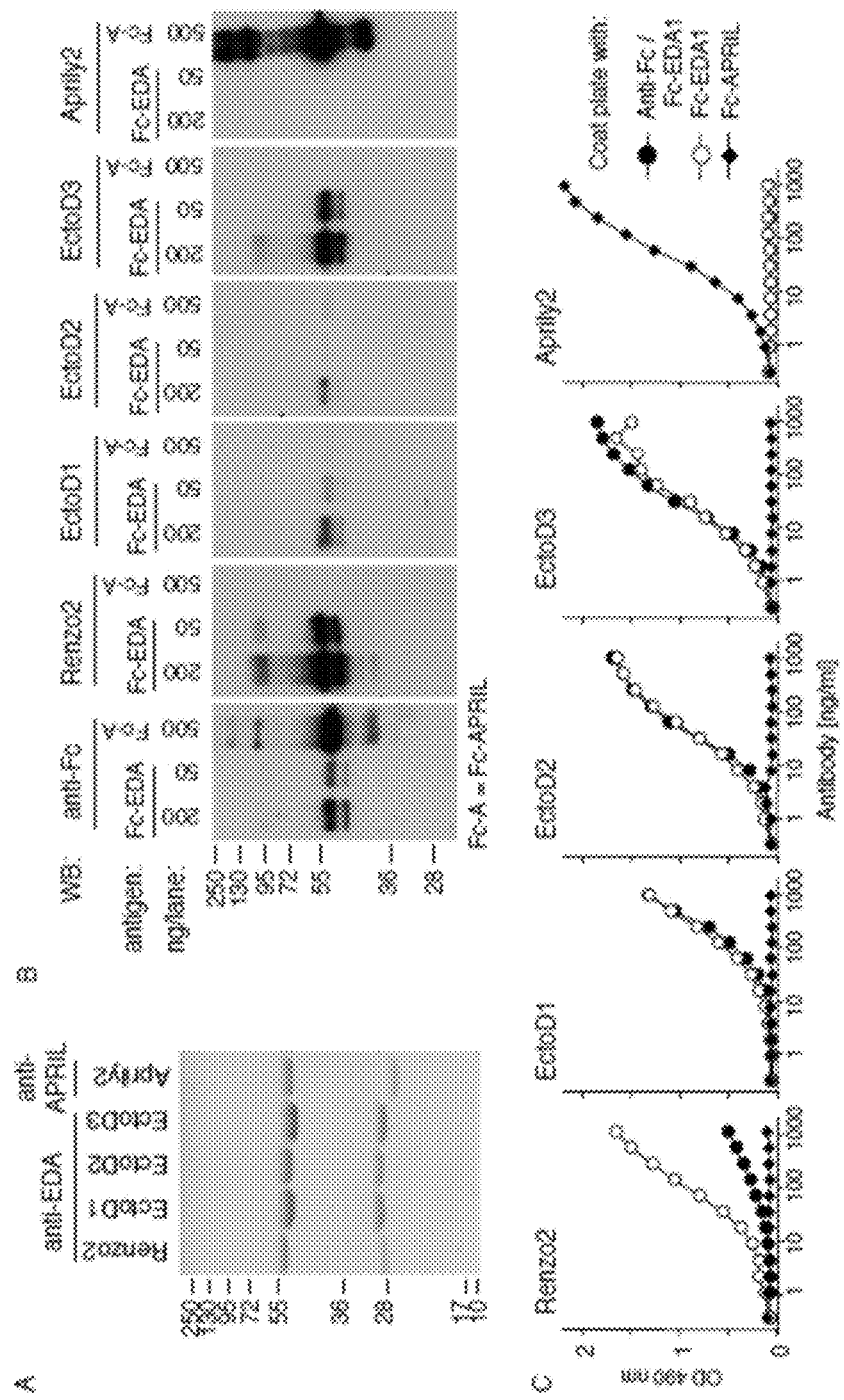
FIG. 34. SDS-PAGE analysis and Coomassie blue staining of 10 µg per lane of the indicated purified mouse IgG1 monoclonal antibodies under reducing conditions (Panel A). Western blotting under reducing conditions using anti-human immunoglobulin (anti-Fc), anti-EDA (Renzo2, EctoD1, EctoD2, EctoD3) or anti-APRIL (Aprily2) antibodies (Panel B). ELISA using Fc-EDA1 and Fc-APRIL proteins, or Anti-Fc/EDA1 antibody coated directly in an ELISA plate (Panel C).

Specific Blockage of EDA1 Activity by mAbEDA1-EctoD2 and mAbEDA1-EctoD3 Recognition of Native Receptor Binding Site Epitopes Anti-EDA antibodies recognize epitopes on native EDA1. Purified antibodies (FIG. 34A) were tested for their recognition of denatured and native EDA1. EctoD1 and EctoD2 almost failed to recognize reduced Fc-EDA by western blot, whereas EctoD3 produced a more convincing signal on Fc-EDA1, but not on an excess of the control protein Fc-APRIL. (FIG. 34B). An ELISA assay was performed in which the antigen Fc-EDA1 was either coated directly to the plate, a process that partially denatures proteins, or captured via its Fc portion to keep it native. EctoD1, EctoD2 and EctoD3 recognized both coated and captured Fc-EDA1 with similar intensities, suggesting that they recognize surface-exposed epitopes in EDA1 (FIG. 34C).

Figure 35:
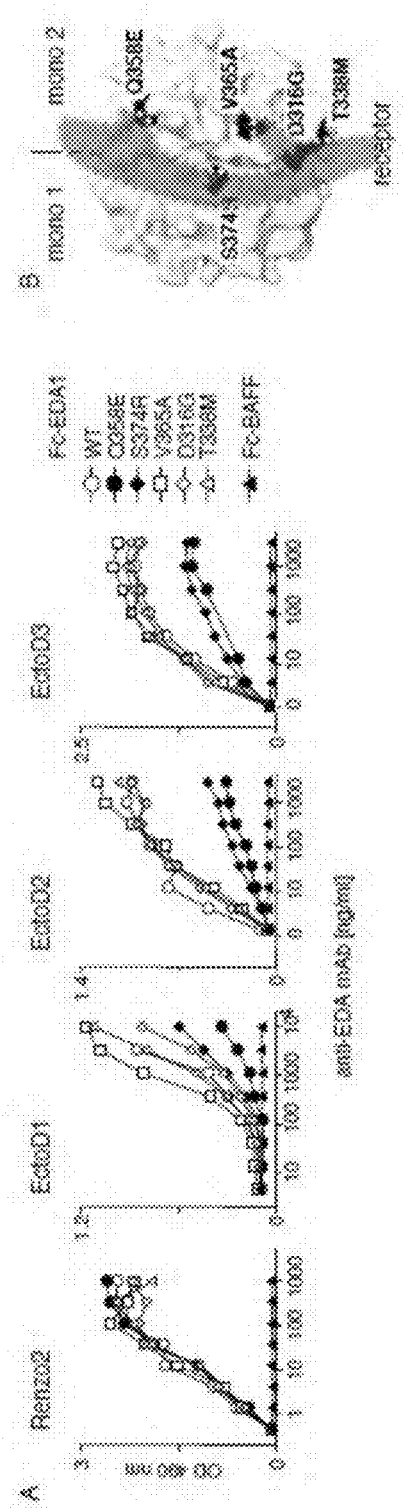
FIG. 35. Fc-EDA1 WT or containing the indicated point mutations, or Fc-BAFF as a control, were coated onto ELISA plates, and revealed with the indicated antibodies at the indicated concentration (Panel A). Space filling representation of EDA1 receptor binding site (Panel B).
Figure 36:
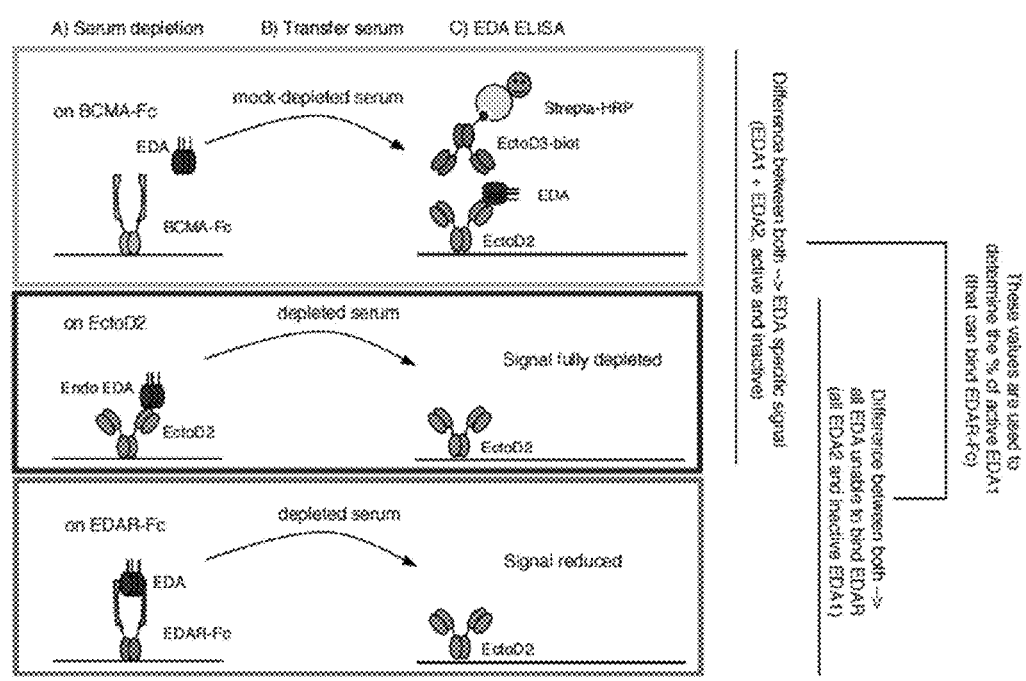
FIG. 36 is a schematic representation of the pre-depletion step described in Example 9, using plates coated with BCMA-Fc (mock-depletion), EDAR-Fc and EctoD2.
Figure 37:
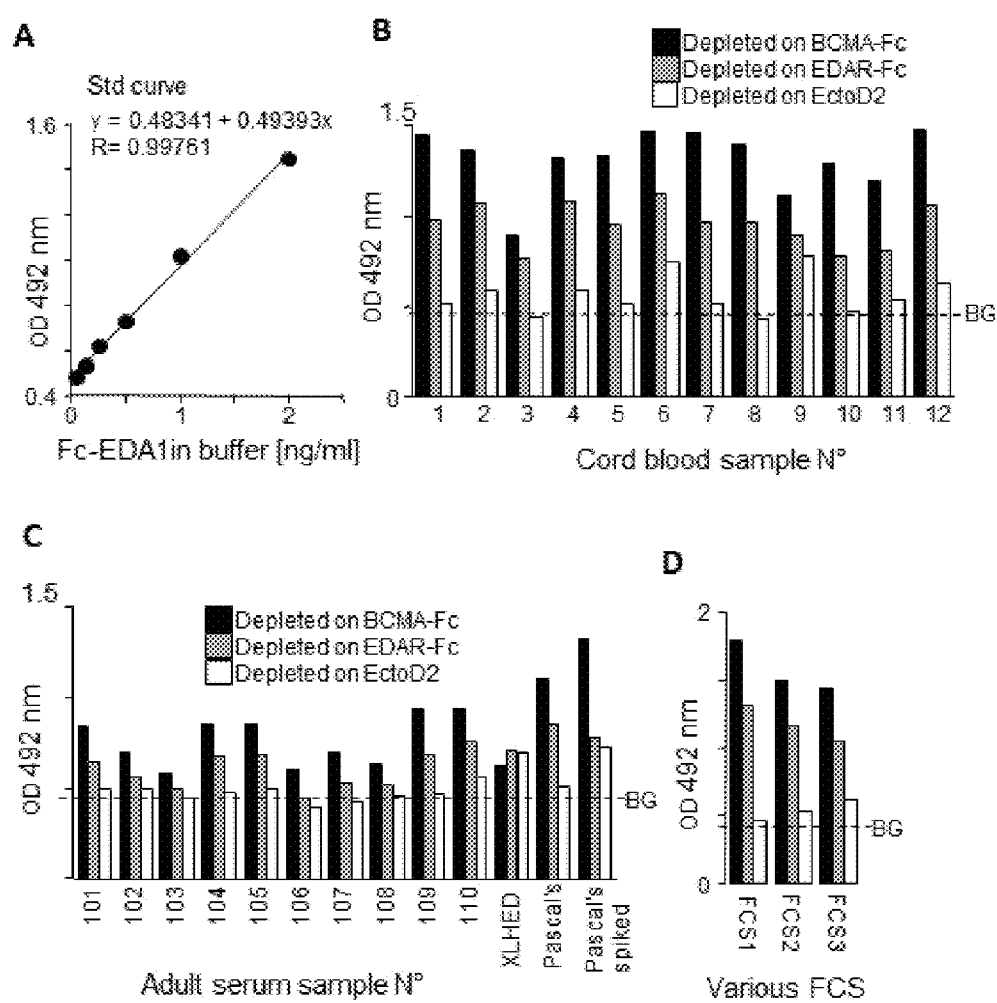
FIG. 37A is a standard curve of Fc-EDA1 (ng/mL) in buffer (see Example 9).
FIG. 37B is a bar chart showing the absorbance (at 492 nm) of samples of cord blood serum depleted on BCMA-Fc, EDAR-Fc and Ecto-D2, as obtained with the EDA ELISA (see Example 9).
FIG. 37C is a bar chart showing the absorbance (at 492 nm) of samples of adult serum depleted on BCMA-Fc, EDAR-Fc and EctoD2 (see Example 9).
FIG. 37D is a bar chart showing the absorbance of three samples of fetal calf serum depleted on BCMA-Fc, EDAR-Fc and EctoD2 (see Example 9).
Figure 38:
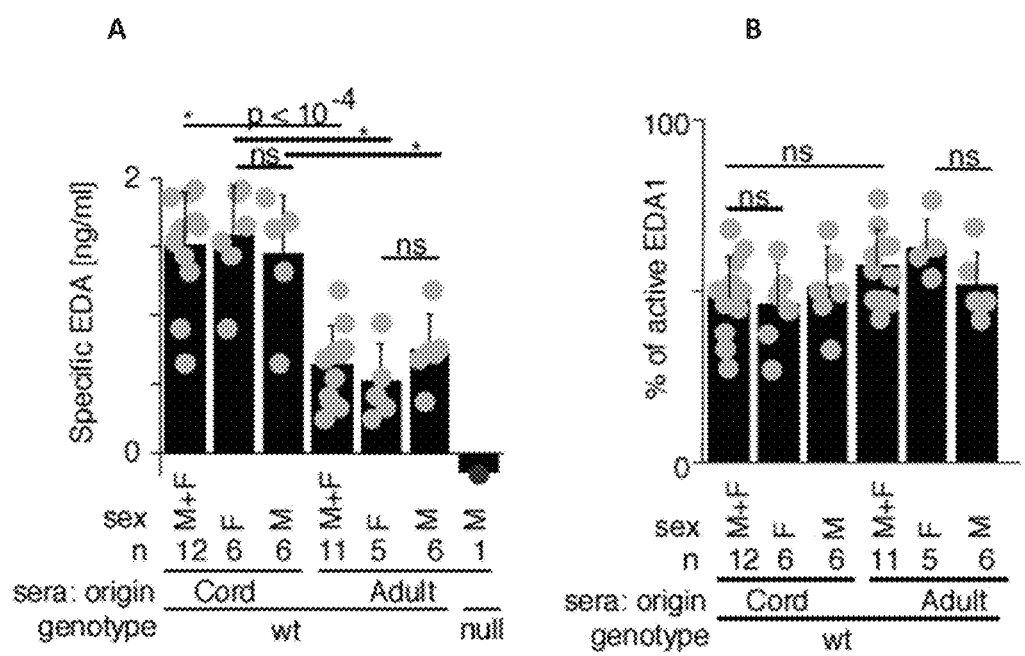
FIG. 38A is a bar chart showing the results of the statistical analysis between sample groups with respect to specific EDA (ng/mL), based on the data shown in FIG. 37. p values are less than $10^{-4}$ for the comparison between cord blood serum and adult serum. The comparisons among the other groups in this chart indicate a lack of statistical significance (ns=not significant; see Example 9).
FIG. 38B is a bar chart showing the results of the statistical analysis between sample groups with respect to the percentage of active EDA1, based on the data shown in FIG. 37. The comparisons among the groups in this chart indicate a lack of statistical significance (ns=not significant; see Example 9).

The recognition of Fc-EDA1 by anti-EDA antibodies was tested on a panel of EDA1 mutations. EctoD2 and EctoD3 detected mutants Q358E or S374R with reduced intensity, suggesting that these two amino acid residues are part of the epitope (FIG. 35A). EctoD1 displayed the same general behavior as EctoD2 and EctoD3 (FIG. 35A). In the crystal structure of EDA1 (Hymowitz, S. G., et al. (2003) *Structure (Camb)* 11, 1513-1520), S374 and Q358 are located in the membrane-proximal portion of the TNF homology domain, lining the predicted receptor-binding site on two adjacent EDA1 monomers (FIG. 35B). The recognition site of EDA1 by EctoD2 and EctoD3 is therefore predicted to overlap with the receptor binding site, thereby interfering with receptor binding.

In conclusion, anti-EDA antibodies EctoD2 and EctoD3 block EDA1 activity by recognition of epitopes overlapping the receptor-binding site in the native EDA1 protein found in vivo.

Example 9

Specificity of a Sandwich-Type ELISA Using EctoD2 as the Capture Agent and EctoD3-Biotin as the Detection Agent This experiment was performed in order to validate the specificity of a sandwich-type ELISA based upon the use of EctoD2 as the capture agent and EctoD3-biotin as the detection agent, for the purpose of obtaining a quantitative analysis of EDA and EDA1 levels in human serum. This particular experiment includes a pre-depletion step for discriminating EDA-specific signals from non-specific signals. If the ELISA is performed without pre-depletion, a determination of the specificity of the signal would not be possible. To distinguish specific from non-specific signals, the serum is first depleted on various EDA-binding agents: EDAR-Fc and EctoD2, or non-binding for control agent BCMA-Fc. After the pre-depletion, the ELISA with EctoD2/EctoD3-biotin is performed using the pre-depleted sera. Then it is considered that the signal obtained in the ELISA for the sample pre-depleted on EctoD2 is due to background (i.e. non-specific).

Two sets of human serum samples were analyzed, as well as a single serum sample of an individual with XLHED. The sample sets included 12 samples of cord blood serum (6 female and 6 male) and 11 samples of adult serum (5 female and 6 male). For validation of specificity and to determine the concentrations of inactive EDA as well as the concentrations of active EDA1 in the human serum samples, sera were first depleted twice (for 6 h and 16 h, respectively) in wells of ELISA plates coated with three different capture agents, BCMA-Fc, EDAR-Fc or EctoD2. Recombinant B-cell maturation antigen (BCMA, a member of the tumor necrosis factor receptor family)-Fc was employed as a control capture agent, which is not expected to capture EDA (this provides a "mock-depletion" control step). EDAR-Fc (recombinant EDAR) is expected to capture only active EDA1, but not EDA2 or inactive EDA1 (leading to depletion of only active EDA1 that binds to EDAR-Fc), and EctoD2 is expected to capture all forms of EDA (i.e. EDA2 and active and inactive EDA1). Depleted (and mock-depleted) sera were then transferred to EctoD2-coated ELISA plates, and bound EDA was revealed with biotinylated EctoD3 followed by HRP-coupled streptavidin. Absorbance readings of the ELISA trials were obtained and concentrations of EDA1 were determined from a standard curve of absorbance vs. EDA concentration. Difference between signals from mock-depleted serum and EctoD2 depleted serum indicates all EDA specific signal (i.e. EDA2 and active and inactive EDA1). Difference between signals from EctoD2 pre-depleted serum and EDAR-Fc pre-depleted serum indicates non-active EDA signal (i.e. all EDA unable to bind EDAR). Therefore, difference between these measurements is used to determine the percentage of active EDA1 that binds EDAR-Fc in serum samples.

Four different parameters were then calculated. The "specific concentration of EDA" (ng/mL) was determined by subtracting the EDA-depleted concentration determined with the EctoD2 capture agent from the EDA-depleted concentration determined with the BCMA capture reagent. The "inactive concentration of EDA" (ng/mL) was determined by subtracting the EDA-depleted concentration determined with the EctoD2 capture agent from the EDA-depleted concentration determined with the EDAR-Fc capture agent. "Inactive EDA" refers to EDA which is unable to bind to EDAR-Fc, and does not exclude the presence of active EDA2 in the sera. The "active EDA1 depletable concentration" (ng/mL) was determined by subtracting the inactive concentration of EDA from the specific concentration of EDA. Lastly, the percentage of EDA depletable on EDAR-Fc was calculated by subtracting the inactive concentration of EDA from the specific concentration of EDA and dividing by the specific concentration of EDA× 100. The mean values calculated for the four parameters are listed in Table 5. It was determined that the single XLHED serum sample did not give rise to a specific EDA signal after the pre-depletion step (not shown in Table 5).

In the standard curve, there is a good linear relationship between the concentration and the absorbance. For most serum samples, pre-depletion on EctoD2 yields signals close to baseline. The difference between pre-depletion with BCMA-Fc (mock-depletion) and pre-depletion on EctoD2 is considered as specific EDA (EDA1+EDA2, active and inactive). The fraction of the signal that can be depleted by pre-incubation on EDAR-Fc is used to calculate the percentage of active EDA1 (active=binds EDAR-Fc). There is no specific signal in the XLHED serum, despite a higher background. There is 1.5±0.4 ng/mL EDA in cord serum and 0.6±0.3 ng/ml in adult serum (p value $5 \times 10^{-6}$ between these 2 groups), of which 52±12% can bind to EDAR-Fc. There is 2.1±0.5 ng/ml specific EDA in fetal calf serum, of which 38±7% can bind EDAR-Fc. Pascal Schneider's serum (an adult male serum) was spiked with 2 ng/mL of Fc-EDA1. It was found that most of the Fc-EDA1 can be depleted, but concentrations lower than expected were found.

TABLE 5

Specificity Parameters Determined for the ELISA using EctoD2 as the Capture Agent and Ecto-D3-Biotin as the Detection Agent of the ELISA with a Pre-Depletion Step using BCMA-Fc, EDAR-Fc and EctoD2 as Pre-Depletion Agents

| Serum Sample | Specific EDA (ng/mL) ± SD | Inactive EDA (ng/mL) ± SD | Active EDA (ng/mL) ± SD | Percentage depletable on EDAR-Fc ± SD |
|---|---|---|---|---|
| Cord blood* | 1.51 ± 0.39 | 0.79 ± 0.24 | 0.72 ± 0.24 | 48 ± 12 |
| Adult** | 0.64 ± 0.28 | 0.30 ± 0.19 | 0.34 ± 0.11 | 56 ± 11 |
| Female cord blood§ | 1.57 ± 0.37 | 0.83 ± 0.18 | 0.74 ± 0.29 | 45 ± 12 |
| Female adult# | 0.51 ± 0.27 | 0.20 ± 0.14 | 0.31 ± 0.14 | 63 ± 8 |
| Male cord blood§ | 1.45 ± 0.43 | 0.74 ± 0.30 | 0.71 ± 0.20 | 49 ± 12 |
| Male adult§ | 0.75 ± 0.26 | 0.39 ± 0.19 | 0.37 ± 0.08 | 49 ± 9 |

*Mean values calculated from 12 determinations in cord blood sera.
**Mean values calculated from 11 determinations in adult sera.
§Mean values calculated from 6 determinations.
Mean values calculated from 5 determinations.

The parameters determined for the different groups of samples were subjected to a statistical analysis for calculation of p values. The calculated p values for the compared groups are shown below in Table 6.

TABLE 6

Determination of Statistical Significance in Comparison of Parameters for Different Serum Sample Groups

| Group A | Group B | p value |
|---|---|---|
| Cord Serum Specific EDA | Adult Serum Specific EDA | <0.001 |
| Cord Serum Inactive EDA | Adult Serum Inactive EDA | <0.001 |
| Cord Serum Active EDA | Adult Serum Active EDA | <0.001 |
| Cord Serum Percentage depletable EDA1 | Adult Serum Percentage depletable EDA1 | 0.0823 |
| Female Cord Serum Specific EDA | Male Cord Serum Specific EDA | 0.609 |
| Female Cord Serum Inactive EDA | Male Cord Serum Inactive EDA | 0.527 |
| Female Cord Serum Active EDA | Male Cord Serum Active EDA | 0.845 |
| Female Cord Serum Percentage depletable on EDAR-Fc | Male Cord Serum Percentage depletable on EDAR-Fc | 0.449 |
| Female Adult Serum Specific EDA | Male Adult Serum Specific EDA | 0.169 |
| Female Adult Serum Inactive EDA | Male Adult Serum Inactive EDA | 0.098 |
| Female Adult Serum Active EDA | Male Adult Serum Active EDA | 0.450 |
| Female Adult Serum Percentage depletable on EDAR-Fc | Male Adult Serum Percentage depletable on EDAR-Fc | 0.057 |

Conclusions—The absence of a specific signal in XLHED serum validates the ELISA. Serum concentrations of EDA are relatively homogenous within adults or cord blood. Thus, the 2.3-fold higher EDA concentration in cord serum compared to adult serum is highly significant. In all cases, about half of the specific EDA signal can bind EDAR (slightly more in adult sera compared to cord sera, but this is not significant). There are no sex-related differences. The pre-depletion scheme is a necessary aspect of the experiment and consumes 300 µL of serum. Without the pre-depletion step, the XLHED serum and a few other serum samples would have been scored positive because of high background levels. The spike experiment indicates that absolute concentration values must be considered with caution. The depletion also allows to distinguish EDA that can bind to EDAR from EDA that can not bind.

Reagents—EctoD2 (#1208-10), EDAR-Fc-930 (#1106-30), BCMA-Fc-739 clone H1 (#712-07), Fetal calf sera (3 different lots) (#1401-17), EctoD3-biot (#1209-05). All human sera were collected between December 2013 and January 2014. Normal human sera (#101-110. MMFM-MFFFFM. M=male. F=female), XLHED serum (Exon 1 mutant=EDA-null. Adult, male), sera from cord blood (#1-12 MFFMMFFFMFMM. 11 and 12 hemolyzed). Pascal Schneider's serum (#1304-04). Fc-EDA1 (APO200 #0701).

Methods—Depletion: For each serum sample, 6 wells of an ELISA plate were coated with EctoD2 at 1 µg/mL (2 wells), EDAR-Fc at 1 µg/mL (2 wells), and BCMA-Fc at 1 µg/mL in PBS (2 wells). O/N at 4° C. The plates were then blocked for 1 h at 37° C. Then 100 µl/well of serum (or Pascal's serum spiked with 2 ng/ml Fc-EDA1) (each serum on EctoD2, BCMA-Fc or EDAR-Fc) was added and the samples were incubated for 6 h at room temperature. The samples were then transferred to the second depleting well with the same coating with incubation O/N at 4° C. A standard curve of Fc-EDA1 in incubation buffer (100 µL at 2 ng/mL and 2-fold dilutions) was prepared. The samples were then transferred to the ELISA plates. For the ELISA, EctoD2 was coated at 1 µg/ml in PBS. O/N at 4° C. Blocking was performed for 1 h at 37° C. Serum samples from the second depletion wells were then added with incubation for 1 h at 37° C. Detection was initiated with EctoD3-biot at 1 µg/mL with incubation for 1 h at 37° C., followed by HRP-streptavidin (1/4000) 30 min at 37° C.

EQUIVALENTS AND SCOPE

The person skilled in the art will appreciate that the invention described herein may be varied and/or modified by features other than those specifically described. It is to be understood that the invention as defined by the appended claims encompasses such variations and modifications. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to be embraced therein.

Various references are cited throughout this specification. Each of these references are incorporated herein by reference in entirety.

What is claimed is:

1. An isolated monoclonal antibody or isolated monoclonal antibody fragment or antigen binding portion or fragment thereof, that binds human and/or mouse and/or avian EDA1 (Ectodysplasin A1), said antibody comprising:
   i. a heavy chain variable region comprising the complementary determining region (CDR) amino acid sequences: SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; and/or
   ii. a light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18.

2. An isolated monoclonal antibody or isolated monoclonal antibody fragment or antigen binding portion or fragment thereof, that binds human and/or mouse and/or avian EDA1, the antibody comprising a heavy chain variable region and a light chain variable region, wherein the heavy chain variable region comprises an amino acid sequence selected from the group consisting of: (a) SEQ ID NO: 51, 53 and 55; (b) amino acid sequences that differ from those sequences specified in (a) by 1, 2, 3, 4, 5, 6, 7, 8, 9, or 10 conservative amino acid substitutions; and (c) amino acid sequences having at least 95% sequence identity to the sequences specified in (a) or (b); and
   wherein the light chain variable region comprises an amino acid sequence selected from the group consisting of: (a) SEQ ID NO: 52, 54 and 56; (b) amino acid sequences that differ from those sequences specified in (a) by 1, 2, 3, 4, 5, 6, 7, 8, 9, or 10 conservative amino acid substitutions; and (c) amino acid sequences having at least 95% sequence identity to the sequences specified in (a) or (b).

3. The isolated monoclonal antibody or isolated monoclonal antibody fragment or antigen binding portion or fragment thereof of claim 1 wherein the antibody is selected from the group consisting of: (a) an antibody (mAbEDA-EctoD2) comprising: a heavy chain comprising the CDRs of SEQ ID NOs: 1,2 and 3 and comprising at least 95% sequence identity to SEQ ID NO: 51 and a light chain comprising the CDRs of SEQ ID NOs: 4,5 and 6 and comprising at least 95% sequence identity to SEQ ID NO: 52, (b) an antibody (mAbEDA-EctoD1) comprising a heavy chain comprising the CDRs of SEQ ID NOs: 7,8 and 9 and comprising at least 95% sequence identity to SEQ ID NO: 53 and a light chain comprising the CDRs of SEQ ID NOs: 10,11 and 12 and comprising at least 95% sequence identity to SEQ ID NO: 54, and (c) an antibody (mAbEDA-EctoD3) comprising: a heavy chain comprising the CDRs of SEQ ID NOs: 13,14 and 15 and comprising at least 95% sequence identity to SEQ ID NO: 55 and a light chain comprising the CDRs of SEQ ID NOs: 16,17 and 18 and comprising at least 95% sequence identity to SEQ ID NO: 56.

4. The isolated monoclonal antibody or isolated monoclonal antibody fragment or antigen binding portion or fragment thereof of claim 1, wherein the antibody, antibody fragment, or antigen binding portion or fragment thereof is an antagonist of human and/or mouse and/or avian EDA1, or an antagonist of human and/or mouse and/or avian EDA2 (Ectodysplasin A2).

5. The isolated monoclonal antibody or isolated monoclonal antibody fragment or antigen binding portion or fragment thereof of claim 4 wherein the EC50 (effective concentration) for inducing half maximal decrease of cell viability in EDAR (Ectodysplasin A receptor)-Fas-expressing Jurkat cells is equal to or less than 200 ng/mL.

6. The isolated monoclonal antibody or isolated monoclonal antibody fragment or antigen binding portion or fragment thereof of claim 1 which binds to human and/or mouse and/or avian EDA1 with an affinity constant (KD) of at least $10^{-8}$M.

7. The isolated monoclonal antibody or isolated monoclonal antibody fragment or antigen binding portion or fragment thereof of claim 1, which is
   (i) a humanized antibody, antibody fragment, or antigen binding portion or fragment thereof,
   (ii) monovalent,
   (iii) a single chain antibody, antibody fragment, or antigen binding portion or fragment thereof,
   (iv) a Fab, F(ab)'2, Fv, Fab/c, Fv, single chain Fv (scFv), or Fd fragment,
   (v) a chimeric antibody, antibody fragment, or antigen binding portion or fragment thereof, or
   (vi) a fusion protein.

8. The isolated monoclonal antibody or isolated monoclonal antibody fragment or antigen binding portion or fragment thereof of claim 7, wherein a heavy chain is selected from the group consisting of heavy chain of IgG, IgM, IgA, IgE, single chain antibody, immunoglobulin-derived constructs, and non-antibody binding proteins.

9. The isolated monoclonal antibody or isolated monoclonal antibody fragment or antigen binding portion or fragment thereof of claim 8, wherein the non-antibody binding protein is selected from the group consisting of adnectins, Affibody, DARPins (Designed Ankyrin Repeat Proteins), avimers, anticalins, and nucleotide based reagents.

10. The isolated monoclonal antibody or isolated monoclonal antibody fragment or antigen binding portion or fragment thereof of claim 8, wherein the IgG is selected from the group consisting of IgG1, IgG2, IgG3, IgG4, mutated IgG1 that is no longer recognized by FcR(Fc receptor), and mutated IgG4 that no longer undergoes heavy chain swapping.

11. The isolated monoclonal antibody or isolated monoclonal antibody fragment or antigen binding portion or fragment thereof of claim 1, which is conjugated to a ligand and/or a tag, wherein the ligand and/or tag is polyethylene glycol (PEG) or a label.

12. An isolated nucleic acid molecule encoding an isolated monoclonal antibody or isolated monoclonal antibody fragment or antigen binding portion or fragment thereof of claim 1.

13. An expression vector comprising at least one copy of the nucleic acid molecule of claim 12.

14. A host cell comprising the expression vector of claim 13.

15. A transgenic non-human animal having a genome comprising the isolated nucleic acid molecule of claim 12 and/or the expression vector of claim 13.

16. A hybridoma secreting isolated monoclonal antibody or isolated monoclonal antibody fragment or antigen binding portion or fragment thereof of claim 1.

17. A kit for performing an immunoassay, the kit comprising the isolated monoclonal antibody or isolated monoclonal antibody fragment or antigen binding portion or fragment thereof of claim 1 or the isolated nucleic acid molecule of claim 12; and one or more immunoassay detection reagent, and instructions for performing an immunoassay configured to determine an amount of EDA1 in a sample.

* * * * *